("12") United States Patent  (10) Patent No.: US 7,666,627 B2
Gál et al.  (45) Date of Patent: Feb. 23, 2010

(54) FOLDED RECOMBINANT CATALYTIC FRAGMENTS OF MULTIDOMAIN SERINE PROTEASES, PREPARATION AND USES THEREOF

(75) Inventors: Péter Gál, Budapest (HU); Péter Závodszky, Budapest (HU); Géza Ambrus-Aikelin, Keszthely (HU); József Kardos, Budapest (HU)

(73) Assignee: TargetEx Kft., Dunakeszi (HU)

( * ) Notice: Subject to any disclaimer, the term of this patent is extended or adjusted under 35 U.S.C. 154(b) by 239 days.

(21) Appl. No.: 10/636,602

(22) Filed: Aug. 8, 2003

(65) Prior Publication Data

US 2005/0032157 A1 Feb. 10, 2005

Related U.S. Application Data

(60) Provisional application No. 60/401,755, filed on Aug. 8, 2002.

(51) Int. Cl.
C12N 15/62 (2006.01)
C12N 9/64 (2006.01)
C12N 15/70 (2006.01)

(52) U.S. Cl. .................. 435/69.7; 435/226; 435/252.3; 435/252.33; 435/320.1; 536/23.4

(58) Field of Classification Search ........................ None
See application file for complete search history.

(56) References Cited

U.S. PATENT DOCUMENTS 5,578,710 A 11/1996 Ambrosius et al.
5,593,865 A 1/1997 Rudolph et al.
5,597,691 A * 1/1997 Houghton et al. ............. 435/23
6,013,767 A * 1/2000 Nakamura ................... 530/350

(Continued)

FOREIGN PATENT DOCUMENTS

JP 07238100 A2 9/1995
WO WO02/06460 A2 1/2002

OTHER PUBLICATIONS

Eakin et al., 1993, "Production of crystallizable cruzain, the major cysteine protease from *Trypanosoma cruzi*", The Journal of Biological Chemistry, vol. 268, No. 9, pp. 6115-6118.*

(Continued)

*Primary Examiner*—Anand U Desai
*Assistant Examiner*—William W Moore
(74) *Attorney, Agent, or Firm*—Hahn & Voight PLLC; Jason D. Voight

(57) ABSTRACT

The invention relates to unglycosylated folded C-terminal fragments of a multidomain serine protease of the complement cascade obtainable by expression in a bacterial host, wherein said serine protease is capable of binding a recognition molecule of the complement cascade, e.g. C1 or MBL. The invention also relates to methods and bacterial expression vectors for the preparation of said fragments, uses of said fragments for raising antibodies and screening substrates or inhibitors of said serine proteases and uses of the fragments in research and treatment of complement related disorders. The invention also relates to assay methods for assessing MASP-1 and MASP-2 levels in a sample of biological origin.

The invention provides for research tools, assays and diagnostic kits useful in complement research and research and diagnosis of complement related disorders.

5 Claims, 15 Drawing Sheets

Expression of the MASP-1 and MASP-2 fragments

MASP-1 and MASP-2 fragments expressed in *E. coli*

U.S. PATENT DOCUMENTS

| | | | |
|---|---|---|---|
| 6,235,494 B1 | 5/2001 | Hugli | |
| 6,297,024 B1 | 10/2001 | Hugli et al. | |
| 6,485,957 B1* | 11/2002 | Darrow et al. | 435/226 |
| 6,515,002 B2 | 2/2003 | Illig et al. | |
| 6,524,589 B1* | 2/2003 | Reichert et al. | 424/228.1 |
| 6,969,601 B2* | 11/2005 | Jensenius et al. | 435/226 |
| 7,060,267 B2* | 6/2006 | Jensenius et al. | 424/94.64 |
| 7,083,786 B2* | 8/2006 | Jensenius et al. | 424/145.1 |
| 7,112,414 B2* | 9/2006 | Jensenius et al. | 435/23 |
| 7,173,115 B2* | 2/2007 | Pennica et al. | 536/23.1 |
| 2001/0006793 A1* | 7/2001 | Bjornsti et al. | 435/23 |
| 2002/0106775 A1* | 8/2002 | Wang et al. | 435/215 |
| 2003/0186419 A1* | 10/2003 | Jensenius | 435/226 |

OTHER PUBLICATIONS

Yananoto-Katayama et al., 2001, "Site directed removal of N-glycosylation sites in BST-1/CD157: effects on molecular and functional heterogeneity", Biochemical Journal, vol. 357, pp. 385-392.*

Cseh, S., et al., 1996, "Functional effects of domain deletions in a multidomain serine protease, C1r", Molecular Immunology, vol. 33, Nos. 4/5, pp. 351-359.*

Gal, P. et al., 1998, "Structure and function of the serine protease subcomponents of C1: Protein engineering studies", Immunobiology, vol. 199, pp. 317-326.*

Gal, P., et al., 2001, "Strucure and function of Complement activating enzyme complexes: C1 and MBL-MASPs", Current Protein and Peptide Science, vol. 2, pp. 43-59.*

Gal, P., et al., 2002, "C1s, the protease messenger of C1: Structure, function and physiological significance", Immunobiology, vol. 205, pp. 383-394.*

Hajela, K., et al., 2002, "The biological functions of MBL-associated serine proteases (MASPs)", Immunobiology, vol. 205, pp. 467-475.*

Ambrus, G., et al., 2003, "Natural substrates and inhibitors of mannan-binding lectin-associated serine protease-1 and -2: A study on recombinant catalytic fragments", The Journal of Immunology, vol. 170, pp. 1373-1382.*

Monika Budayova-Spano et al.; "The crystal structure of the zymogen catalytic domain of complement protease C1r reveals that a disruptive mechanical stress is required to trigger activation of the C1 complex"; The EMBO Journal; vol. 21, No. 3, pp. 231-239, 2002.

Ce-Belle Chen et al.; "Stoichiometry of Complexes between Mannose-binding Protein and Its Associated Serine Proteases"; The Journal of Biological Chemistry; vol. 276, No. 28, Issue of Jul. 13, pp. 25894-25902, 2001.

Christine Gaboriaud, et al.; "Crystal structure of the catalytic domain of human complement C1s: a serine protease with a handle"; The EMBO Journal; vol. 19, No. 8, pp. 1755-1765, 2000.

Péter Gál et al.; "Expression of Hemolytically Active Human Complement Component C1r Proenzyme in Insect Cells Using a Baculovirus Vector"; Complement and Inflammation; vol. 6, 433-441; 1989.

József Kardos, et al.; "The Role of the Individual Domains in the Structure and Function of the Catalytic Region of a Modular Serine Protease, C1r"; The Journal of Immunology, vol. 167, 5202-5208, 2001.

Monique Lacroix et al.; "Assembly and Enzymatic Properties of the Catalytic Domain of Human Complement Protease C1r"; The Journal of Biological Chemistry, vol. 276, No. 39, Issue of Sep. 28, pp. 36233-36240, 2001.

Véronique Rossi et al.; "Baculovirus-mediated Expression of Truncated Modular Fragments from the Catalytic Region of Human Complement Serine Protease C1s"; The Journal of Biological Chemistry, vol. 273, No. 2, Issue of Jan. 9, pp. 1232-1239, 1998.

Véronique Rossi et al.; "Substrate Specificities of Recombinant Mannan-binding Lectin-associated Serine Proteases-1 and -2"; The Journal of Biological Chemistry, vol. 276, No. 44, Issue of Nov. 2, pp. 40880-40887, 2001.

Nicole M. Thielens et al.; Interaction Properties of Human Mannan-Binding Lectin (MBL)-Associated Serine Proteases-1 and -2, MBL-Associated Protein 19, and MBL; The Journal of Immunology, vol. 166, 5068-5077, 2001.

* cited by examiner

Pathways of complement activation
Unclarified parts standing in the focus of the attention
of the present study are indicated in light grey color.

Modular structure of proteins known to be associated with MBL

Expression of the MASP-1 and MASP-2 fragments

MASP-1 and MASP-2 fragments expressed in *E. coli*

Purification of the MASP-1 and MASP-2 fragments

Coomassie stained SDS-PAGE of the purified MASP-1 and MASP-2 fragments
(MASP-1γB, MASP-2γB, MASP-2 CCP2-SP, MASP-2 SP)

C2, live C3, dead C3, C4 cleavage

A: Coomassie stained reducing SDS-PAGE of C2 cleaved by the MASP

B: Coomassie stained reducing SDS-PAGE of C3 cleaved by the MASP fragments

C: Coomassie stained reducing SDS-PAGE of C4 cleaved by the MASP fragments

The reaction of the MASP-1 and MASP-2 fragments with C1-inhibitor and alpha-2-macroglobulin Radiogramm of an SDS-PAGE run under reducing conditions of the indicated inhibitors with the MASP-1 and MASP-2 fragments (MASP-1γB, MASP-2γB, MASP-2 CCP2-SP, MASP-2 SP)

Decrease in peak area [%]

1. : MASP3 CCP1-CCP2-SP (1319 bp)
3.   MASP3 SP (908 bp)

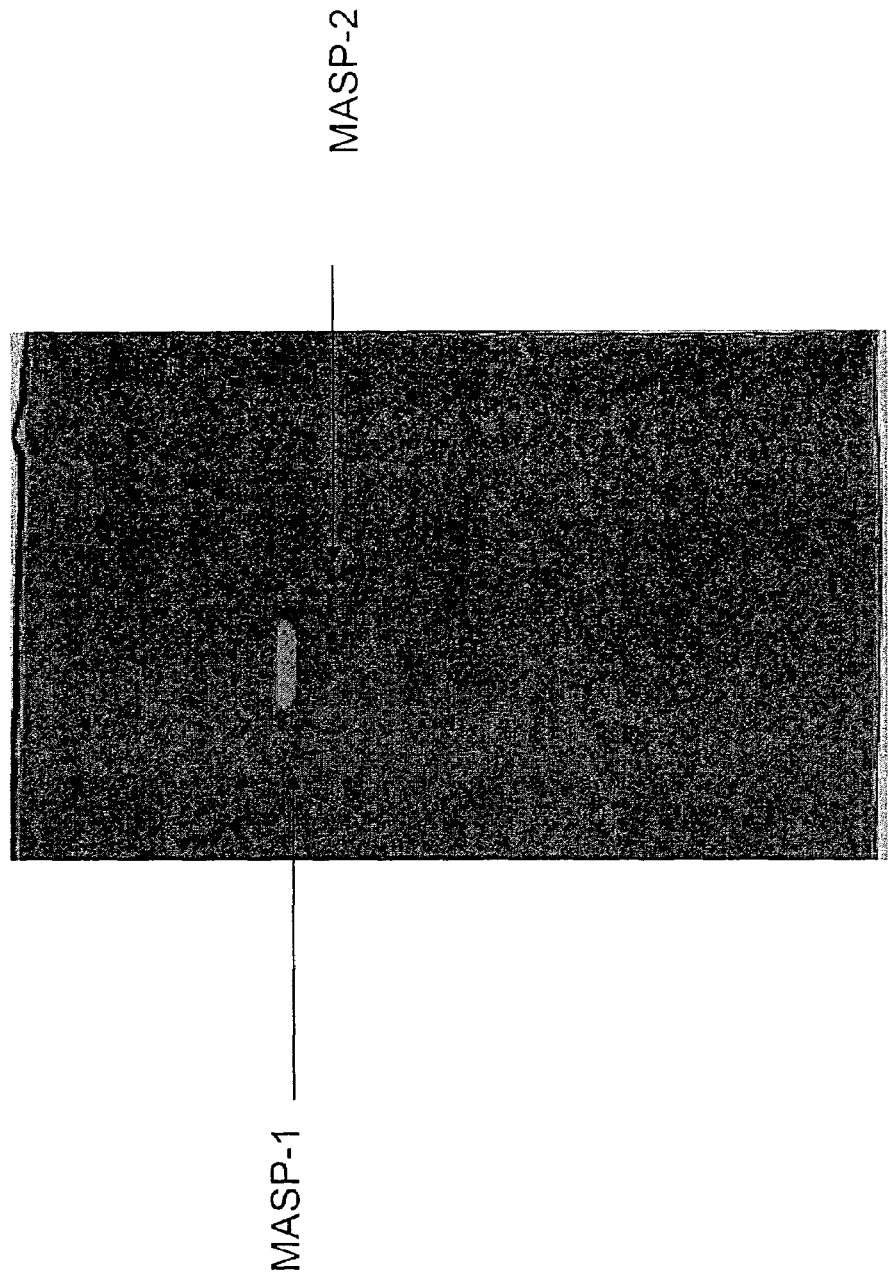

US 7,666,627 B2

SEQUENCE LISTING

```
<160> NUMBER OF SEQ ID NOS: 21

<210> SEQ ID NO 1
<211> LENGTH: 36
<212> TYPE: DNA
<213> ORGANISM: Artificial sequence
<220> FEATURE:
<223> OTHER INFORMATION: forward primer for the MASP-1 CCP-1-CCP2-SP
      construct
<220> FEATURE:
<221> NAME/KEY: misc_feature
<222> LOCATION: (1)..(36)
<220> FEATURE:
<221> NAME/KEY: misc_feature
<222> LOCATION: (1)..(36)
<223> OTHER INFORMATION: comprises an NheI restriction site

<400> SEQUENCE: 1
gcggctagca tgactggtaa tgagtgccca gagcta                              36

<210> SEQ ID NO 2
<211> LENGTH: 33
```

```
<212> TYPE: DNA
<213> ORGANISM: Artificial sequence
<220> FEATURE:
<223> OTHER INFORMATION: reverse primer for the MASP-1 CCP-1-CCP2-SP
      construct
<220> FEATURE:
<221> NAME/KEY: misc_feature
<222> LOCATION: (1)..(33)
<223> OTHER INFORMATION: comprises an EcoRI restriction site

<400> SEQUENCE: 2
gcggaattct cagttcctca ctccggtgac cct                                33

<210> SEQ ID NO 3
<211> LENGTH: 34
<212> TYPE: DNA
<213> ORGANISM: Artificial sequence
<220> FEATURE:
<223> OTHER INFORMATION: reverse primer for the three MASP-2 constructs
<220> FEATURE:
<221> NAME/KEY: misc_feature
<222> LOCATION: (1)..(34)

<400> SEQUENCE: 3
gcggaattct taaaaatcac taattatgtt ctcg                               34

<210> SEQ ID NO 4
<211> LENGTH: 36
<212> TYPE: DNA
<213> ORGANISM: Artificial sequence
<220> FEATURE:
<223> OTHER INFORMATION: forward primers for THE MASP-2 CCP1-CCP2-SP
      construct
<220> FEATURE:
<221> NAME/KEY: misc_feature
<222> LOCATION: (1)..(36)

<400> SEQUENCE: 4
gcggctagca tgactggttg gaagatccac tacacg                             36

<210> SEQ ID NO 5
<211> LENGTH: 37
<212> TYPE: DNA
<213> ORGANISM: Artificial sequence
<220> FEATURE:
<223> OTHER INFORMATION: forward primer for the MASP-2  CCP2-SP
      construct
<220> FEATURE:
<221> NAME/KEY: misc_feature
<222> LOCATION: (1)..(37)

<400> SEQUENCE: 5
gcggctagca tgactattgt tgactgtggc cctcctg                            37

<210> SEQ ID NO 6
<211> LENGTH: 36
<212> TYPE: DNA
<213> ORGANISM: Artificial sequence
<220> FEATURE:
<223> OTHER INFORMATION: forward primers for the MASP-2 SP construct
<220> FEATURE:
<221> NAME/KEY: misc_feature
<222> LOCATION: (1)..(36)

<400> SEQUENCE: 6
gcggctagca tgactcctgt ttgtggacta tcagcc                             36

<210> SEQ ID NO 7
<211> LENGTH: 33
```

```
<212> TYPE: DNA
<213> ORGANISM: Artificial sequence
<220> FEATURE:
<223> OTHER INFORMATION: Reverse primer for the MASP-3 SP domain
<220> FEATURE:
<221> NAME/KEY: misc_feature
<222> LOCATION: (1)..(33)
<223> OTHER INFORMATION: the primer comprises an EcoRI cleavage site

<400> SEQUENCE: 7
gcggaattct caccgttcca cctggggctc cac                                  33

<210> SEQ ID NO 8
<211> LENGTH: 36
<212> TYPE: DNA
<213> ORGANISM: Artificial sequence
<220> FEATURE:
<223> OTHER INFORMATION: Forward primer for the MASP-3 SP domain
<220> FEATURE:
<221> NAME/KEY: misc_feature
<222> LOCATION: (1)..(36)
<223> OTHER INFORMATION: The primer comprises an NheI cleavage site

<400> SEQUENCE: 8
gcggctagca tgactcttcc agagtgtggt cagccc                               36

<210> SEQ ID NO 9
<211> LENGTH: 30
<212> TYPE: DNA
<213> ORGANISM: Artificial sequence
<220> FEATURE:
<223> OTHER INFORMATION: Forward primer for "nested" PCR for MASP-3
      CCP2-SP and CCP1-CCP2-SP constructs
<220> FEATURE:
<221> NAME/KEY: misc_feature
<222> LOCATION: (1)..(30)

<400> SEQUENCE: 9
cctgttccat agtgacaact cgggagagaa                                      30

<210> SEQ ID NO 10
<211> LENGTH: 30
<212> TYPE: DNA
<213> ORGANISM: Artificial sequence
<220> FEATURE:
<223> OTHER INFORMATION: Reverse primer for "nested" PCR for MASP-3
      CCP2-SP and CCP1-CCP2-SP constructs
<220> FEATURE:
<221> NAME/KEY: misc_feature
<222> LOCATION: (1)..(30)

<400> SEQUENCE: 10
gggaggcagg ccccgaggaa gtaagtcagc                                      30

<210> SEQ ID NO 11
<211> LENGTH: 29
<212> TYPE: DNA
<213> ORGANISM: Artificial sequence
<220> FEATURE:
<223> OTHER INFORMATION: forward primer for the C1r CCP1-CCP2-SP
      construct
<220> FEATURE:
<221> NAME/KEY: misc_feature
<222> LOCATION: (1)..(29)

<400> SEQUENCE: 11
gcgaagcttg ccccagccc aagaccta                                         29

<210> SEQ ID NO 12
```

<211> LENGTH: 29
<212> TYPE: DNA
<213> ORGANISM: Artificial sequence
<220> FEATURE:
<223> OTHER INFORMATION: forward primer for the C1r CCP2-SP construct
<220> FEATURE:
<221> NAME/KEY: misc_feature
<222> LOCATION: (1)..(29)

<400> SEQUENCE: 12
gcgaagcttg tgggcagccc cgaaacctg                29

<210> SEQ ID NO 13
<211> LENGTH: 27
<212> TYPE: DNA
<213> ORGANISM: Artificial sequence
<220> FEATURE:
<223> OTHER INFORMATION: forward primer for the C1r SP construct
<220> FEATURE:
<221> NAME/KEY: misc_feature
<222> LOCATION: (1)..(27)

<400> SEQUENCE: 13
gcgaagcttg tgggaagccc gtgaacc                  27

<210> SEQ ID NO 14
<211> LENGTH: 15
<212> TYPE: DNA
<213> ORGANISM: Artificial sequence
<220> FEATURE:
<223> OTHER INFORMATION: Tag sequence for ligation into the pET-17b
    expression vector for the C1r constructs
<220> FEATURE:
<221> NAME/KEY: misc_feature
<222> LOCATION: (1)..(15)

<400> SEQUENCE: 14
atgtgcaccc aagct                               15

<210> SEQ ID NO 15
<211> LENGTH: 37
<212> TYPE: DNA
<213> ORGANISM: Artificial sequence
<220> FEATURE:
<223> OTHER INFORMATION: sense primer sequence for verification of C1r
    construct (Arg463Gln mutant) by DNA sequencing
<220> FEATURE:
<221> NAME/KEY: misc_feature
<222> LOCATION: (1)..(37)

<400> SEQUENCE: 15
gtggaacaga ggcagcagat aatcggaggg caaaaag       37

<210> SEQ ID NO 16
<211> LENGTH: 33
<212> TYPE: DNA
<213> ORGANISM: Artificial sequence
<220> FEATURE:
<223> OTHER INFORMATION: sense primer sequence for verification of C1r
    construct (Ser654Ala mutant) by DNA sequencing
<220> FEATURE:
<221> NAME/KEY: misc_feature
<222> LOCATION: (1)..(33)

<400> SEQUENCE: 16
gcctgccagg gggatgctgg gggcgttttt gca           33

<210> SEQ ID NO 17
<211> LENGTH: 7

```
<212> TYPE: PRT
<213> ORGANISM: Artificial sequence
<220> FEATURE:
<223> OTHER INFORMATION: A heptapeptide cleaved from MASP-2 CCP1-CCP2-SP
      fragment
<220> FEATURE:
<221> NAME/KEY: PEPTIDE
<222> LOCATION: (1)..(7)

<400> SEQUENCE: 17

Ala Ser Met Thr Gly Trp Lys
1               5

<210> SEQ ID NO 18
<211> LENGTH: 13
<212> TYPE: PRT
<213> ORGANISM: Artificial sequence
<220> FEATURE:
<223> OTHER INFORMATION: oligopeptide library
<220> FEATURE:
<221> NAME/KEY: PEPTIDE
<222> LOCATION: (1)..(13)
<223> OTHER INFORMATION: X is K, R, Y, L, F, W or P
<220> FEATURE:
<221> NAME/KEY: misc_feature
<222> LOCATION: (5)..(5)
<223> OTHER INFORMATION: Xaa can be any naturally occurring amino acid

<400> SEQUENCE: 18

His Ala Ala Pro Xaa Ser Ala Asn Ile Gln Ile Ala Ile
1               5                   10

<210> SEQ ID NO 19
<211> LENGTH: 3
<212> TYPE: PRT
<213> ORGANISM: Artificial sequence
<220> FEATURE:
<223> OTHER INFORMATION: Ala-Ser-Met fragment of the T7 tag
<220> FEATURE:
<221> NAME/KEY: PEPTIDE
<222> LOCATION: (1)..(3)

<400> SEQUENCE: 19

Ala Ser Met
1

<210> SEQ ID NO 20
<211> LENGTH: 4
<212> TYPE: PRT
<213> ORGANISM: Artificial sequence
<220> FEATURE:
<223> OTHER INFORMATION: Ala-Ser-Met-Thr fragment of the T7 tag
<220> FEATURE:
<221> NAME/KEY: PEPTIDE
<222> LOCATION: (1)..(4)

<400> SEQUENCE: 20

Ala Ser Met Thr
1

<210> SEQ ID NO 21
<211> LENGTH: 29
<212> TYPE: DNA
<213> ORGANISM: Artificial sequence
<220> FEATURE:
<223> OTHER INFORMATION: reverse primer
```

```
-continued

<220> FEATURE:
<221> NAME/KEY: misc_feature
<222> LOCATION: (1)..(29)

<400> SEQUENCE: 21
gcggtcgact cagtcctcct cctccatct                                                29
```

FOLDED RECOMBINANT CATALYTIC FRAGMENTS OF MULTIDOMAIN SERINE PROTEASES, PREPARATION AND USES THEREOF

The present application claims priority to U.S. Provisional Application Ser. No. 60/401,755, filed Aug. 8, 2002.

FIELD OF THE INVENTION

The invention relates to unglycosylated folded C-terminal fragments of a multidomain serine protease of the complement cascade obtainable by expression in a bacterial host, wherein said serine protease is capable of binding a recognition molecule of the complement cascade, e.g. C1 or MBL. The invention also relates to methods and bacterial expression vectors for the preparation of said fragments, uses of said fragments for raising antibodies and screening substrates or inhibitors of said serine proteases and uses of the fragments in research and treatment of complement related disorders. The invention also relates to assay methods for assessing levels of multidomain complement serine proteases in samples of biological origin.

BACKGROUND ART

The complement system is an important component of the innate immune defense. A prerequisite for the complement system to exert its function is its activation, which can occur through three different ways: the classical, the lectin and the alternative pathways. Invading pathogenic microorganisms (e.g. bacteria, viruses, and fungi) can directly initiate each distinct pathway before the adaptive immune response is developed.

The complement cascade, however, if inappropriately activated, can cause a significant amount of inflammation, tissue damage, and other disease states such as the autoimmune diseases. Disease states implicating the complement system in inflammation and tissue damage include the following: the intestinal inflammation of Crohn's disease (Ahrenstedt et al., 1990), thermal injury (burns, frostbite) (Gelfand et al, 1982; Demling et al., 1989), hemodialysis (Deppisch et al., 1990; Kojima et al., 1989), and post pump syndrome in cardiopulmonary bypass (Chenoweth et al., 1981; Chenoweth et al., 1986; Salama et al., 1988), supposedly it is involved in the development of fatal complication in sepsis (Hack et al., 1989) and causes tissue injury in animal models of autoimmune diseases. The complement system is also involved in hyperacute allograft and hyperacute xenograft rejection (Knechtle et al., 1985); Guttman, 1974; Adachi et al., 1987). Complement activation during immunotherapy with recombinant IL-2 appears to cause the severe toxicity and side effects observed from IL-2 treatment (Thijs et al., 1990). Further deleterious effects of improper activation or overactivation of the complement system is described e.g. in U.S. application Ser. No. 2002037915.

Based on increased incidence of infections in individuals with MBL deficiency, there are indications in the art that the lectin pathway is associated with the following diseases: HIV (increased susceptibility of infection), cystic fibrosis, systemic lupus erythematosus, rheumatoid arthritis, recurrent miscarriage, meningitis, cryptospirodiosis, chronic hepatitis C (Dumestre-Perard, 2002) (as a disease modulator). Complement activation, contributing to the inflammatory reaction upon observed in reperfusion injury is mediated through the lectin pathway (Monsinjon, 2001, Collard, 2000). In a rat animal model, blockade of the lectin pathway protected the heart from ischemia-reperfusion by reducing neutrophil infiltration and attenuating proinflammatory gene expression. (Jordan, 2001)

It is of particular importance therefore to study key molecules of the complement system, their structure and function, therefore to obtain these molecules or functional or folded fragments thereof in sufficient quantities and in a pure form to obtain appropriate research tools, to develop assays for detecting said molecules and to find, design or raise molecules for effecting the function of the complement system or for supplying deficiencies of it and also treating decease conditions associated with irregular working of this system.

The activation of the complement system (like of other proteolytic cascades) results in the sequential activation of serine protease zymogens. The first step in the lectin and the classical pathways is the binding of a specific recognition molecule (MBL or C1q, respectively) to activator structures, which is followed by the activation of associated serine proteases (Gál, 2001).

Although the lectin pathway was discovered more than a decade ago (Kawasaki, 1989), there are many uncertainties concerning the composition of the activation complex and the substrate specificities of the MBL-associated serine proteases (MASPs). MBL is a member of the collectin family of proteins and binds to specific carbohydrate arrays on the surface of various pathogens through C-type lectin domains (Turner, 1996). Up to date three MBL-associated serine proteases have been described. First, a single enzyme 'MASP' was identified and characterized as the enzyme, which is responsible for the initiation of the complement cascade (i.e. cleaving C2, C4 and possibly C3) (Matsushita, 1992/Ji, Y-H., 1993). Later it turned out that 'MASP' is in fact a mixture of two proteases: MASP-1 and MASP-2 (Thiel, 1997). It was demonstrated, that the MBL-MASP-2 complex alone is sufficient for complement activation (Vorup-Jensen, 2000). This is a significant difference from the C1 complex, where the coordinated action of two serine proteases (C1r and C1s) leads to the activation of the complement system. Here, C1q is the recognition subunit of the complex, while C1r and C1s are highly specific serine proteases (with Mrs 86.5 kDa and 80 kDa, respectively), which are responsible for the catalytic function of C1. A specific feature of the C1r and C1s serine proteases is that they form a distinct structural unit, the $Ca^{2+}$-dependent C1s-C1r-C1r-C1s tetramer, which makes possible the coordinated action of the two enzymes within the C1 complex. This tetramer associates with C1q to yield the heteropentameric C1 complex. C1r and C1s are present in the C1 complex in zymogen form, and become activated after C1q binds to an activator. The first enzymatic event during the activation process is the autoactivation of C1r. Activated C1r then activates zymogen C1s, which in turn cleaves C4 and C2.

The role of MASP-1 in the MBL-MASPs complex remained unknown. It was proposed, that MASP-1 could directly cleave C3 and thereby activate complement (Matsushita, 1995/Matsushita, 2000), but other laboratories debated these results (Wong, 1999/Zhang, 1998). Recently, a novel protease, MASP-3 has been isolated, however, its function is yet to be resolved (Dahl, 2001). Several lines of evidences suggest that there are different MBL-MASPs complexes (Thielens, 2001/Dahl, 2001) and a large fraction of the total MASPs in serum is not complexed with MBL (Terai, 1997/Thiel, 2000).

The MASPs together with C1r and C1s, form a family of proteases with identical domain organization (Sim, 2000/Volanakis, 1998). In these enzymes the first N-terminal CUB domain is followed by an EGF-like domain and the second CUB domain. A tandem repeat of complement control protein modules (CCP1 and CCP2) precedes the C-terminal serine protease domain (SP). Upon activation an Arg-Ile bond is cleaved in the serine protease domain of these zymogens.

Although the substrate specificities of MASP-1 and MASP-2 has been studied using natural and recombinant proteins, several important questions remained unanswered in the art. MASP-1 was shown to cleave C3 and C2 (Matsushita, 2000), but this action may not be sufficient for direct complement activation (Rossi, 2001). If the cleavage of C3 by MASP-1 proves to be insignificant then the field is still open to assess the biological importance of MASP-1. This could be possibly accomplished by identifying the range of its substrate specificity and the degree of its specific activity and by finding a 'better' natural substrate than C3. Previous studies showed that MASP-2 digested C2 and C4 efficiently, with rates similar to C1s, a classical pathway enzyme (Vorup-Jensen, 2000/Rossi, 2001). However, the contribution of the individual domains to the enzymatic properties of MASP-2 has not yet been determined. It is accepted that C1-inhibitor reacts with both proteases (Matsushita, 2000), but the rates of the reactions are unknown and the role of another inhibitory protein, alpha-2-macroglobulin, is rather debated (Wong, 1999/Rossi, 2001/Gulati, 2002). To sum up, differences in function and biological role of MASP-1 and MASP-2 are unclear according to the art.

Similarly, before the creation of the present invention, the role of the CCP and SP domains of C1r was unclear. The CCP repeat is about 60 residues in length and is widespread among complement proteins. It appeared to be likely that the CCP domains significantly contribute to the specificity of the interaction and catalytic properties of the γB fragment. For example a recent structural model of $(\gamma B)_2$ suggest a loose head-to-tail assembly of the monomers, where the γ-chain (the two CCP modules and the activation peptide) of one monomer interacts with the serine protease module of the other monomer (8).

Moreover, the autoactivation mechanism was unclear. Which domain is necessary to autoactivation? At all, are the individual domains separate folding units? Can folded fragments be prepared? Are they active?

The answer to these questions and other problems of the art is an important prerequisite of further research aiming the treatment of complement related disorders.

The main reason for these uncertainties concerning biological function of these proteases is the lack of availability of active and/or native recombinant proteins in a sufficient quantity and purity. The functional characterization has been retarded by the fact that their serum concentration is very low (in the case of MASPs: [MASP-1]=6 μg/ml, [MASP-2]≈2 μg/ml) (Hajela, 2002) which rendered their isolation extremely difficult. Most MASP preparations obtained from serum were usually cross-contaminated with other MASP species. Therefore, precise experiments could not be carried out in many cases. Also, though methods for determining in vivo levels of a mixture of MASPs have been known (e.g. U.S. Pat. No. 6,235,494 and U.S. Pat. No. 6,294,024) assessing MASP-1 and MASP-2 levels, differentiating one from the other, caused problems according to the art.

Though JP 7238100 (Matsushita et al, 1995) is directed to a monoclonal antibody against human MASP, the defined character of such an antibody is questionable since the publication does not make a distinction between MASP-1 and MASP-2. In general, due to the lack of sufficiently pure preparations antibodies for native MASP proteins could not be produced according to the art with a good reliability.

Similarly, a search for drugs, e.g. inhibitors, alleviating symptoms associated with overactivity of the complement system had been greatly hindered by the lack of availability of folded, possibly active fragments of key multidomain serine proteases of the complement system.

Also, in lack of a reliable and effective system for the recombinant preparation of fragments of complement serine proteases associated with recognition molecules of the complement system mutation studies and genetic engineering of them were difficult and the outcome was difficult to interpret.

Last but not least methods of the art for producing MASP proteins and fragments were relatively expensive and cumbersome: cheaper and more effective methods were needed.

There have been many attempts in the art to prepare recombinant MASP-1 and MASP-2. However, recombinant expression of the full-length MASPs provided serious difficulties. In WO 02/6460 (Jensenius and Thiel, 2002) cloning and sequencing of MASP-2 is described. However, the protein was not recombinantly prepared. Vorup-Jensen et al. transiently expressed human MASPs in HEK293 cells, but their recombinant MASP-1 had unexpected molecular mass and showed no enzymatic activity (Vorup-Jensen, 2000). Though Vorup-Jensen et al. succeeded in preparing an active MASP-2 protein, this protein carried a His tag. Moreover, the preparation process was prolonged and complicated. Chen et. al. tried to produce rat MASP-1 and MASP-2 in CHO cells, but the wild type proteases were cytotoxic to the cells and therefore only inactive mutants could be produced (Chen, 2001). Rossi et. al. expressed full-length human MASP-1 and MASP-2 in a baculovirus insect cell system, but due to the very low yield the proteases could not be purified to homogeneity (Rossi, 2001).

Rossi et al. (2001) expressed also CCP1-CCP2-SP fragments of MASP-1 and MASP-2 in a baculovirus insect cell system, which showed comparable enzymatic activities with the full-length molecules towards protein and ester substrates. Said fragments were secreted by the insect cells. However, CCP-SP fragment of MASP-2 could not be successfully produced in the baculovirus expression system (Rossi et al., 2001). Based on these results the authors concluded that the first CCP domain (CCP1) is crucial for activity and propose that the smallest active fragment of MASP proteins is the CCP1-CCP2-SP fragment. Moreover, expression in a baculovirus/insect cell system has obviously several disadvantages from the economic point of view that is relatively low yield, high costs and the complexity of purification process. Moreover proteins secreted from the insect cells are subject to a possible protease attack.

Previously, the baculovirus-insect cell system was used to produce recombinant C1r and C1s and their fragments (14, 20, 21). The yield of the secreted recombinant proteins, however, was found to be low. The catalytic C-terminal γB fragment of C1r, consisting of the two CCP domains followed by the activation peptide of the protease and the serine protease domain (B-chain), can be obtained by autolysis or by limited proteolysis of extrinsic proteases (e.g. thermolysin) (6). However, no recombinant production of the γB fragment of C1r or C1s had been disclosed before creation of the present invention. Also, no smaller recombinant fragments of the C1r or C1s catalytic region had been disclosed. In particular, no prokaryotic expression of C1r or C1s fragments had been suggested in the art.

To circumvent the problems of the art outlined above the present inventors decided to attempt recombinant expression of the catalytic fragments of multidomain serine proteases capable of binding to recognition molecules of the complement cascade. In spite of the fact that these are complex, multidomain proteins which are of mammalian origin, inventors decided to choose a prokaryotic, in particular a bacterial system, more particularly an *E. coli* based system.

To the best of their knowledge, the present Inventors were the first to express and successfully refold multidomain serine proteases in bacterial hosts.

It has long been accepted in the art that the proteolytic γB fragments of C1r and C1s, which consist of three domains: two CCP modules and the serine protease domain, retain the catalytic activity of the entire molecule both in terms of substrate specificity and catalytic efficiency (Villiers, 1985/Arlaud, 1986/Lacroix, 1989). Recent studies with recombinant fragments of C1r and C1s reinforced this view (Rossi, 1998/Lacroix, 2001). Since the MASP proteases share the same domain organization with C1r and C1s, it seems plausible that the CCP1-CCP2-SP fragments mediate the catalytic activity of these enzymes, as well. This is supported by the recent studies of Rossi et al. who showed comparable enzymatic activities with the full-length molecules towards protein and ester substrates and found that CCP1 domain is necessary to activity.

Applying a bacterial expression system, it is an object of the invention to produce functionally active fragments of MASP-1, MASP-2, MASP-3, C1s and C1r, with a yield sufficient for structural and functional characterization, as well as to provide a teaching to prepare the corresponding fragments of C1s and MASP-3. Furthermore, a further object of the invention is to create fragments from which the CCP domains preceding the SP domain were successively deleted and to create the respective expression vectors. It is a further object of the invention to functionally characterize the fragments.

Though in some bacterial systems, mainly in those providing low expression levels, the proteins could be expressed in a soluble form, overexpression systems are advantageous. A usual problem of overexpressing mammalian proteins in bacterial hosts is that the unfolded foreign protein forms inclusion bodies and has to be subjected to renaturation, though this feature may turn out to be an advantage: the expressed proteins are protected against protease attack. Despite a great number of proteins successfully renatured, protein refolding remains a problem to be solved on a case-by-case basis [Rudolph and Lilie, (1996)]. It is to be mentioned here that, as a matter of course, successful attempts are published and failures usually not. Nevertheless, even in the recent past protein refolding was considered as an extremely difficult task. By now it is generally approved that whereas in vitro refolding of single domain proteins is likely to be successful, refolding of multidomain proteins remains a problem the solution of which is far from being obvious (Fischer et al EPA 0 393 725 A1, Ambrosius et al., EPA 0 500 108). Furthermore, it is also well-known that protein folding is usually started at the N-terminal of the polypeptide chain. Therefore, if an N-terminal part of a protein is deleted, its refolding is significantly encumbered. Moreover, to the best of Inventors' knowledge, multidomain serine proteases, in particular of human origin, have not been prepared in a folded form in a prokaryotic expression system.

Being aware of the fact that larger molecules are more difficult to be refolded, but hoping that the presence of the N-terminal portion of the molecule may help inducing the folding process, Inventors attempted to renature the entire MASP molecules. After the failure of methods at hand, Inventors used a variety of additives and removed them in a stepwise manner which, of course, raises costs. In spite of this, no unambiguously positive results were obtained.

Surprisingly, inventors found that the C-terminal CCP1-CCP2-SP fragments (also named as γB-fragment after the nomenclature used for C1s and C1r proteins) of MASP proteins and of C1r and C1s proteins could be renatured with an improved renaturation method at a sufficient or, under preferred conditions, at a high yield.

Applying this method for smaller fragments success or promising results were achieved. In view of former results of their own and of those of Rossi et al (2001) it is also surprising that inventors found the MASP-2 CCP2-SP and the SP fragments to be active.

The inventors also recognized that a particularly improved method can be carried out if a temperature below 10° C. and a pH above pH 8.7, preferably above pH 9 or 10, is applied and, preferably, in the refolding buffer at least arginine is applied as a chaotropic agent.

In a similar expression system and renaturation method (which was slightly modified by applying higher temperature and a lower pH) inventors could express and isolate recombinant fragments of C1r as well.

Having now large amounts of pure fragments available, Inventors could provide a detailed functional characterization of the proteins. In particular, Inventors found differences in substrate and inhibitor specifities of MASP-1 and MASP-2, providing a basis for differentially measuring their level in serum or in a biological sample.

The fragments obtained according to the invention can be used advantageously e.g. in drug screening methods and for antibody production. Results also suggest possible applicability of them, in particular MASP-1, and of their inhibitors in medical treatments.

BRIEF DESCRIPTION OF THE INVENTION

Methods

The invention relates to a recombinant method for the preparation of an unglycosylated folded C-terminal fragment of a multidomain serine protease, comprising the following steps:

a bacterial expression vector for expressing a DNA insert encoding a C-terminal fragment of a multidomain serine protease is provided, said protein fragment is produced in a bacterial host by using the said vector and obtained in a folded form from the bacterial host.

Preferably, the multidomain serine protease encoded by the cDNA insert is a multidomain serine protease of the complement cascade (multidomain complement serine protease), wherein said serine protease is of vertebrata, preferably mammalian, more preferably human origin.

Preferably, the multidomain serine protease comprises at least two CCP domains and a serine protease domain, preferably in the following order: CCP1-CCP2-SP (which is the same domain structure as e.g. that of the γB-fragment of e.g. the C1r molecule).

More preferably a multidomain serine protease having the following domain structure CUB-EGF-CUB-CCP1-CCP2-SP and being capable of binding to a recognition molecule of the complement pathway, e.g. to MBL or C1q. Preferably, the multidomain serine protease is selected from the following: MASP-1, MASP-2, MASP-3, C1r and C1q.

Preferably, the multidomain serine protease C-terminal fragment encoded by the cDNA insert is a fragment of comprising one or more domain selected from the following domain types: CCP1, CCP2, SP, More preferably, the C-terminal fragment has essentially a domain structure of any of the following: CCP1-CCP2-SP, CCP2-SP, SP.

The C-terminal fragment is preferably selected from any of the following: MASP-1 CCP1-CCP2-SP fragment, MASP-2 CCP1-CCP2-SP fragment, MASP-2 CCP2-SP fragment or MASP-2 SP fragment, MASP-3 CCP1-CCP2-SP fragment, MASP-3 CCP2-SP fragment or MASP-3 SP fragment, C1r CCP1-CCP2-SP fragment (i.e. γB-fragment), C1r CCP2-SP fragment or C1r SP fragment, C1s CCP1-CCP2-SP fragment (i.e. γB-fragment), C1s CCP2-SP fragment or C1s SP fragment.

As will be understood, the fragments of the invention may comprise not only "whole" domains but also parts of domains provided that the fragment comprises at least one domain which is in the folded form. Preferably, the fragments of the invention comprise only folded domains besides of course, if desired, further useful sequences, e.g. tag sequences, as detailed below.

In a preferred embodiment the fragment of the invention comprises on its N-terminal a tag sequence the coding sequence of which increases the efficiency of bacterial protein expression.

Said tag sequence is expediently a sequence suitable for the promoter used for expression, preferably a T7-tag sequence comprising preferably 3 or 4 amine acids, preferably of the sequence: Ala-Ser-Met-(Thr). SEQ ID NO:19, SEQ ID NO:20.

The fragment of the invention may also lack on its N-terminal a tag sequence the coding sequence of which increases the efficiency of bacterial protein expression due to a proteolytic cleavage (e.g. autolytic cleavage), e.g. it is a MASP-2 CCP1-CCP2-SP fragment starting with $Ile^{291}$ at its N-terminus.

In a further preferred embodiment said fragment comprises mutation.

In a preferred embodiment the bacterial host is *E. coli* and the expression vector is a vector capable of expressing, preferably overexpressing foreign genes in *E. coli*.

In a highly preferred embodiment *E. coli* BL21 strain is used, the promoter is a T7 promoter, and the vector is a pET vector or a pSE-420 vector.

In overexpression systems the expressed foreign proteins most often form inclusion bodies. Nevertheless, an embodiment wherein the protein fragments are expressed in a soluble form is also within the claimed scope of the invention.

Preferably, the step of obtaining the C-terminal fragment in a folded form comprises the following steps:
i) the inclusion bodies formed in the bacterial host are isolated
ii) the protein fragment molecules are renatured from the inclusion bodies,
iii) optionally, the renatured protein fragment molecules are further purified.

Purification is carried out preferably by ion exchange chromatography, more preferably by a combination of anion and cation exchange chromatography. In this case preferably a higher than 70%, more preferably a higher than 80%, even more preferably a higher than 90% purity is achieved, as detectable by SDS-PAGE.

Refolding of MASP-Fragments

In a preferred embodiment the protein fragment is MASP-fragment, preferably any of the MASP-fragments as defined above.

M'm.3. For the preparation of MASP protein fragments, in the preparation method step c) above comprises the following steps:
i) solubilization of the inclusion bodies,
ii) diluting the solubilized protein fragments and transferring them into a refolding buffer,
iii) allowing the protein fragments to refold at
a pH higher than 7, preferably above pH 8.5, more preferably between 8.5 and 10.5 and
a temperature between 0 and 15° C.,
in an environment suitable for mildly oxidizing cysteine residues into cystines,
iv) transferring the refolded protein fragments into an appropriate buffer.

In step i) solubilization can be carried out in an appropriate solubilization agent, e.g. GuHCl or urea, preferably in a buffer comprising 6M GuHCl, any suitable reducing agent e.g. β-mercaptoethanol or DTT, e.g. 100 mM DTT, and optionally a buffering agent, e.g. 0.1 M Tris-HCl (pH 8.3), e.g. at room temperature or somewhat lower. In order to avoid oxidation of the reducing agents (in particular if DTT is used), long incubation periods should be avoided. The protein concentration in the solution is preferably 0.5 to 25 mg/ml, more preferably 1 to 20 or 2 to 10 mg/ml, even more preferably 3 to 7, e.g. about 5 mg/ml.

In step ii) the solubilized proteins are preferably diluted directly into the refolding buffer. The dilution is at least 10 fold, preferably at least 100 fold, more preferably 200-600 fold, even more preferably about 400 fold. The protein can be added dropwise or in relatively small portions.

Prior dilution the refolding buffer is cooled below 10° C., preferably below 5° C., more preferably to about 0° C. Preferably, the buffer is degassed before adding the solubilized protein.

In step iii), during refolding, the refolding buffer comprises a redox system, e.g. cysteine/cystine system or a glutathione system wherein the ratio of the reduced and oxidized forms is set to provide an mildly reductive environment, e.g. wherein the reduced/oxidized ratio is 10:1 to 1:1. Preferably, glutathione is used wherein the ratio of the reduced and oxidized forms is about 3 to 1, e.g. 3 mM and 1 mM, respectively.

The refolding buffer further comprises a chaotropic agent in an appropriate concentration, e.g. arginine (0.5 to 1.0 M). In case of MASP-2, GuHCl (0.5 to 2.0 M) can be used. A mixture of arginine and GuHCl is also applicable within the concentration ranges given above (preferably at most 3.0 M together), and being aware of this fact the skilled person will be able to set the appropriate ratio for each protein.

Refolding is carried out at a temperature between 0 to 15° C., preferably between 0 to 10° C., more preferably between 4 to 8° C. In a highly preferred embodiment the refolding is carried out at 6° C.

The protein fragments may refold very fast; nevertheless, they should be allowed to refold for a while to reduce the number of aggregates and misfolded molecules, e.g. at least a few minutes or preferably at least hours e.g. at least 2, 3 or 4 hours or overnight. The proteins may be allowed to refold for longer, e.g. one or two days or even more. Duration is limited by usual factors influencing limits of storage of protein solutions.

Preferably, the refolding buffer comprises a protease inhibitor, e.g. EDTA or one or more other known protease inhibitor and any appropriate buffering agent, e.g. 50 mM Tris.

Thus, in a preferred embodiment of the method
i) solubilization is carried out in the presence of 5 to 6 M GuHCl in a suitable solubilization buffer,
ii) the solubilized proteins are diluted 200 to 600 fold into the refolding buffer previously cooled to a temperature between 0 to 10° C.,
iii) the refolding buffer comprises a chaotropic agent, preferably arginine; reduced and oxidized glutathiones in a ratio of 10:1 to 1:1; and preferably a buffering agent and one or more protease inhibitor(s); and refolding is carried out at a temperature between 0 to 10° C.

iv) the refolded proteins are dialyzed into a buffer of a pH above the pI of the protein fragment.

In a preferred embodiment the MASP protein fragment is MASP-1 CCP1-CCP2-SP fragment, MASP-2 CCP1-CCP2-SP fragment or MASP-2 CCP2-SP fragment and the pH of the refolding buffer is between pH 8.5 and 9.5, preferably about pH 9.0.

In a further preferred embodiment the MASP protein fragment is MASP-2 SP fragment and the pH is between pH 9.5 to 10.5, preferably pH 10.

In a further preferred embodiment the MASP protein fragment is MASP-2 fragment and in the refolding buffer the chaotropic agent is 0.5 to 2 M GuHCl or at least 0.5 M of a mixture of maximum 2 M GuHCl and maximum 1 M arginine.

Refolding of C1r Fragments

In a further preferred embodiment the protein fragment is C1 serine protease fragment, e.g. a C1s or a C1r fragment, preferably any of the C1r fragments as defined above.

Preferably, for the preparation of C1r protein fragments, in the preparation method step c) comprises the following steps:

i) solubilization of the inclusion bodies,
ii) diluting the solubilized protein fragments and transferring them into a refolding buffer,
iii) allowing the protein fragments to refold at
    a pH higher than 5, preferably between 7 and pH 8.5 and a temperature between 0 and 15° C.,
    in an environment suitable for mildly oxidizing cysteine residues into cystines
iv) transferring the refolded protein fragments into an appropriate buffer.

In step i) solubilization can be carried out in an appropriate solubilization agent, e.g. GuHCl or urea, preferably in a buffer comprising 6M GuHCl, any suitable reducing agent e.g. β-mercaptoethanol or DTT, e.g. 100 mM DTT, and optionally a buffering agent, e.g. 0.1 M Tris-HCl (pH 8.3), e.g. at room temperature or somewhat lower. In order to avoid oxidation of the reducing agents (in particular if DTT is used), long incubation periods should be avoided.

The protein concentration in the solution is preferably 0.5 to 25 mg/ml, more preferably 1 to 20 or 2 to 10 mg/ml, even more preferably 3 to 7, e.g. about 5 mg/ml.

In step ii) the solubilized proteins are preferably diluted directly into the refolding buffer. The dilution is at least 10 fold, preferably at least 100 fold, more preferably 200-600 fold, even more preferably about 400 fold. The protein can be added dropwise or in relatively small portions.

In step iii), during refolding, the refolding buffer comprises a redox system, e.g. cysteine/cystine system or a glutathione system wherein the ratio of the reduced and oxidized forms is set to provide an mildly reductive environment, e.g. wherein the reduced/oxidized ratio is 10:1 to 1:1. Preferably, glutathione is used wherein the ratio of the reduced and oxidized forms is about 3 to 1, e.g. 3 mM and 1 mM, respectively.

The refolding buffer further comprises a chaotropic agent in an appropriate concentration, preferably GuHCl (preferably 2.0 M).

Refolding is carried out at a temperature between 0 to 15° C., preferably between 4 to 15° C.

The protein fragments may refold very fast; nevertheless, they should be allowed to refold for a while to reduce the number of aggregates and misfolded molecules, e.g. at least a few minutes or preferably at least hours e.g. at least 2, 3 or 4 hours or overnight. The proteins may be allowed to refold for longer, e.g. one or two days or even more. Duration is limited by usual factors influencing limits of storage of protein solutions.

Preferably, the refolding buffer comprises a protease inhibitor, e.g. EDTA or one or more other known protease inhibitor and any appropriate buffering agent, e.g. 50 mM Tris.

Bacterial Expression Vectors

In a yet further aspect of the invention a prokaryotic expression vector is provided, said vector comprising a DNA insert encoding a C-terminal fragment of a multidomain serine protease and means for expressing said fragment in a bacterial host.

Preferably, the prokaryotic expression vector is a bacterial vector and said DNA insert is a cDNA insert.

Preferably, the cDNA insert encodes a fragment comprising one or more domain selected from the following domain types: CCP1, CCP2, SP.

Preferably, the said cDNA insert encodes a fragment of a multidomain serine protease of the complement cascade (multidomain complement serine protease), more preferably a multidomain serine protease capable of binding to a recognition molecule of the complement pathway, e.g. to MBL or C1q, preferably a multidomain serine protease selected from the following: MASP-1, MASP-2, MASP-3, C1r and C1q.

Preferably, the c-DNA insert encodes a protein fragment having essentially a domain structure of any of the following: CCP1-CCP2-SP, CCP2-SP, SP, Preferably, the C-terminal fragment is selected from any of the following: MASP-1 CCP 1-CCP2-SP fragment, MASP-2 CCP1-CCP2-SP fragment, MASP-2 CCP2-SP fragment or MASP-2 SP fragment, MASP-3 CCP1-CCP2-SP fragment, MASP-3 CCP2-SP fragment or MASP-3 SP fragment, C1r CCP1-CCP2-SP fragment (i.e. γB-fragment), C1r CCP2-SP fragment or C1r SP fragment, C1s CCP1-CCP2-SP fragment (i.e. βB-fragment), C1s CCP2-SP fragment or C1s SP fragment.

In a preferred embodiment, the cDNA insert comprises a sequence encoding a further amino acid sequence operably linked to the sequence encoding the protein fragment. Such further sequence can be e.g. a sequence increasing the efficiency of bacterial protein expression, or a sequence encoding a tag sequence, e.g. an N-terminal tag sequence.

Said tag sequence is expediently a sequence suitable for the promoter used for expression, preferably a T7-tag sequence comprising preferably 3 or 4 amino acids, preferably of the sequence: Ala-Ser-Met-(Thr). SEQ ID NO:19, SEQ ID NO:20.

In a further preferred embodiment said fragment comprises mutation.

Any vector as described above wherein the means for expressing the DNA insert sequence encoding any of the protein fragments as disclosed above, operably linked to a promoter, preferably an inducible overexpressing promoter capable of driving expression in a suitable bacterial host Preferably, the bacterial host is *E. coli*, more preferably an *E. coli* strain suitable for overexpression, e.g. the BL21 strain, and the promoter is a promoter driving overexpression, e.g. the T7 promoter. The vector advantageously is a multicopy vector carrying a selectable marker and a suitable cloning site, e.g. the vector is a pET vector or a pSE-420 vector.

Protein Fragments

In an aspect the invention relates to a C-terminal fragment of a multidomain serine protease of the complement cascade (multidomain complement serine protease), obtained by the method of any of M, wherein said fragment is unglycosylated and folded.

In a preferred embodiment, the multidomain serine protease is a serine protease capable of binding to a recognition molecule of the complement pathway, e.g. MBL or C1q.

The multidomain serine protease according to the invention is of vertebrata, preferably mammalian, more preferably human origin.

In an aspect the invention relates to an unglycosylated folded C-terminal fragment of a multidomain serine protease comprising at least two CCP domains and a serine protease domain, preferably in the following order: CCP1-CCP2-SP, which is the same domain structure as e.g. that of the γB-fragment of e.g. the C1r molecule. Preferably, the serine protease has the following domain structure CUB-EGF-CUB-CCP1-CCP2-SP.

Preferably, the multidomain serine protease is a MASP.

In a further embodiment, the multidomain serine protease is a serine protease of the C1 complex.

Preferably, the C-terminal fragment comprises one or more of any of the following domains: CCP1, CCP2, SP, more preferably has essentially a domain structure of any of the following: CCP1-CCP2-SP, CCP2-SP, SP.

Preferably, the C-terminal fragment is selected from any of the following: MASP-1 CCP1-CCP2-SP fragment, MASP-2 CCP1-CCP2-SP fragment, MASP-2 CCP2-SP fragment or MASP-2 SP fragment, MASP-3 CCP1-CCP2-SP fragment, MASP-3 CCP2-SP fragment or MASP-3 SP fragment, C1r CCP1-CCP2-SP fragment (i.e. γB-fragment), C1r CCP2-SP fragment or C1r SP fragment, C1s CCP1-CCP2-SP fragment (i.e. γB-fragment), C1s CCP2-SP fragment or C1s SP fragment.

As will be understood, the fragments of the invention may comprise not only "whole" domains but also parts of domains provided that the fragment comprises at least one domain which is in the folded form.

In an embodiment the fragment of the invention comprises an additional amino acid sequence.

In a preferred embodiment the fragment of the invention comprises on its N-terminal a tag sequence the coding sequence of which increases the efficiency of bacterial protein expression.

Said tag sequence is expediently a sequence suitable for the promoter used for expression, preferably a T7-tag sequence comprising preferably 3 or 4 amino acids, preferably of the sequence: Ala-Ser-Met-(Thr). SEQ ID NO:19, SEQ ID NO:20.

The fragment of the invention may also lack on its N-terminal a tag sequence the coding sequence of which increases the efficiency of bacterial protein expression due to a proteolytic cleavage (e.g. autolytic cleavage). For example, the fragment can be a MASP-2 CCP1-CCP2-SP fragment starting with Ile$^{291}$ at its N-terminus.

Any fragment, however, which carries an evidence of having been produced by a non-bacterial expression system is of course excluded from the scope of the invention. For example fragments having a secretion signal sequence, either mammalian or a signal sequence operable in insect cells, or a part thereof, or additional amino acids obviously used for linking the fragments of the multidomain serine protease to a such sequence are not claimed according to the invention. For example, MASP-2 CCP1-CCP2-SP fragments carrying such sequences are excluded. Fragments, which are glycosilated, are not covered by the present invention, as well.

In a further preferred embodiment said fragment of the invention is autoactivated or capable of being autoactivated.

In a further preferred embodiment said fragment comprises mutation.

The mutated fragment can be inactivated or can be incapable of autoactivating. Thereby said mutants are proof against autoactivation and autodegradation.

In a highly preferred embodiment the activation site of the SP-domain, e.g. the Arg-Ile bond of the activation site is mutated, preferably to Gln-Ile. It is preferred, if the mutants can be activated in a regulated way, e.g. by thermolysin.

According to a further possibility, the active Ser is mutated, e.g. to Gly, Ala, Thr, Val, etc., preferably to Ala.

As will be understood, any amino acid or a group of amino acids can be mutated in the fragments by using the expression and purification system of the invention. Furthermore, deletion mutants can be created, e.g. C-terminal deletion mutants which may be inactive, as well.

In a further aspect, the invention also relates to folded, functional MASP-2 CCP2-SP fragments and MASP-2 SP fragments.

Uses

In a further aspect of the invention the following uses are provided:

Use of any of the fragments of the invention for raising antibodies. Preferably, said antibodies are suitable for detecting folded multidomain complement serine proteases, e.g. folded MASP-1, MASP-2 or MASP-3, more preferably MASP-1 or MASP-2 or measuring folded MASP-1 or MASP-2 or MASP-3, more preferably MASP-1 or MASP-2 level in a biological sample.

Use of any of the fragments of the invention as a standard or a control in assessing the level or activity of a multidomain complement serine protease in a biological sample.

The level of a multidomain complement serine protease, a MASP, C1r or C1s, can be measured by a labeled monoclonal antibody. Many ways of this is known, e.g. ELISA, RIA, DELFIA etc. If the antibody is bound to an epitope on a CCP1, CCP2 or an SP domain, a suitable fragment of the said protease according to the invention can be used as a control or standard provided that said fragment comprises the domain carrying said epitope.

If activity of a multidomain complement serine protease is assayed in a biological sample on a substrate of said protease, e.g. a substrate obtained by screening according to the invention, in such an assay an appropriate fragment of said protease according to the invention can be used as a standard or a control.

Use of the fragments of the invention for screening substrates or inhibitors of MASP-1 or MASP-2 or MASP-3, more preferably MASP-1 or MASP-2. In a preferred embodiment oligopeptides are screened, e.g. peptides comprising Arg and/or Lys residue(s).

Suitable antibodies can inhibit binding of the fragment to their substrates. Such antibodies, preferably monoclonal antibodies can be prepared and then selected by screening according to the invention. Moreover, antibodies inhibiting dimerization of C1r molecules can be devised or prepared (raised and selected). Thereby the activation of the classical pathway could be inhibited selectively.

Thus, the invention also relates to antibodies prepared by using the protein fragments of the invention.

The fragments of the invention can be used to prepare composite protein molecules functioning as whole MASP molecules, provided that the lacking N-terminal fragment of the MASP in question, comprising the rest of domains or a part of them, is provided in a native form and bound to the C-terminal portion of a fragment according to the invention.

Thereby a tool for studying domain structure and the role of individual domains can be prepared.

Thus, the fragments of the invention can be used as research tools in a variety of fields related to complement research as demonstrated herein.

Furthermore, the invention relates to the use of any of the MASP-1 fragments of the invention for the preparation of a pharmaceutical composition for inducing blood coagulation and the use of an inhibitor of MASP-1 for reducing blood coagulation. Preferably, said inhibitor is α2M or C1-inhibitor.

Assay Methods

According to a further aspect the invention relates to the following assay methods:

An assay method for measuring the level of a multidomain complement serine protease in a biological sample, wherein the presence of said serine protease is quantitatively detected in the sample by a labeled monoclonal antibody and the obtained signal is compared with a signal obtained for a control sample comprising a respective complement protease fragment according the invention.

An assay method for measuring the activity of a multidomain complement serine protease in a biological sample, wherein the activity on a substrate of said protease is measured, e.g. a substrate obtained by screening according to the invention, and an appropriate fragment of said protease according to the invention is used as a standard or a control provided that it has the same specific activity as the respective protease or the ratio of the activities of the native protease and the fragment is known. Preferably, in this assay method a CCP1-CCP2-SP fragment of said protease is used.

An assay method for assessing MASP-1 and MASP-2 levels in a sample of biological origin, said method comprising
- monitoring C2 cleavage and C4 cleavage by MASP proteins in aliquots of the sample whereas, if desired, other complement pathways are blocked,
- considering C4 conversion as a result of MASP 2 activity and C2 conversion as a result of MASP-1 and MASP-2 activity together
- calculating MASP-1 and MASP-2 levels using either known specific activity values of said proteins or MASP-1 and MASP-2 CCP1-CCP2-SP fragments, respectively, as inner standards.

An assay method for assessing MASP-1 and MASP-2 levels in a sample of biological origin, said method comprising
- monitoring C2 cleavage in the sample and considering C2 conversion as a result of MASP-1 and MASP-2 activity together,
- adding a calculated amount of α2M to the sample to inhibit MASP-1 activity but leaving MASP-2 activity unchanged or changing it to a negligible or a calculable extent,
- monitoring C2 activity in the sample comprising α2M,
- calculating MASP-1 and MASP-2 levels using either known specific activity values of said proteins or MASP-1 and MASP-2 CCP1-CCP2-SP fragments, respectively, as inner standards.

Methods for blocking the classic and the alternative pathways of the complement cascade are known, see e.g. U.S. Pat. No. 6,297,024.

A diagnostic kit for carrying out any of the assay methods of the invention said kit comprising a fragment of the invention is also provided.

Treatment

The invention also relates to a method for inducing fibrin formation from fibrinogen or blood coagulation comprising adding any of the MASP-1 fragments to a sample or administering them to a subject.

The invention also relates to a method for treating patients deficient in MASP-1 or in need of MASP-1 by administering a MASP-1 CCP1-CCP2-SP fragment to the patient.

The invention further relates to a method of reducing the activity of a human MASP-1 serine protease, comprising contacting said MASP-1 with α2M in at least a stochiometrically significant quantity.

Moreover, the invention relates to a method for treatment of a patient in need of inhibiting complement activity, comprising administering any inhibitor of the respective complement pathway prepared or screened as described above. Preferably, the invention further relates to a method for treatment of a patient in need of inhibiting complement activity exerted through the lectin pathway, which rises in complement related diseases, said treatment comprising the administration of any inhibitor of the lectin complement pathway, preferably an inhibitor of MASP-2, prepared or screened as described above. Preferably, the treated condition is reperfusion injury.

Definitions and Abbreviations

A "multidomain complement serine protease" is understood herein as a multidomain serine protease of the complement system.

A "supramolecular complex initiating the complement cascade" is meant herein as a supramolecular protein complex capable of binding to activator structures and activate the corresponding pathway of the complement system. Such complexes e.g. are the MBL/MASP complex or the C1 complex.

A "recognition molecule of the complement system" is a molecule capable of binding to activator structures triggering the complement cascade. Such molecules are e.g. MBL and C1q which are parts of supramolecular complex initiating the complement cascade.

A "MASP molecule" is understood as an MBL-associated serine protease having a domain structure consisting of at least two complement control protein (CCP) and one serine protease (SP) domain or module. The domain structure of a MASP molecule is preferably the following: CUB-EGF-CUB-CCP1-CCP2-SP.

A "CCP domain" (complement control protein domain) is a domain of about 50 to 70, preferably about 60 amino acids having a compact hydrophobe core comprising at least 5 antiparallel β-sheets. A CCP domain comprises 4 conserved cystein residues which form disulfide bridges according to the following pattern: 1-3, 2-4.

An SP domain ("serine protease") of a multidomain complement serine protease, in particular a MASP, C1r or C1s is in general characterized by a chymotrypsin-like fold, i.e. which has two beta-barrel domains, and each of them contains 6 beta-sheets arranged as antiparallel sheets. The active site residues are far apart in the primary sequence but are brought together in a crevice.

The terms "module" and "domain" have the same meaning throughout the description. Domain boundaries of domains of multidomain complement serine proteases as mentioned herein are basically described in the Complement Factsbook [By Morley, B., Published By Academic Press, Inc., (2000)] which is incorporated herein by reference. Nevertheless, a protein fragment is considered herein as comprising an essentially whole domain if the polypeptide portion of said domain, which is at least essentially capable of folding to its 3 dimensional structure or comprises sufficient amino acids so as to have a definite 3 dimensional structure.

A protein "fragment" of a multidomain complement serine protease is meant herein as a portion of a polypeptide having a sequence homologous to the sequence of the corresponding portion of a known variant of said molecule, wherein the level of homology is at least 50%, preferably at least 60 or 70, even more preferably 80, 85, 90, 93, 95, 96, 97 or 98%.

The amino acid positions in protein fragments are numbered according to the numbering of the multidomain complement serine protease A C-terminal fragment of a multidomain complement serine protease is a fragment comprising essentially the C-terminal amino acid sequence of the said protease or a fragment the C-terminal amino acid of which is an amino acid the position of which, considering the numbering of the serine protease, is not farther then 50, preferably 40, 30, 20, 15 or highly preferably 10 or 5 amino acid positions from the original C-terminal position of the said multidomain complement serine protease.

A "folded fragment" of a multidomain complement serine protease, e.g. a serine protease of a supramolecular complex initiating the complement cascade, e.g. a MASP molecule, a C1r or a C1s molecule, is meant herein as a fragment comprising at least one domain, corresponding to a domain of a known MASP or C1r or a C1s molecule, said domain having essentially a native tertiary structure as detected by any method known to be suitable for that purpose in the art, e.g. SDS-PAGE, activity, or any method for detecting a function of the molecule, and spectroscopic methods e.g. fluorescence methods, CD-spectroscopy or protein crystallography. Preferably, all the domains in the folded fragment are folded. As a matter of course a folded fragment may contain peptide segments which constitute a part of another domain of the MASP molecule or additional sequences or amino acids (e.g. tags) provided that the above criteria are fulfilled.

The abbreviation α2M is for α-2-macroglobulin, whereas C1, C2, C3, C4 and C1i or C1 inhibitor are the usual abbreviations of components of the complement cascade.

Other abbreviations, terms and expressions are used herein as common in the art.

Sequences of human MASP as well as C1r and C1s proteins are well known in the art from various sources. Such sequences are given e.g. in the Entrez Protein database, e.g. at the following accession numbers:

MASP-1

NP_001870 (isoform 1)
NP_624302 (isoform 2)
XP_193834 (mouse)
NP_071593 (rat) etc

MASP-2

000187 (human, precursor)
NP_006601 (human, isoform 1))

MASP-3

AAN39851 (rat)
BAB69688 (mouse)

C1r

P00736 (human, precursor)
NP_001724 (human)

C1s

P09871 (human, precursor)
NP_659187 (mouse)

BRIEF DESCRIPTION OF THE FIGURES

FIG. 15. Zymographic detection of MASP-1 and MASP-2 on gelatine; photo of the PAGE gel. White band shows that MASP-1 has digested a considerable amount of gelatine whereas MASP-2, having a significantly narrower substrate specificity, has not.

DETAILED DESCRIPTION OF THE INVENTION

Figure 1:
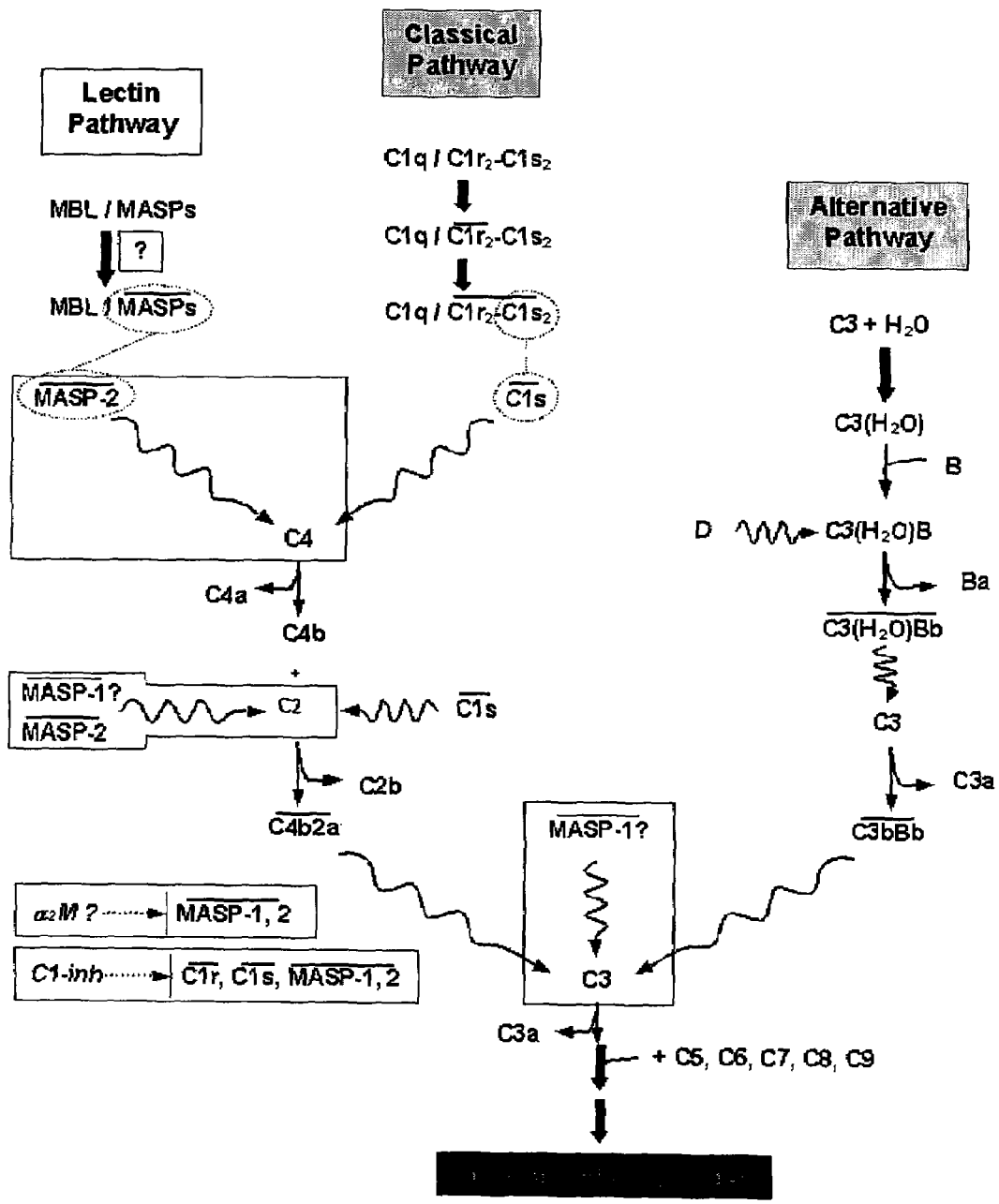
FIG. 1: A schematic representation of pathways of complement activation. Unclarified parts standing in the focus of the attention of the present study are indicated in light gray.
Figure 2:
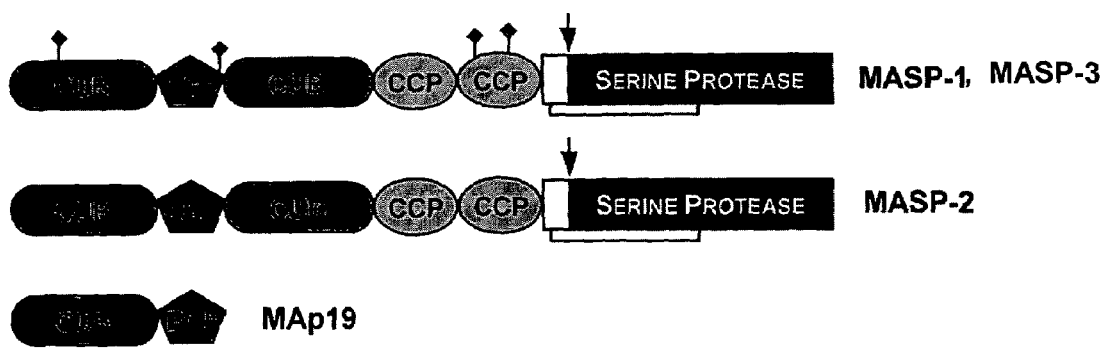
FIG. 2: Modular structure of proteins known to be associated with MBL. Five non-enzymatic domains can be found at the N-terminus of the MASPs and a serine protease domain at the C-terminus, which are cleaved upon activation.

Below the invention is further explained via specific examples. The skilled person will understand that many variations based on the same inventive idea can be carried out, said variations being therefore within the scope of the invention.

1. Materials and Methods

Construction of Recombinant Plasmids for the Expression of the MASP-1, MASP-2 and MASP-3 Fragments Coding sequences of MASP-1 and MASP-2 fragments were obtained by PCR starting from bacterial vectors comprising full length cDNAs of the human liver MASP proteins (the vectors were a kind gift of Dr. Schwable, W, Institut fur Hygiene, University of Innsbruck, Austria). The cDNAs are also available from human liver cDNA library and are disclosed e.g. by Takada F et al. (1993) and Sato T et al. (1994) (MASP-1, Swiss-Prot accession No: P48740) and by Thiel S et al. (1997) and Stover C. M. et al. (MASP-2, Swiss-Prot accession No: 000187).

For all recombinant constructs the pET-17b expression vector was digested with NheI and EcoRI restriction endonucleases and PCR products with identical sticky ends were ligated into the plasmid. In the case of the MASP-1 CCP1-CCP2-SP construct the following forward and reverse primers were used:
GCG
  GCTAGCATGACTGGTAATGAGTGCCCAGAGCTA,
  SEQ ID NO:1, AND
GCGGAATTCTCAGTTCCTCACTCCGGTGACCCT SEQ
  ID NO:2(the NheI and EcoRI restriction sites are underlined).

Preceding the MASP-1 sequence the forward primer contained the codon of four amino acids (Ala-Ser-Met-Thr) of the T7-Tag sequence, which increased the efficiency of the recombinant protein expression. As a result of this the N-terminus of the recombinant MASP-1 contained the four extra amino acids and the MASP-1 sequence began with Gly$^{298}$ and ended with Asn$^{699}$. The same strategy was followed upon constructing the MASP-2 fragments. The reverse primer for the three MASP-2 constructs was the same:
GCGGAATTCTTAAAAATCACTAATTATGTTCTCG,
  SEQ ID NO:3, therefore all recombinant fragment ended with Phe$^{686}$. The forward primers for MASP-2 CCP1-CCP2-SP, CCP2-SP and SP were:
GCG
  GCTAGCATGACTGGTTGGAAGATCCACTACACG,
  SEQ ID NO:4,
GCG
  GCTAGCATGACTATTGTTGACTGTGGCCCTCCTG
  SEQ ID NO:5and
GCG
  GCTAGCATGACTCCTGTTTGTGGACTATCAGCC,
  SEQ ID NO:6,respectively.

The recombinant CCP1-CCP2-SP construct contains the Ala-Ser-Met tripeptide before the Thr$^{287}$ amino acid of MASP-2 at the N-terminus. In the case of the CCP2-SP and SP fragments the Ala-Ser-Met-Thr extra tetrapeptide is followed by Ile$^{363}$ and Pro$^{432}$ of MASP-2, respectively.

For cloning MASP-3 only two new primer had to be designed, since its first five domains is identical with those of MASP-1 (i.e. only the serine-protease domain is different).

Reverse primer to MASP-3 SP domain:
GCGGAATTCTCACCGTTCCACCTGGGGCTCCAC
  SEQ ID NO:7

This primer comprises the EcoRI cleavage site to facilitate inserting the PCR-product into an expression vector. The recombinant proteins will thus end with a C-terminal Arg at position 728.

Forward primer to MASP-3 SP domain:
GCGGCTAGCATGACTCTTCCAGAGTGTG-
  GTCAGCCC SEQ ID NO:8

This primer comprises the NheI cleavage site, and the recombinant protein will start with the Lys at position 433, which is preceded by the usual Ala-Ser-Met-Thr sequence.

For CCP2-SP and CCP1-CCP2-SP construct the corresponding MASP-1 forward primers were used. In the PCR reaction human liver cDNA was used as a template. However, at a first attempt, no product was obtained irrespective of the primer pair used.

Thereafter a "nested PCR" method was attempted. Two new primer pairs were designed corresponding to somewhat farther sequence sections.

Forward:
CCTGTTCCATAGTGACAACTCGGGAGAGAA SEQ ID
  NO:9
Reverse:
GGGAGGCAGGCCCCGAGGAAGTAAGTCAGC SEQ ID
  NO:10

With these primers apparently appropriate products were obtained. This product was used then as a template for the original primers. In this case products of appropriate size were obtained as demonstrated on agarose gels.

Construction of Recombinant Plasmids for Expression of the C1r Fragments

The cDNA fragments corresponding to the amino acids 309-705 (CCP1-CCP2-SP), 376-705 (CCP2-SP) and 451-705 (SP) amino acids of human C1r were amplified by PCR using the proof reading Pfu DNA polymerase enzyme (Stratagene, La Jolla) and the full-length cDNA template (9). For the amplification procedure the following forward primers were obtained from East Port Scientific (Budapest, Hungary): 5'GCGAAGCTTGCCCCCAGCCCAAGACCCTA3', SEQ ID NO:11

5'GCGAAGCTTGTGGGCAGCCCCGAAACCTG3', SEQ ID NO:12
5'GCGAAGCTTGTGGGAAGCCCGTGAACC3' SEQ ID NO:13in the case of CCP1-CCP2-SP, CCP2-SP and SP, respectively. The reverse primer was 5'GCG GTCGACTCAGTCCTCCTCCTCCATCT3' for each fragment. The PCR products were digested with HindIII and SalI (cleavage sites are underlined) and were ligated into the HindIII/XhoI site of the pET-17b expression vector (Novagen, Madison) in frame with the following Tag sequence 5'ATGTGCACCCAAGCT3'SEQ ID NO:14. As a result of this the recombinant proteins contained four extra amino acids (Ser-Thr-Gln-Ala) at their N-terminus. The constructs were verified by DNA sequencing. In vitro mutagenesis experiments were carried out by means of the QuickChange site-directed mutagenesis kit (Stratagene, La Jolla, USA). The primer pairs (only the sense sequence is shown) were GTGGAACAGAGGCAGCA-GATAATCGGAGGGCAAAAAG SEQ ID NO:15for the Arg463Gln and GCCTGCCAGGGGGAT-GCTGGGGGCGTTTTTGCA SEQ ID NO:16for the Ser654Ala mutations.

Expression, Renaturation, and Purification of the Recombinant MASP Fragments

Expression

The expression plasmids were transformed into BL21 (DE3) pLysS host strain, and the transformants were selected on Luria-Bertani medium plates containing ampicillin and chloramphenicol. The expression was conducted according to the manufacturer's instructions (pET system manual, 1997). After induction with isopropyl-D-thiogalactoside, the cells were collected in a 1/10 volume Tris-EDTA buffer and frozen at −20° C. The cells were then thawed and incubated for 30 min at room temperature in the presence of 0.5% Nonidet P-40. The viscous solution was sonicated to shear the DNA, and the inclusion bodies were collected by centrifugation (12,000 g, 15 min, 4° C. The supernatant was discarded and the pellet was washed three times with Tris-EDTA buffer (1/10 of the culture volume).

Renaturation

The inclusion bodies were solubilized in 6 M GuHCl, 0.1 M Tris-HCl (pH 8.3), 100 mM DTT at room temperature. The solution contained ~10 mg/ml, or, in some cases 5 mg/ml protein. The solubilized proteins were diluted 400-fold into the refolding buffers. The refolding buffers contained 50 mM Tris-HCl, 3 mM reduced glutathione, 1 mM oxidized glutathione, 5 mM EDTA, and 0.5 M arginine. The pH of the solution was adjusted to pH 10.0 in the case of the MASP-2 SP fragment and to pH 9.0 otherwise. Before the addition of the glutation the solution was degassed and was cooled to 0° C. The renaturation process was conducted at 6° C. overnight. The renatured protein solutions were then dialyzed against 50 mM Tris-HCl (pH 9.0) and filtrated on a 0.45 µm nitrocellulose membrane.

Purification

The renatured proteins were purified on a Q-Sepharose-Fast Flow column (Amersham Biosciences). The samples were loaded onto the column and the elution was conducted with a linear NaCl gradient from 0 to 400 mM. Fractions were analyzed by SDS-PAGE. The recombinant proteins were further purified by cation exchange on Mono-S columns (Amersham Biosciences). The pH of the fractions containing the MASP-1 CCP1-CCP2-SP fragment and the MASP-2 SP fragment was adjusted to pH 5.0 and dialyzed against 50 mM AcOH (pH 5.0). The MASP-2 CCP-SP and MASP-2 CCP1-CCP-2-SP containing fractions were dialyzed against 20 mM Na-phosphate (pH 6.3). In each case a linear gradient of 0 to 600 mM NaCl was applied and the fractions containing the protein of interest were pooled. All proteins were judged to be >90% pure by SDS-PAGE. Individual protein fragments were dialyzed against 20 mM Tris, 140 mM NaCl, pH 7.4, aliquoted, frozen in liquid nitrogen and kept at −20° C. The concentration of the recombinant proteins was determined by measuring absorbance at 280 nm using the calculated absorption coefficients 18.7, 18.5, 19.1, and 14.9 (1%, 1 cm) for the MASP-2 CCP1-CCP2-SP, CCP2-SP, SP, and MASP-1 CCP1-CCP2-SP fragments, respectively. For calculation of the absorption coefficients we used the method of Gill et al. (ref.) taking disulfide bridges into account. The molecular masses calculated from the amino acid sequences were 44,017, 35,722, 28,164, and 45,478 Da for the MASP-2 CCP1-CCP2-SP, CCP2-SP, SP, and MASP-1 CCP1-CCP2-SP fragments, respectively.

Essentially the same way, MASP-3 fragments could be produced and refolded.

Expression, Renaturation, and Purification of the Recombinant C1r Fragments

Expression

The expression plasmids were transformed into the BL21 (DE3) pLysS host strain and the transformants were selected on LB plates containing ampicillin and chloramphenicol. The expression was carried out according to the manufacturer's instructions [pET System Manual, Novagen Inc. (10)]. After induction with IPTG the cells were collected in 1/10 volume TE buffer and freezed at −20° C. The cells were then thawed and incubated for 30 min at room temperature in the presence of 0.5% NP-40. The viscous solution was sonicated to shear the DNA, and the inclusion bodies were collected by centrifugation (12000 g, 15 min., 4° C.). The supernatant was discarded and the pellet was washed three times with TE buffer (1/10 of the culture volume).

Solubilization

The inclusion bodies were solubilized in 6 M GuHCl, 0.1 M Tris-HCl pH 8.3, 100 mM DTT for 3 h at room temperature. The solution contained approximately 10 mg/ml protein. The solubilized proteins were diluted to 400-fold into the refolding buffers. The refolding buffers contained 50 mM Tris-HCl pH 8.3, 3 mM GSH, 1 mM GSSG, 5 mM EDTA and 2 M GuHCI in the case of the CCP1-CCP2-SP fragment or 0.5 M arginine in the case of the CCP-SP and SP fragments. The renaturation process was carried out at 15° C. overnight. The renatured protein solutions were then dialyzed against 50 mM Tris-HCl pH 7.4, 145 mM NaCl, filtrated on a 0.45 µm nitrocellulose membrane and concentrated.

Purification

The renatured proteins were purified on Q-Sepharose-Fast Flow column (Pharmacia, Uppsala, Sweden). The samples were dialyzed against and the column was equilibrated in a buffer containing 20 mM NaCl and 20 mM Tris-HCl pH 8.3 for the CCP1-CCP2-SP and CCP2-SP or pH 7.4 for the SP fragments. The samples were loaded onto the column and the elution was carried out with a linear NaCl gradient from 20 mM to 400 mM. Fractions were identified by SDS-PAGE. The recombinant proteins were further purified by gel filtration using a Superose-12 FPLC column (Pharmacia, Uppsala, Sweden) in 50 mM NaCl, 20 mM Tris-HCl pH 8.3 for CCP1-CCP2-SP and CCP2-SP or pH 7.4 for SP. The concentration of the recombinant proteins was determined by absorbance at 280 mn using the absorption coefficients 15.2, 15.8, 15.4 (1%, 1 cm) for the CCP1-CCP2-SP, CCP2-SP, and SP fragments, respectively. For calculation of absorption coefficients we used the method of Gill et al. (11) taking disulfide bridges into account. The molecular masses calculated from the aminoacid sequences were 45532 Da, 37670 Da, and 28976 Da for CCP1-CCP2-SP, CCP2-SP, and SP fragments, respectively.

C1s fragments could be produced essentially the same way.

Purification of C2, Factor I, and Factor H

Human C2 was prepared by a recent immunoaffinity method (Laich and Sim, 2001). It was dialyzed against 20 mM HEPES, 140 mM NaCl, pH 7.4, and frozen in liquid nitrogen. Extinction coefficient (280 nm, 1%, 1 cm) was estimated from its amino acid sequence to be 9.4 for the 102 kDa protein.

Factors H and I were purified by the method of Sim et al. (1993). Extinction coefficients, $\epsilon$(280 nm, 1%, 1 cm), of 12.4 and 14.3, and molecular weights of 150 kDa and 88 kDa were used for Factors H and I, respectively (Pangburn and Muller-Eberhard, 1983).

Purification of C3 and C4

Human C4 was purified according to the method of Dodds (1993) with modifications. Briefly, fresh citrated plasma (15 ml) was made 1 mM Pefabloc-SC and 10 µg/ml soy bean trypsin inhibitor type I-S (SBTI-IS) [Sigma], then precipitated with 50 mM barium chloride for 1 h on ice. The supernatant was recovered by centrifugation and made 1 mM Pefabloc-SC and 5 mM EDTA. The plasma was then precipitated with 5% (w/v) polyethylene glycol (PEG 3350 molecular weight) [Sigma] for 30 min on ice, by adding 15% (w/v) PEG in Buffer A (20 mM Tris, 50 mM $\epsilon$-aminocaproic acid (EACA), 5 mM EDTA, 0.02% NaN$_3$, pH 7.4), and the supernatant recovered as before. A column of Q-Sepharose Fast Flow (16/10) [Amersham] was equilibrated in 95% Buffer A, 5% Buffer B (20 mM Tris, 50 mM $\epsilon$ACA, 5 mM EDTA, 0.02% NaN$_3$, 1 M NaCl, pH 7.4), and the supernatant was applied to the column. Proteins were eluted with a linear salt gradient. C3 eluted from the Q-Sepharose column in the second peak, in the 200-250 mM NaCl range, and fractions containing C3, as observed by SDS-PAGE, were pooled. The C3 pool was diluted with half a volume of water and made 1 mM Pefabloc-SC. A column of Mono-Q (HR 5/5) [Amersham] was equilibrated with 90% Buffer A, 10% Buffer B, and the dilute C3 pool was loaded and eluted with a linear gradient. C3 eluted as a single peak and was judged >90% pure by SDS-PAGE. It was also estimated to be >95% 'live' (i.e., its thiol ester was intact) by the presence of autocatalytic cleavage fragments of C3 $\alpha$-chain (Sim and Sim, 1981); and the lack of cleavage by Factor I in the presence of Factor H.

C4 eluted from the Q-Sepharose column in the final peak, and fractions containing C4, as observed by SDS-PAGE, were pooled. The C4 pool was diluted with half a volume of distilled water, loaded onto a Mono-Q FPLC column and eluted in a linear salt gradient. C4 was determined to be >80% pure by SDS-PAGE.

Live C3 and C4 were dialyzed against 20 mM HEPES, 140 mM NaCl, pH 7.4. Live C3 was used within three days, C4 was frozen in liquid nitrogen in 200 µl aliquots and kept at −80° C. for storage. Aliquots were thawed only once and then used within five days of thawing to ensure the proteins were active. Extinction coefficients, $\epsilon$(280 nm, 1%, 1 cm), of 9.7 and 8.3, and molecular weights of 185 kDa and 205 kDa were used for C3 and C4, respectively (Tack and Prahl, 1976; Nagasawa and Stroud, 1977).

Purification of C1-inh and Alpha-2-Macroglobulin

C1-inh was purified from human serum using protocols by Sim and Reboul (1981) and Pilatte et al (1989). Extinction coefficient, $\epsilon$(280 nm, 1%, 1 cm), of 3.6 and molecular weight of 71.1 kDa were used (Aulak et al, 1993).

Human alpha-2-macroglobulin ($\alpha_2$M) was isolated first as a by-product of the method for C3 and C4 purification (Dodds, 1993), then further purified according to Salvesen and Enghild (1993). Extinction coefficient, $\epsilon$(280 nm, 1%, 1 cm), of 9.0 and molecular weight of 720 kDa were used (Salvesen and Enghild, 1993).

Amidolysis of C3

The intact thiol ester bond in 'live' C3 was cleaved using ammonium salt as the nucleophile to obtain 'dead' C3(NH$_3$), according to Soames and Sim (1997) with modifications. C3 was incubated with a final concentration of 0.2 M ammonium hydrogen carbonate for 90 min at 37° C., making sure that the final pH of the reaction was above 8.0. At the end of the incubation, the reaction was collected with a brief centrifugation (5 min, 8000 g, RT) and dialyzed against 20 mM HEPES, 140 mM NaCl, pH 7.4.

N-Terminal Sequencing

After SDS-PAGE and blotting to polyvinylidene difluoride membrane, the N-terminal amino acid sequences of the recombinant proteins were determined by a pulsed-liquid phase protein sequencer ABI 471A.

Oligopeptide Substrate Library

The specificities of the MASP-1 and MASP-2 CCP1-CCP2-SP fragments were tested on a competing oligopeptide library applying the method described before (Antal, 2001).

Functional Studies with MASP-Fragments

C2, C3, C3(NH$_3$), C4 Cleavage

Serial dilutions of MASP-1 and MASP-2 fragments ranging between concentrations of 1 µM and 10 µM were incubated at 37° C. in 20 mM HEPES, 140 mM NaCl, pH 7.4 with C2, C3, C3(NH$_3$) or C4 at typical concentrations of 0.5-1 µM. The cleavage was followed by SDS-PAGE under reducing conditions. Desirable concentrations of the MASP fragments for further detailed kinetic analysis were chosen to be where half of the protein substrates were hydrolyzed during the first 20 minutes of incubation. The protein substrates C2, C3, C3(NH$_3$) or C4 were then incubated with the selected concentrations of the MASP fragments at 37° C. in 20 mM HEPES, 140 mM NaCl, pH 7.4. Typically 11-13 samples were taken at varying time periods but always within 50 minutes from the beginning of the reaction. Cleavages rates were quantified by measuring the diminution of the cleaved chain visualized by Coomassie stained SDS-PAGs using a GEL DOC 1000 instrument and Molecular Analyst Software for densitometric calculations (Bio-Rad, Hercules, Calif., USA). The reactions were assumed to be of the Michaelis-Menten type. In the case of C3 and C3(NH$_3$) cleavage a further reasonable assumption of KM>>[substrate] was made. The constants $K_M$, $k_{cat}$ and $K_M/k_{cat}$ were estimated by unbiased non-linear regression methods regressing the data on the following equations: $t=([S_0]-[S]+K_M\ln([S_0]/[S]))/(k_{cat}[E_0])$ or in the case of C3 and C3(NH$_3$) cleavage on $[S]=[S_0]\cdot\exp(-t\cdot[E_0]k_{cat}/K_M)$.

Reactivity Toward C1-Inhibitor and Alpha-2-Macroglobulin

Inhibition of the enzymatic activities of the MASP fragments by C1-inhibitor and alpha-2-macroglobulin were tested as follows. MASP-1 and MASP-2 fragments at concentrations selected in the C2, C3, C3(NH$_3$) and C4 cleavage tests were incubated at 37° C. with excess molar ratios of either C1-inhibitor, alpha-2-macroglobulin, or buffer in 20 mM HEPES, 140 mM NaCl, pH 7.4 for 40 minutes. Complement substrates C2, C3, C3(NH$_3$) or C4 were added at typical concentrations of 0.5-1 µM and the samples were further incubated for 20 minutes. The cleaved and uncleaved chains were visualized by reducing SDS-PAGE and the degree of inhibition was compared.

To assess the role of both C1-inhibitor and alpha-2-macroglobulin in the regulation of MASP-1 and MASP-2 the following experiment was devised. Each of the $^{125}$I-labeled MASP fragments was incubated with either C1-inhibitor or alpha-2-macroglobulin or both at physiological relative concentrations ([MASP-1]:[C1-inh]:[$\alpha_2$M]=1:30:60; [MASP-2]:[C1-inh]:[$\alpha_2$M]=1:90:180) at concentrations [MASP-1 CCP1-CCP2-SP]=9 nM, [MASP-2 fragments]=3, nM at 37° C. in 20 mM HEPES, 140 mM NaCl, pH 7.4 for 90 minutes. The samples were further incubated at 37° C. for 30 minutes, run on reducing SDS-PAGE and visualized by means of autoradiography. The following serum concentrations were used when calculating the relative concentrations: [MASP-1]=65 nM (Terai et al., 1997), [MASP-2]=22 nM (Hajela, 2002), [C1-inh]=2 µM (Terai et al., 1997) and [alpha-$_2$M]=4 µM.

To assess the rate of SDS stable complex formation between the MASP-1 and MASP-2 CCP1-CCP2-SP fragments and C1-inhibitor, the $^{125}$I-labelled MASP fragments at concentrations ranging between 30-100 nM were incubated with 100-350 nM C1-inhibitor at 37° C. in 20 mM HEPES, 140 mM NaCl, pH 7.4 for 40 minutes. Typically 11-13 samples were taken at varying time periods. The reactions were stopped with reducing sample buffer containing 0.125 M Tris, 4.8% SDS, 8 M urea 20% glycerol, 720 mM mercaptoethanol, 0.02% bromophenol blue, pH 6.8. The samples were further incubated at 37° C. for 30 minutes and run on reducing SDS-PAGE. Cleavages rates were visualized by means of autoradiography and the diminution of the reacted MASP chain was quantified using a GEL DOC 1000 instrument and Molecular Analyst Software for densitometric calculations (Bio-Rad, Hercules, Calif., USA). The kinetic constants were calculated assuming irreversible inhibition proceeded by reversible enzyme-inhibitor complex formation. Using steady-state approximation and neglecting the starting enzyme concentration compared to the starting inhibitor concentration ([$I_0$]>>[$E_0$]) the data was regressed on the following equation using non-linear regression methods: [E]=[$E_0$]·exp($-k_{obs}$·t); $k_{obs}=k_2 \cdot [I_0]/(K_i+[I_0])$, where $k_{obs}$ is the observed pseudo-first order rate of reaction, $k_2$ is the rate of irreversible enzyme-inhibitor complex formation and $K_i$ is the inhibitory constant.

Radioiodination and Autoradiography of MASP-Fragments

Radioiodination

The MASP-1 CCP 1-CCP2-SP, MASP-2 CCP 1-CCP2-SP, CCP2-SP and SP fragments were labeled with $^{125}$I using iodogen (1,3,4,6-tetrachloro-3$\alpha$,6$\alpha$-diphenylglycoluril) [Sigma] as the oxidising agent (Fraker and Speck, 1978). Eppendorf tubes (1.5 ml) were coated with 200 µl iodogen and excess iodogen was washed off with 0.5 ml 20 mM HEPES, 140 mM NaCl, 5 mM CaCl$_2$, pH 7.4 (HBS). Protein samples were transferred to the iodogen-coated tube and incubated with 10µl Na-$^{125}$I (1 mCi) [Amersham International, Aylesbury, UK] for 10-20 min on ice. Free 125-iodide was removed by desalting on a PD-10 Sephadex G-25 gel filtration column [Amersham] which was presaturated with 0.1% (v/v) Emulphogene BC720 [Sigma] in HBS. Radiolabelled protein fractions were pooled and stored at 4° C. Specific activity of a protein was determined by measuring on a Mini-Assay type 6-20 manual y counter [Mini Instruments, Burnham-on-Crouch, Essex, UK].

Autoradiography

Dried SDS-PAGE gels of $^{125}$I-labelled samples were exposed to X-ray film [Fuji RX, Fuji Photo Film UK Ltd, London] at -70° C. in autoradiography cassettes with intensifying screens. Films were developed using an X-Ograph imaging system Compact X4 [X-Ograph imaging system, Malmesbury, UK].

Enzymatic Assays with the C1r Fragments

Esterolytic Activity

The rates of hydrolysis were measured on the Z-Lys-S-Bzl, and Z-Gly-Arg-S-Bzl thioesters. The release rate of HS-Bzl was measured through its reaction with 4,4'-dithiodipyridine (12), and was followed with a Jasco V-550 spectrophotometer at a wavelength of 324 nm. Assays were carried out following the method of McRae et al. (13) at 30° C. in 20 mM Tris buffer at pH 7.5 containing 145 mM NaCl. $k_{cat}/K_M$ values were directly determined from the catalytic rate at low substrate concentrations (10-30 µM).

C1s Cleavage

Proenzyme C1s was expressed in baculovirus expression system using High Five insect cell culture. Functionally pure (80%) C1s proenzyme was obtained by purifying the cell culture supernatant on a DEAE Sepharose FF column (Amersham Pharmacia Biotech) as described in (14). C1s preserved its proenzyme state during the purification and storage. Proenzyme C1s cleavage ability of the C1r fragments were tested by means of the esterolytic activity of the generated active C1s molecules on the Z-Lys-S-Bzl thioester substrate. An enzyme/C1s molar ratio of 1:50 was used for most of the experiments. 10-15 ml C1s proenzyme solution with a protein concentration of ~0.1 µM in 20 mM Tris, 145 mM NaCl buffer pH 7.4 was thermostated at 30° C. The C1r SP, CCP2-SP and CCP1-CCP2-SP fragments were added to it at a final concentration of $1-3 \times 10^{-9}$ M. At 1 min intervals 1 ml of the mixture was withdrawn and the esterolytic activity was measured by the addition of the Z-Lys-S-Bzl substrate at a final concentration of 100 µM. The maximal specific activity value of totally activated C1s of 182 s$^{-1}$ at 100 µM Z-Lys-S-Bzl concentration was used for the calculation of the actual concentration of C1s. $k_{cat}/K_M$ values were calculated by linear fitting for the first 5-8 points where the amount of the cleaved, active C1s was less than 10% of the total proenzyme concentration.

C1r Autoactivation Experiments

The S654A mutant proenzyme SP, CCP2-SP, and CCP1-CCP2-SP fragments were used as substrates to investigate the autoactivation ability of the wild-type active C1r fragments. Measurements were carried out in 20 mM Tris, 145 mM NaCl buffer at pH 8.3. Reaction was started by the addition of the active enzyme to the S654A mutant proenzyme solution thermostated at 37° C. An enzyme:zymogen ratio of 1:10-1:50 was used. 10 µl aliquots were removed at 10-15 time points in the range of 0.5 min-1 h and added to 10 µl 5% SDS sample buffer (15) containing 5% mercaptoethanol and were immediately incubated for 3 min at 100° C. The cleavage at the activation site of the proenzyme molecules was followed by reducing SDS-PAGE. The acrylamide gels were stained with Coomassie brilliant blue. The concentration of the uncleaved proenzyme vs. time was calculated from the density of its bands recorded by a BioRad GelDoc2000 imaging system. After curve fitting and derivation in Origin 5.0 data analysing software (MicroCal Inc.) the cleavage rate vs. proenzyme concentration was calculated and proved to be linear in the concentration range used, therefore $k_{cat}/K_M$ values could be obtained from the slope of the curve.

Differential Scanning Calorimetry (DSC)

Calorimetric measurements were performed on a VP-DSC (Microcal Inc, Northampton, Mass.) differential scanning calorimeter. Denaturation curves were recorded between 10 and 80° C. at a pressure of 2.5 atm, using a scanning rate of 1° C./min. The protein concentration was set to 0.1 mg/ml. Samples were dialyzed against 20 mM Tris pH 8.3 145 mM NaCl, and the dialysis buffer was used as a reference. Heat capacities were calculated as outlined by Privalov (16).

Zymography

Protocols for gelatine zymography are described e.g. in (Kleiner at al. 1994) and in (Liota, 1990) which are incorporated herein by reference.

2. Results Obtained with the MASP Fragments

Expression, Purification and Characterization of the Recombinant MASP Fragments

Figure 3:
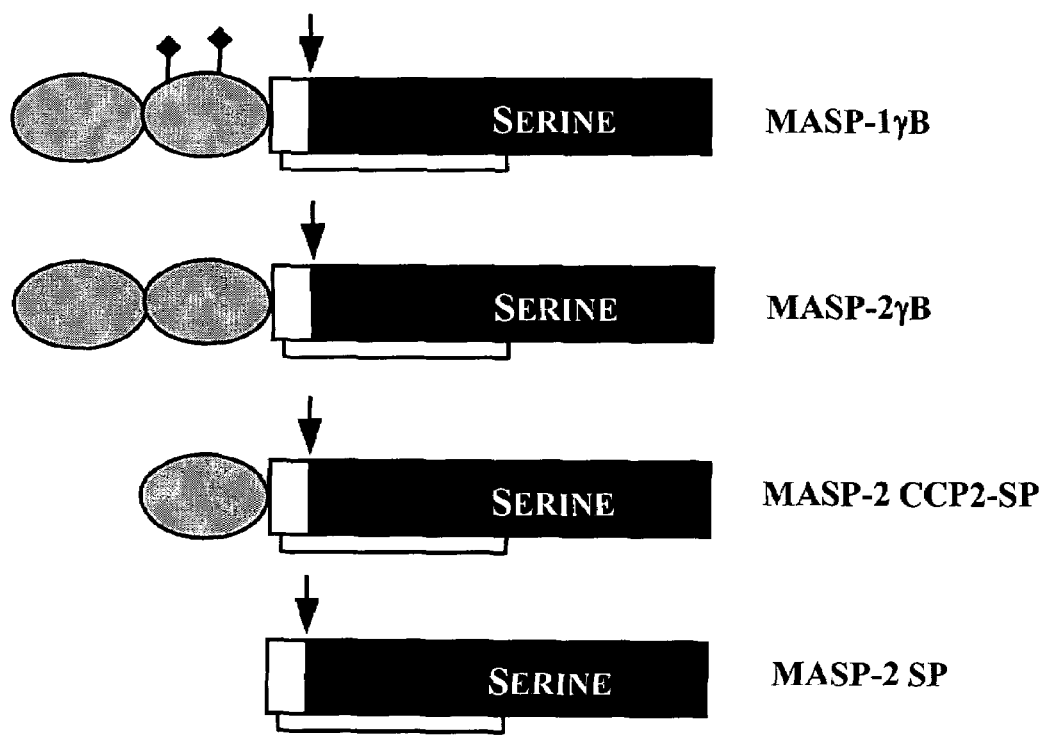
FIG. 3: Expression of the MASP-1 and MASP-2 fragments. Expression was carried out as described in the Materials and Methods section.
Figure 4:
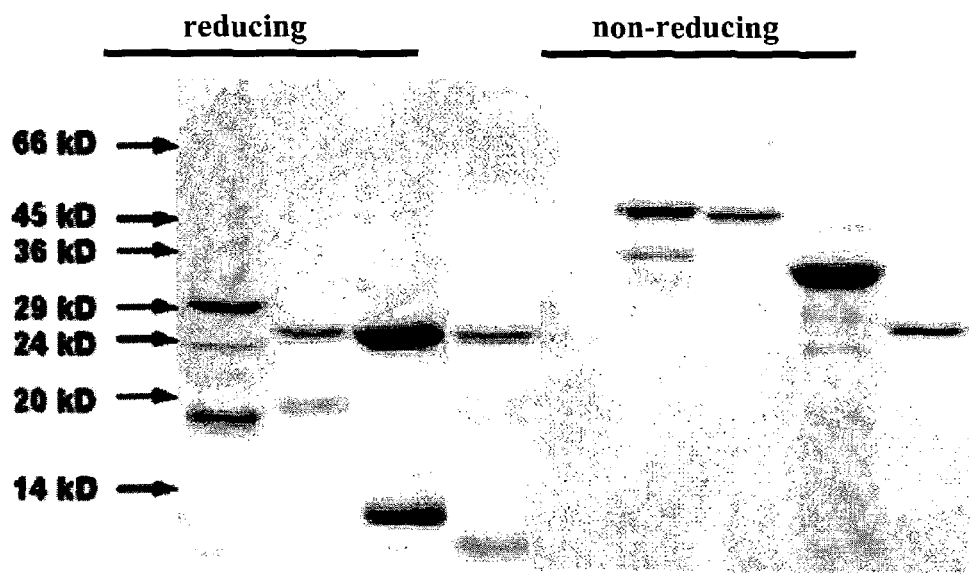
FIG. 4: Coomassie stained SDS-PAGE of the purified MASP-1 and MASP-2 fragments (MASP-1γB, MASP-2γB, MASP-2 CCP2-SP, MASP-2 SP). Following renaturation the fragments were purified using ion exchange and hydrophobic interaction chromatographies on Mono-S, Mono-Q and HIC PE columns. The MASP-2 fragments became activated during the purification process indicating the capability to autoactivate. MASP-1γB was fully activated before the chromatography steps and co-purified with a major contaminant. N-terminal amino acid sequencing yielded the expected sequences.

The catalytic region of MASP-1 and MASP-2, consisting of the two complement control protein modules and the serine protease domain (CCP1-CCP2-SP) (FIG. 3) was expresses in E. coli BL-21 cells using the pET-17b expression vector. In the case of MASP-2, truncated fragments of the catalytic region (the serine protease domain with one CCP module and the serine protease domain alone) (FIG. 3) were also expressed in the same expression system. Since the recombinant proteins accumulated as inclusion bodies inside the bacterial cells, renaturation procedures were needed to restore the native, folded structure (see Materials and Methods). The renatured recombinant proteins were purified by ion exchange chromatography on Q-Sepharose Fast Flow and Mono-S columns. The renaturation and the purification procedures were followed by SDS-PAGE and the purified proteins were subjected to N-terminal sequencing. Before renaturation the inclusion body proteins yielded single bands on the reducing SDS-PAGE corresponding to the zymogen form of the enzymes. After renaturation the MASP-1 CCP1-CCP2-SP fragment was fully activated and yielded two major bands under reducing conditions, which corresponded to the two-chain-structure obtained by the cleavage of the activation site $Arg^{448}$-$Ile^{449}$ bond, as determined by sequencing. The MASP-1 CCP1-CCP2-SP fragment co-purified with a minor contaminant, which migrated on SSD-PAGE as a band of 24 kDa under reducing and at 39 kDa under non-reducing conditions. N-terminal sequencing revealed that this fragment is a degraded form of the MASP-1 catalytic region lacking a 6 kDa fragment from its serine protease domain. The cleavage occurred at the $Arg^{504}$-$Asp^{505}$ bond removing the histidine from the catalytic triad and thus causing the loss of its enzymatic activity. The MASP-2 fragments migrated as single chain structures under reducing conditions throughout the renaturation procedure, however, they became activated during the purification process. Sequencing analysis confirmed the activation of the MASP-2 fragments to occur through the cleavage of the $Arg^{444}$-$Ile^{445}$ bond and further modifications were observed in the case of the MASP-2 CCP1-CCP2-SP fragment, which displayed $Ile^{291}$ at its N-terminus. This indicated that the bond between $Lys^{290}$-$Ile^{291}$ was cleaved and a heptapeptide (Ala-Ser-Met-Thr-Gly-Trp-Lys SEQ ID NO:17) was completely removed. This cleavage, however, does not compromise the integrity of the MASP-2 CCP1-CCP2-SP construct, since for technical reasons the original N-terminus contained three extra amino acids (Ala-Ser-Met of the T7-Tag) and the CUB2-CCP1 junction is at $His^{292}$-$Tyr^{293}$. The yield of proteins produced in the form of inclusion bodies in the cell culture was judged to be between 10-40 mg/l prior to renaturation. The overall yield pertaining to the amount of purified proteins recovered from one liter of cell culture ranged between 0.1-0.5 mg/l. A shift in pH to below pH 8.5 (8.3) resulted in at least a 3 times decrease in yield, in some cases (e.g. MASP-2 SP fragment) more or no yield at all.

Mutant Constructs

The expression and purification system of the invention proved to be very useful to prepare mutant MASP-fragments. Up to the present four constructs encoding mutant CCP1-CCP2-SP fragments are prepared. In the MASP-1 and MASP-2 CCP1-CCP2-SP fragments the activation site $Arg^{448}$-$Ile^{449}$ and $Arg^{444}$-$Ile^{445}$ bonds were mutated to $Gln^{448}$-$Ile^{449}$ (R448Q) and $Gln^{444}$-$Ile^{445}$ (R444Q) respectively. The latter mutant fragment was expressed and purified to homogeneity using the method as described above. About 1 mg of protein was obtained, which was not autoactivated but could be activated by lysosyme.

In the other two mutant constructs the codons of the active site serines were changed to codons of alanine: MASP-1 S(646)A and MASP-2 S(633)A mutants.

Proteolytic Activity of MASP-1 on Complement Components

Figure 5:
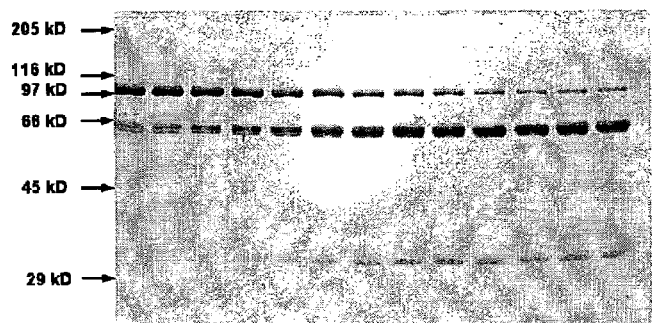
FIG. 5: C2, live C3, dead C3, C4 cleavage activities of the MASP-1 and MASP-2 fragments. Purified fragments were incubated with purified C2 (A), live C3, C3($NH_3$) (B) and C4 (C) for 0 to 40 minutes. Sample aliquots were taken to monitor the reaction. The samples were run on SDS-PAGE and the decrease of the cleavable chains was analyzed densitometrically. Upon preincubation of the MASP fragments with C1-inhibitor no cleavages could be observed.
Figure 5:
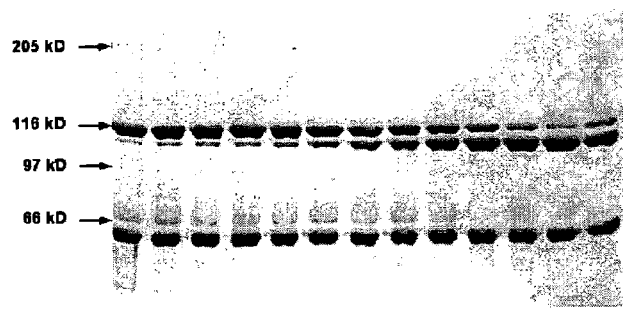
Figure 5:
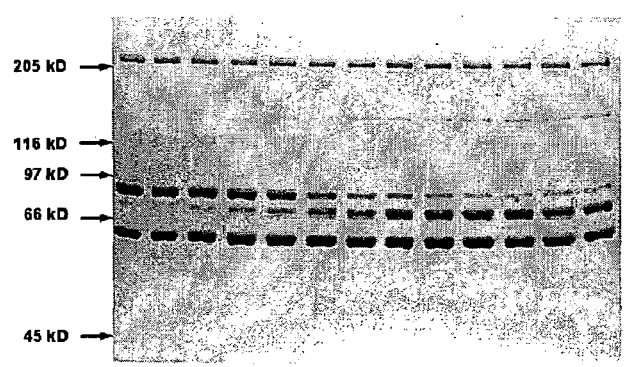
Figure 6:
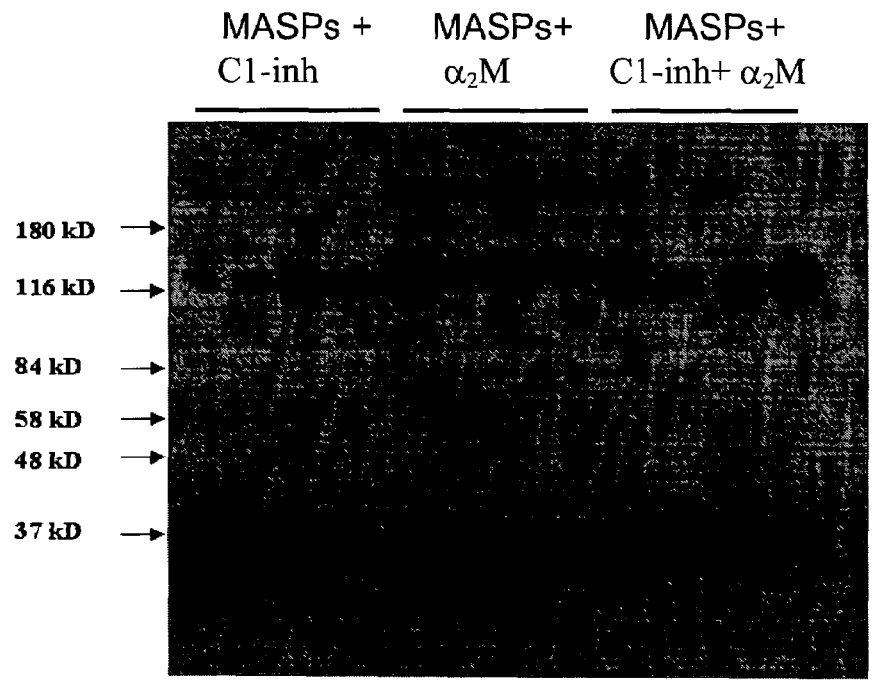
FIG. 6: Radiogram of an SDS-PAGE run under reducing conditions of the indicated inhibitors with the MASP-1 and MASP-2 fragments (MASP-1γB, MASP-2γB, MASP-2 CCP2-SP, MASP-2 SP)

The proteolytic activity of the MASP-1 catalytic fragment (CCP1-CCP2-SP) was investigated on protein substrates that are involved in the formation of the C3 and C5 convertase enzyme complexes of the classical and lectin pathways (i.e. on C2, C4, and C3). To resolve the controversy about the C3 cleaving ability of MASP-1 both 'live' and 'dead' C3 was used in the assays. 'Live' C3 (i.e. C3 with an intact thiol ester bond) was isolated from fresh human serum and used within three days in the measurements. It was rigorously tested before the proteolytic measurements by co-treating it with Factor I and Factor H and was found >95% 'live'. To test the proteolytic activity of MASP-1 on 'dead' C3 (i.e. on C3 with a cleaved thiol ester bond), a batch of the C3 preparation was inactivated using ammonia as the small nucleophile leading to $C3(NH_3)$ formation, The characteristic $k_{cat}/K_M$ values show that the MASP-1 CCP1-CCP2-SP fragment cleaves 'dead' C3 with a low but significant efficiency, whereas its proteolytic action on 'live' C3 is about 20 fold less (Table 1, FIG. 5.B). Nevertheless, it is important to note that in control experiments using the C1r CCP1-CCP2-SP fragment expressed in the same expression system as the MASP fragments (Kardos et al. 2001) we observed no cleavages of either 'live' or 'dead' C3. Our experiments demonstrated that complement component C4, similarly to 'live' C3, is basically resistant against the proteolytic activity of MASP-1 (Table 2, FIG. 5.C). C2, however, was digested by our MASP-1 fragment at a moderate rate (Table 2, FIG. 5.A). All cleavages could be inhibited by preincubating MASP-1 CCP1-CCP2-SP with a molar excess (1-3 fold) of either C1-inhibitor or alpha-2-macroglobulin (FIG. 6).

Proteolytic Activity of MASP-2 on Complement Components

The proteolytic activity of the MASP-2 CCP1-CCP2-SP fragment on C3 was very similar to that of the MASP-1 fragment. While MASP-2 CCP1-CCP2-SP had only a hardly detectable marginal activity on 'live' C3, it exhibited a low but significant enzymatic activity on 'dead' C3 (Table 1, FIG. 5.B). In contrast to the MASP-1 fragment the CCP1-CCP2-SP, CCP2-SP and SP fragments of MASP-2 cleaved C2 and C4 very efficiently (Table 2, FIGS. 5.A, C). The comparison of the three MASP-2 fragments shows that the serine protease domain of MASP-2 on its own can cleave C2 with high efficiency. The addition of the CCP modules to the SP domain somewhat decreases the proteolytic power in C2 cleavage. When C4 is used as a substrate, the MASP-2 fragments show a different picture. Although the serine protease domain on its own is capable of cleaving C4, the presence of the CCP2 domain significantly increases the efficiency of the catalysis (a 44-fold increase in the $k_{cat}/K_M$ value). The CCP1-CCP2-

SP fragment of MASP-2 is also very efficient in cleaving C4, although its proteolytic power is less than that of the CCP2-SP fragment. All cleavages could be abolished by preincubating the MASP-2 fragments with a molar excess (1-3 fold) of C1-inhibitor (FIG. 5) or with a large molar excess (40 fold) of alpha-2-macroglobulin (FIG. 6)

Figure 7:
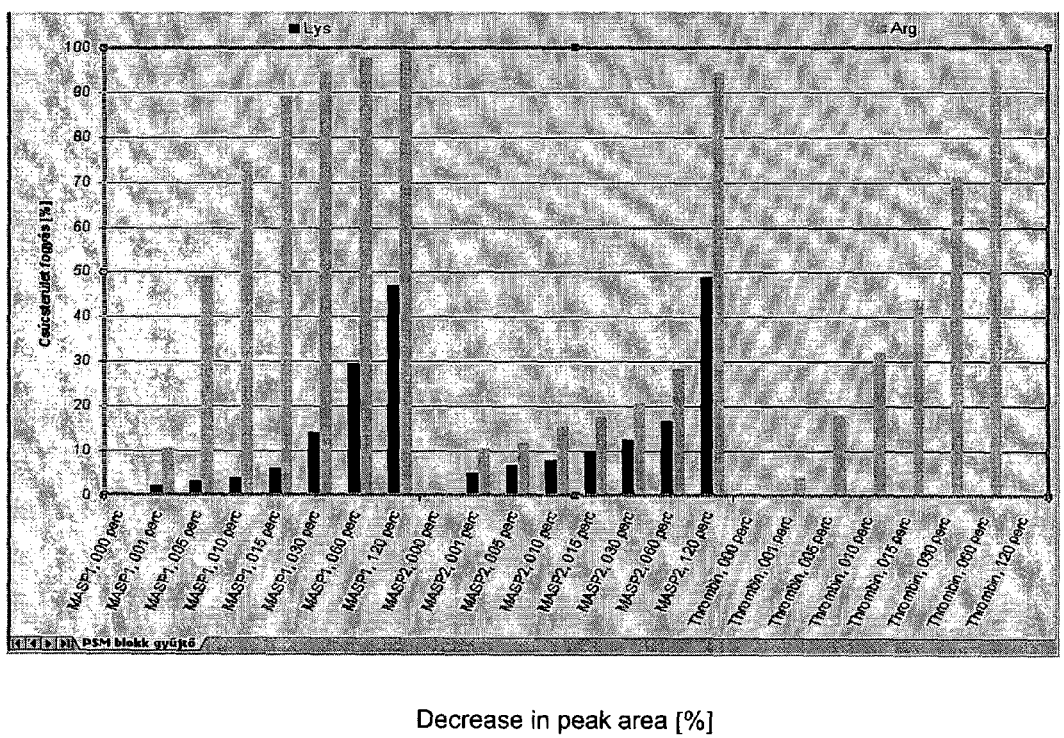
FIG. 7: The percentage of reacted peptides (% decrease of peak area, y-axis) of a given P1 site (Lys or Arg) during a time period given in minutes (x-axis). Peaks are normed.
Figure 8:
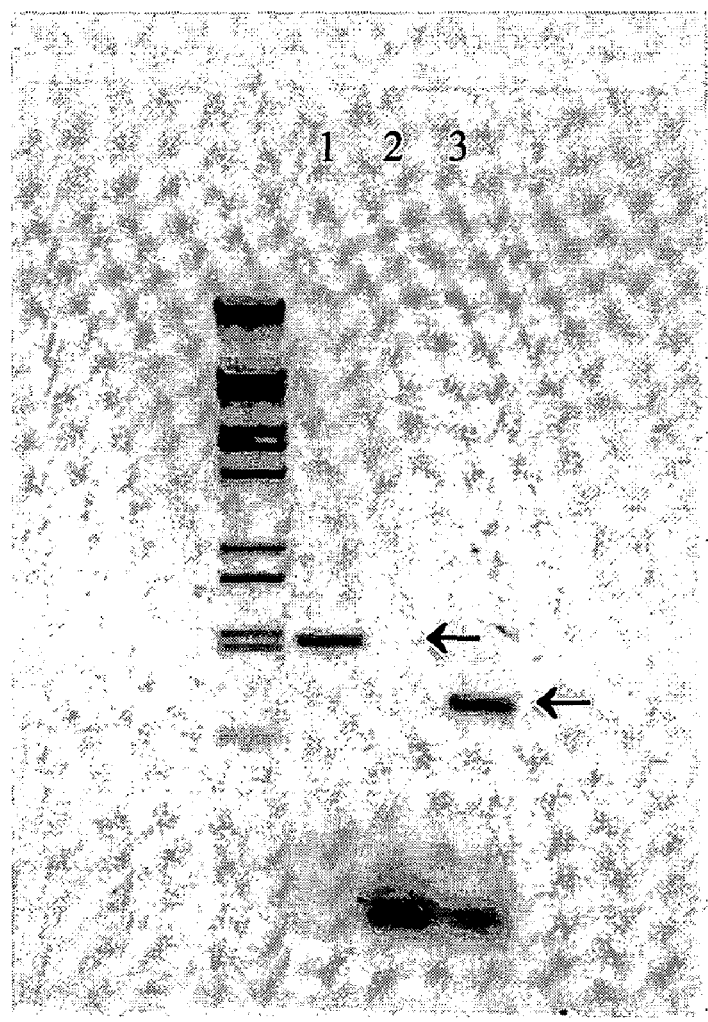
FIG. 8: Agarose gel of amplified MASP-3 fragment

Proteolytic Activities of the Catalytic Fragments of MASP-1 and MASP-2 on Oligopeptide Substrates To further investigate the range of substrate specificity and relative specific activities of MASP-1 and MASP-2 we applied a competing oligopeptide substrate library. (Antal, 2001). This library contains a mixture of seven oligopeptides (each 13 amino acids in length) with different cleavage sites (P1) for both trypsin and chymotrypsin-like enzymes (His-Ala-Ala-Pro-Xxx-Ser-Ala-Asp-Ile-Gln-Ile-Asp-Ile SEQ ID NO:18, where Xxx could be Lys, Arg, Tyr, Leu, Phe, Trp or Pro). The individual peptide substrates compete for the protease under investigation, in our cases for either the MASP-1 CCP1-CCP2-SP or the MASP-2 CCP1-CCP2-SP fragment. The results show that both enzymes cleave oligopeptides that contain either Arg or Lys at their P1 positions. The MASP-1 catalytic fragment (CCPA-CCPA-SP) exerted a substantially larger activity on the Arg oligopeptide substrate than the MASP-2 fragment (FIG. 7). Comparing the relative specific activities of the two fragments on the P1 Arg oligopeptide under the same conditions, at 15 min MASP-1 showed almost 90% digestion, whereas MASP-2 cleaved less than 20% of the substrate. This result substantiates that MASP-1 is a potent protease with significant catalytic strength. Another essential outcome of the competing oligopeptide substrate library experiments is that MASP-1 possesses extreme Arg selectivity at the P1 site of its substrate. This behavior strongly resembles that of thrombin, which exhibited similar Arg selectivity in the same competing oligopeptide library system (Antal, 2001). MASP-2 also preferred the Arg substrate to the Lys one, but the degree of preference was much less than that of MASP-1. A very similar specificity profile was obtained for trypsin in this oligopeptide library system.

Zymograpy provided an additional evidence that the substrate specificity of MASP-1 is significantly broader than that of MASP-2.

The Reaction of the MASP-1 and MASP-2 Fragments with C1-Inhibitor and Alpha-2-Macroglobulin As mentioned in the previous chapters, C1-inhibitor completely abolished the proteolytic activity of both MASP-1 and MASP-2 on all substrates. A marginal molar excess of C1-inhibitor over the enzyme concentration proved to be sufficient for full inhibition. Another inhibitor, alpha-2-macroglobulin (alpha-$_2$M), also inhibited the reactions, but exhibited lower efficiency toward MASP-2. The inefficient C3 cleavages could all be blocked by a small 1-3 fold molar excess over MASP-1 CCP1-CCP2-SP or MASP-2 CCP1-CCP2-SP, whereas only a 40-fold molar excess over the MASP-2 fragments was capable of significantly hindering C2 and C4 cleavage. The moderate cleavage of C2 by the MASP-1 CCP1-CCP2-SP fragment could be completely blocked by a small 1-3 fold molar excess of alpha-2-macroglobulin. To confirm the inhibition of the MASPs by $\alpha_2$M and to judge the relative rates of inhibition by $\alpha_2$M and C1-inhibitor the MASP fragments were labeled with $^{125}$I. The radiolabeled MASPs were then mixed with C1-inhibitor, $\alpha_2$M or both, in serum-like relative concentrations and the enzyme-inhibitor complexes were analyzed by SDS-PAGE followed by autoradiography (FIG. 6). Both C1-inhibitor and $\alpha_2$M formed SDS-PAGE stable complexes with all MASP fragments. In the case of the MASP-2 fragments C1-inhibitor proved to be the primary inhibitor, as it reacted faster with the MASP-2 fragments than the $\alpha_2$M, whereas in the case of MASP-1 alpha-$_2$M is the more probable physiological inhibitor. The observed pseudo first order rates of reaction ($k_{obs}$) with C1-inhibitor were 5-fold less for the MASP-1 CCP1-CCP2-SP than for the MASP-2 CCP1-CCP2-SP fragment. The $K_i$ values for the C1-inhibitor and MASP-2 CCP1-CCP2-SP reaction were in the nanomolar range (Table 3).

3. Results Obtained with the C1r Fragments

Expression and Renaturation of Recombinant Proteins

Figure 9:
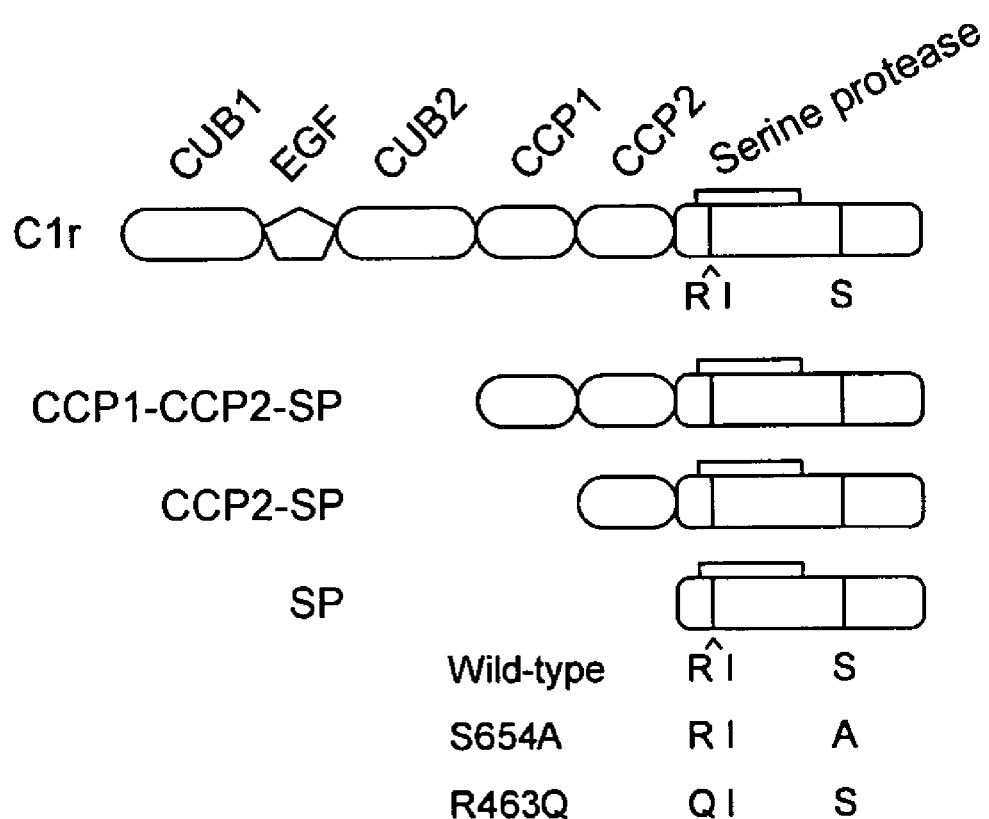
FIG. 9: Modular structure of human C1r Recombinant fragments of the catalytic region used in this study were CCP1-CCP2-SP, CCP2-SP, and SP. The γB fragment that can be obtained from the entire C1r molecule by limited proteolysis and our recombinant CCP1-CCP2-SP fragment have the same domain structure. The S654A catalytic site—and the R463Q activation site mutants are also presented.
Figure 10:
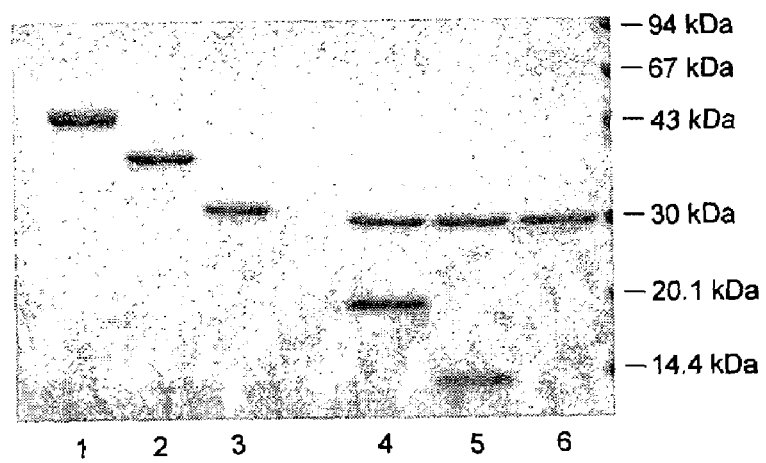
FIG. 10. SDS-PAGE of the renatured and purified C1r fragments A: Wild-type C1r fragments, non reducing conditions: (lane 1) CCP1-CCP2-SP, (lane 2) CCP2-SP, (lane 3) SP; reducing conditions: (lane 4) CCP1-CCP2-SP, (lane 5) CCP2-SP, (lane 6) SP. Proteins were analysed on a 12.5% polyacrylamide gel. The enzymes are fully activated after purification. B: R463Q mutant zymogen fragments and their thermolysin activated two-chain forms (10 U thermolysin/mg C1r fragment, 2 h, 30° C.), reducing conditions: (lane 1, 2) R463Q CCP1-CCP2-SP, (lane 3, 4) R463Q CCP2-SP, lane (5, 6) R463Q SP, zymogen and activated forms, respectively, (lane 7) thermolysin.
Figure 10:
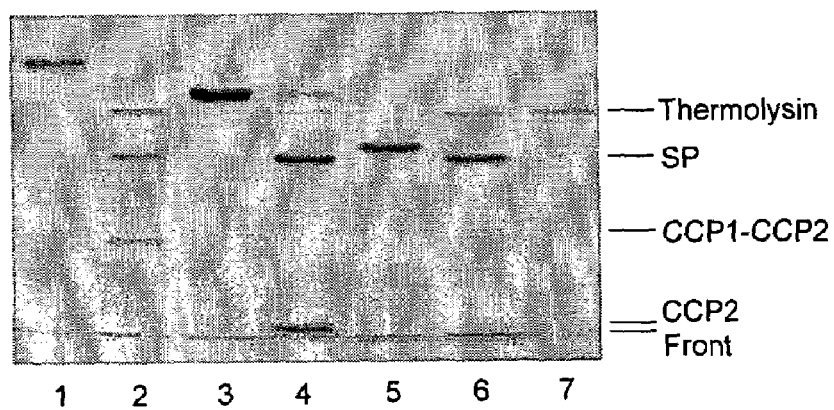

Three cDNA fragments from the catalytic region of C1r (FIG. 9) have been cloned into a modified pET-17b vector in fusion with the (Met)-Ser-Thr-Gln-Ala sequence. Each insert begins with a Cys (Cys , Cys , Cys41 in the case of CCP1-CCP2-SP (γB), CCP2-SP and SP, respectively) at the N-terminus and ends with Asp$^{705}$ at the C-terminus. The mature proteins have an N-terminal sequence Ser-Thr-Gln-Ala-(Cys)... as verified by protein sequencing. In order to prevent autoactivation, stabilized mutant constructs were also expressed. In one series we introduced the Arg463 Gln mutation into the cDNAs, while in another series we changed the active site Ser654 to Ala for all the three fragments. The expression plasmids were transformed into the E. coli BL21 (DE3) pLysS strain and the recombinant protein expression was induced by adding IPTG. After induction the cells were lysed and the soluble and insoluble fractions were separated by centrifugation and analyzed on SDS-PAGE (data not shown). In the soluble fraction we could not detect recombinant proteins using Coomasie blue staining, whereas the pellet contained almost exclusively the recombinant C1r fragments (purity approx. 80%). Since the recombinant proteins were present as inclusion bodies, renaturation procedures were needed to generate the native, folded structure. The inclusion bodies were solubilized in 6 M guanidine-HCl solution, which contained 100 mM DTT to reduce all the disulfide bridges. The solubilized recombinant proteins (~10 mg/ml) were then diluted 400-fold (final concentration ~25 μg/ml) using different refolding buffers and incubated at 15° C. overnight. Many different refolding solutions containing various additives and different oxido shuffling reagents were tested for the three fragments and the best ones were selected for large scale renaturation (17, 18). We found the highest renaturation yield using 2 M guanidine-HCl in the case of CCP1-CCP2-SP fragment and 0.5 M L-arginine in the case of CCP2-SP and SP fragments. The optimal oxido shuffling system was the mixture of reduced and oxidized glutathione in a ratio of 3 mM GSH/1 mM GSSG at pH 8.3 in all experiments. The efficiency of the folding process could be estimated by reducing SDS-PAGE, since native, functionally active C1r can cleave itself into two chains (y 18 kDa and B 30 kDa chains in the case of the CCP1-CCP2-SP fragment). Since the denatured recombinant proteins have single-chain structure in the inclusion bodies, the appearance of two chains on the reducing gel is a good indicator of autoactivation and hence of successful renaturation of the wild type fragments (FIG. 10A). Edman degradation of the large (30 kDa) chains yielded the Ile-Ile-Gly-Gly-Gln sequence in all cases, indicating that the correct autolytic cleavage at the Arg$^{463}$-Ile$^{464}$ bond between the γ and B chains had occurred during the activation process. The efficiency of the renaturation was about 10-20%, allowing us to obtain enough material for all subsequent physico-chemical and functional studies. After the renaturation process the aggregated material was removed by filtration on a 0.45 μm nitrocellulose membrane, and the refolded recombinant proteins were purified by anion-exchange and gel-filtration chromatography as described in the Experimental Procedures. On the Q-Sepharose Fast Flow column most of the contaminants did not bind to the resin at low ionic strength (20 mM NaCl and 20 mM Tris-HCl) and could be removed by washing the column with the low salt buffer. The correctly folded, native recombinant fragments eluted as single peaks detected at 280 nm during the ascending salt gradient. There was no difference between the elution volume of the wild-type (activated) and the R463Q or S654A mutant (zymogen) fragments. The recombinant fragments were essentially pure after the ion-exchange chromatography, however to remove the traces contaminants we performed a gel filtration chromatography on a Superose-12 FPLC column. After this step the protein solutions were concentrated and the concentrations of the recombinant proteins were measured from the absorbance at 280 nm. The final yields for the CCP1-CCP2-SP, CCP2-SP and SP fragments were 2, 5, and 2 mg/l of culture, respectively. Both the wild-type and the zymogen mutant fragments yielded a single band on non-reducing SDS-PAGE analysis, although with different apparent molecular weights (~45 kDa and ~39 kDa for wild-type CCP1-CCP2-SP and zymogen CCP1-CCP2-SP, respectively, ~38 kDa and ~34 kDa for wild-type and zymogen CCP2-SP, and ~31 kDa and ~27 kDa for the wild-type and zymogen SP fragment). On the reducing gel however the wild-type fragments exhibited the activated two-chain forms (~30 kDa for the B chain and ~18 kDa for the γ chain), whereas the zymogen mutants retained a single-chain structure. In order to prove the correct folding of the zymogen mutants, the renatured proteins were converted into the two-chain form. The Arg463Gln mutants could be specifically cleaved at the Gln$^{463}$-Ile$^{464}$ and activated by thermolysin (FIG. 10B). After thermolysin treatment all the three R463Q fragments showed proteolytic and esterolytic activity similar to that of the wild-type autoactivated proteases (Table 5). The Ser654Ala mutants cannot autoactivate themselves, but wild-type C1r fragments could cleave them at Arg$^{463}$-Ile$^{464}$ activation site, as verified by protein sequencing.

Physico-Chemical Characterization

Gel Permeation Chromatography—Relative Molecular Weight

Figure 11:
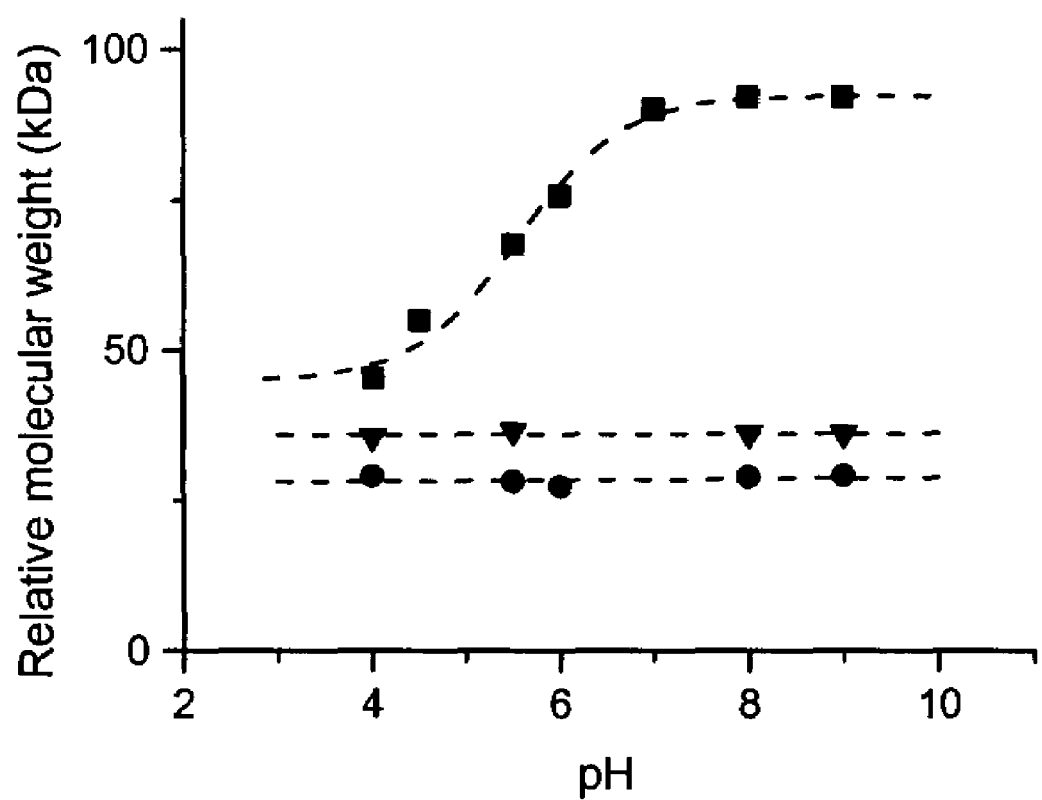
FIG. 11. Relative molecular weights of C1r fragments vs. pH determined by gel filtration chromatography SP (λ), CCP2-SP (τ), and CCP1-CCP2-SP (ν). CCP1-CCP2-SP shows a dimer-monomer transition with a midpoint at pH 5.5. Molecular weights were determined on a Superose-12 column using a protein standard series at every pH, at 25° C., as described in Materials and methods.

In order to determine the relative molecular weight and investigate the dimerization properties of the expressed and renatured C1r fragments, the relative molecular weights of the three C1r fragments vs. pH were analyzed by gel permeation chromatography. The molecular weights of the three C1r fragments were determined relative to the standards at every pH. (FIG. 11).

The SP and the CCP2-SP fragments showed molecular weights of 28-30 kDa and 36-38 kDa, respectively. These values were independent of pH and were in accord with the molecular weights determined from SDS-PAGE analysis. The relative molecular weight of the CCP1-CCP2-SP fragment was found to be approximately 90 kDa at neutral or alkaline pH. Below pH 6.0 it showed a sigmoidal shaped decrease to 44-47 kDa, which is the molecular weight of the monomer CCP 1-CCP2-SP, and is in accord with the SDS-PAGE.

Differential Scanning Calorimetry

DSC measurements were performed on one hand to check the native structure of the fragments and on the other hand to investigate the role of the individual domains in the conformational stability of the catalytic region of C1r.

Figure 12:
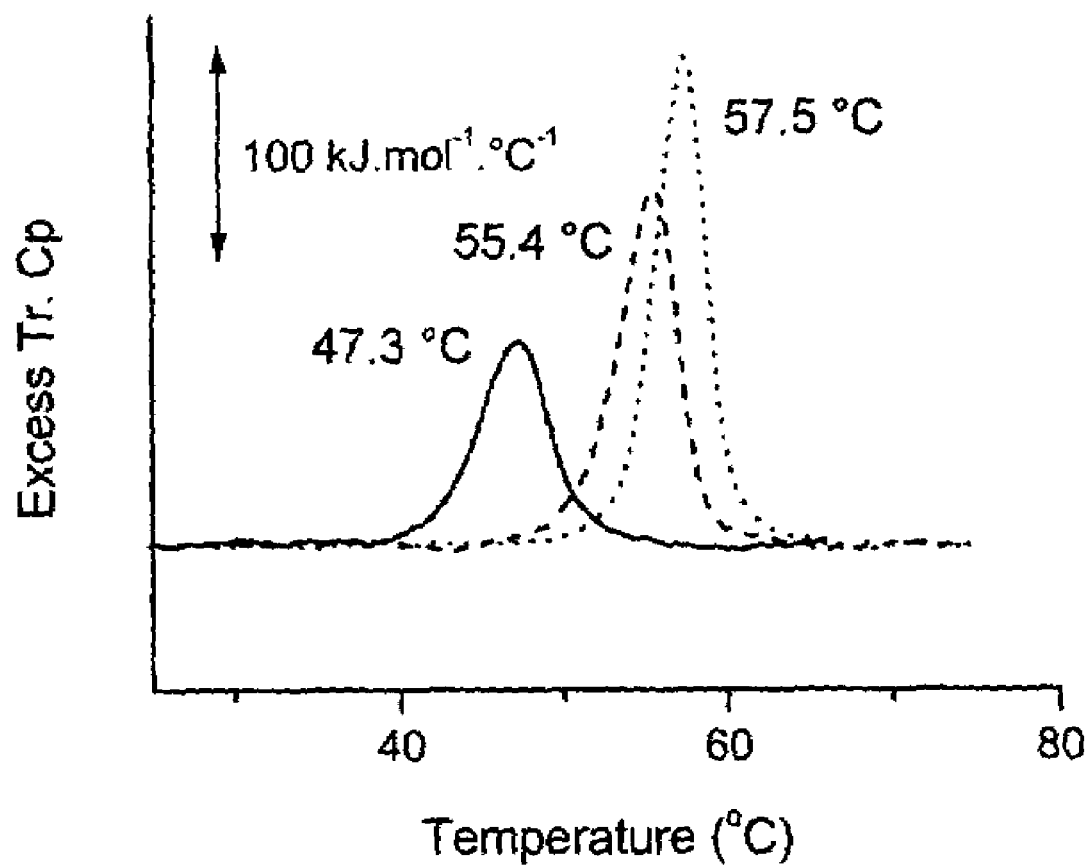
FIG. 12. DSC melting curves of the C1r fragments SP (———), CCP2-SP ( - - - ) and CCP1-CCP2-SP ( . . . ) in 20 mM Tris pH 8.3 buffer containing 145 mM NaCl. The protein concentration was 0.1 mg/ml. A heating rate of 1° C./min was used.

The SP fragment showed a sharp, cooperative melting transition at a relatively low temperature (47.5° C.), indicating a compact, stable structure of the molecule (FIG. 12).

Fragment CCP2-SP showed a cooperative unfolding curve with a melting point at 55.4° C. The larger calorimetric enthalpy change and the significantly higher melting temperature compared to that of SP indicate that the CCP2 module establishes tight interactions with the SP domain and significantly improves its stability.

The CCP1-CCP2-SP fragment showed an unfolding transition at 57.5° C., which is in good agreement with that of the equivalent CCP1-CCP2-SP produced in baculovirus expression system (58.3° C.) (19). These data prove that renatured CCP1-CCP2-SP is in a native form and that its conformational stability is similar to that of a CCP1-CCP2-SP with a somewhat larger N-terminal and with carbohydrate side-chains. The stability of CCP1-CCP2-SP is somewhat higher than that of CCP2-SP. The presence of the CCP1 module and the dimerization of the CCP1-CCP2-SP fragment exert less effect on the stability of the protein as compared to the significant stabilizing effect of the CCP2 module in the interaction with SP domain in the CCP2-SP construct.

Functional Characterization of the Recombinant Proteins

Esterolytic Activity on Synthetic Substrates

The values of the catalytic efficiency ($k_{cat}/K_M$) for the reaction of the C1r fragments with the Z-Lys-S-Bzl, and Z-Gly-Arg-S-Bzl thioesters are presented in Table 5. Z-Lys-S-Bzl is not a "good" substrate for C1r, but its spontaneous hydrolysis rate is very low, therefore measurements of low catalytic activity was possible. Z-Gly-Arg-S-Bzl, a more sensitive thioester substrate of C1r was hydrolyzed at high rate by the fragments. The three C1r fragments showed similar esterolytic activities on the thioester substrates indicating similar active site conformations in the SP, CCP2-SP and CCP 1-CCP2-SP fragments. The CCP2-SP fragment, however proved to be slightly more potent as compared to the others. The observed $k_{cat}/K_M$ values on the Z-Gly-Arg-S-Bzl substrate are four times higher than those described previously for the entire C1r molecule isolated from human serum (13).

The Catalytic Efficiency of C1s Cleavage by the Recombinant C1r Fragments

Figure 13:
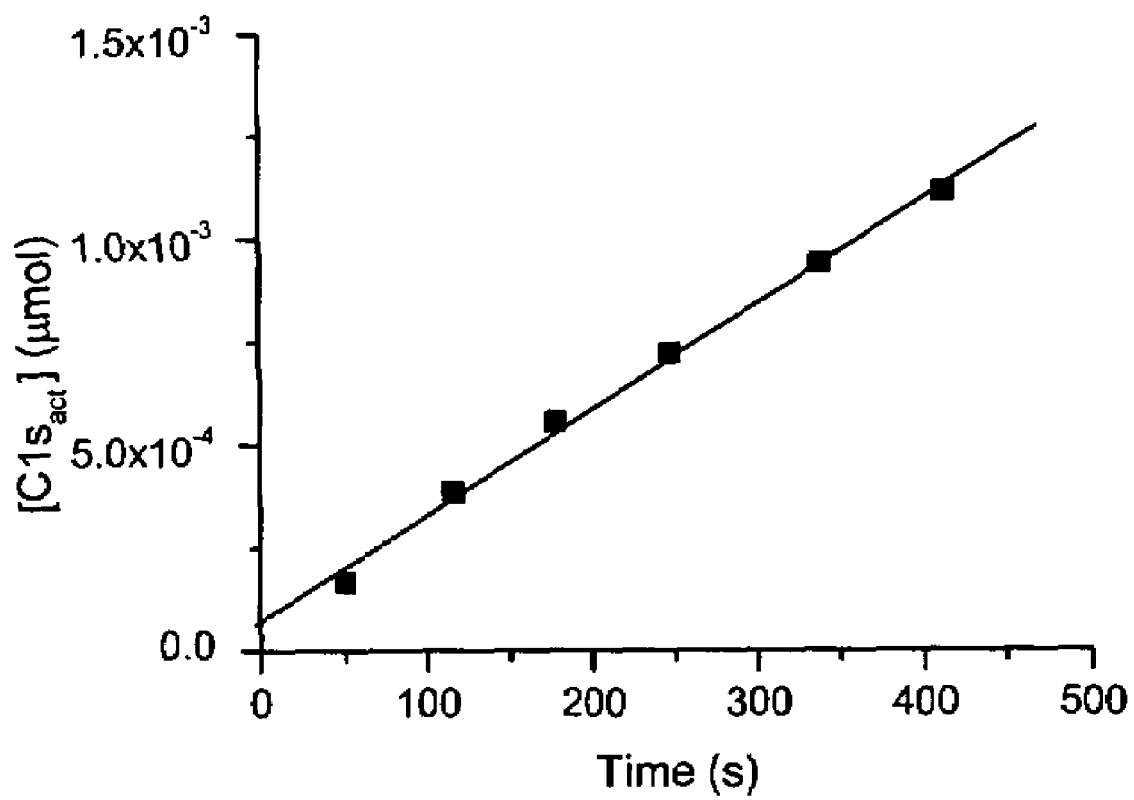
FIG. 13. Proenzyme C1s cleavage by C1r CCP1-CCP2-SP The figure shows a typical experiment which was carried out in 20 mM Tris pH 7.4 containing 145 mM NaCl with an enzyme:substrate ratio of 1:50 at 30° C. The generated active C1s molecules were monitored through their esterolytic activity on Z-Lys-S-Bzl substrate.

The ability of the C1r fragments to cleave proenzyme C1s was tested through the esterolytic activity of the activated C1s molecules on the Z-Lys-S-Bzl thioester substrate. Although C1r also cleaves this substrate (see Table 5), its catalytic efficiency is about two orders of magnitude less than that of C1s. An enzyme-substrate ratio of 1:50 assures that the activity of C1r on the Z-Lys-S-Bzl was negligible compared to that of C1s. The proenzyme C1s concentration (0.04-0.1 μM) was orders of magnitude below the $K_M$ value and this allowed direct calculation of the $k_{cat}/K_M$ values from the linear part of the C1s activation curve. Kinetic analysis of the activation of C1s by CCP1-CCP2-SP is shown on FIG. 13. The slope of the line is proportional to the catalytic efficiency. The results with the three C1r fragments are summarized in Table 6. All the three fragments efficiently cleaved proenzyme C1s. The CCP2-SP fragments exhibited an exceptionally high $k_{cat}/K_M$ value.

Cleavage of the S654A Mutant Fragments with the Wild-Type Enzymes

Figure 14:
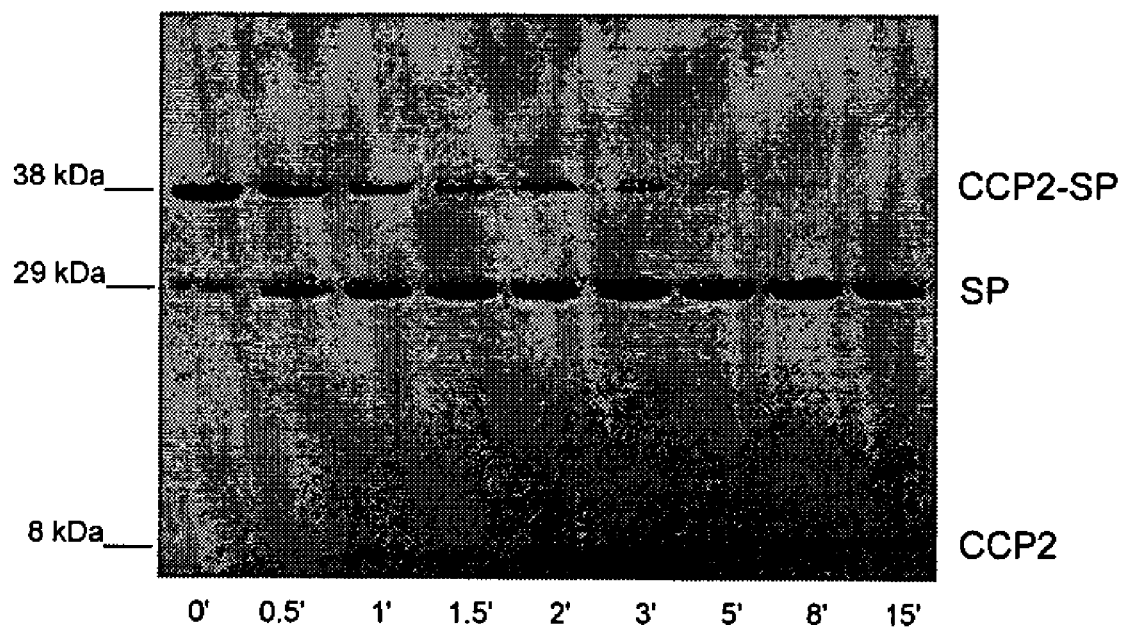
FIG. 14. Cleavage of CCP2-SP S654A zymogen mutant by wild-type CCP2-SP The reaction was performed in 20 mM Tris, 145 mM NaCl, pH 8.3 at 37° C. An enzyme:substrate ratio of 1:15 was used. The activation process was followed by 12.5% SDS-PAGE under reducing conditions. Reaction times for the appropriate lanes are indicated. After cleavage the CCP2 and SP domains are separated under reducing conditions.

Proenzyme S654A mutant fragments were used as substrates in investigating autoactivation properties of the wild-type fragments. The active enzyme cleaves and activates proenzyme S654A mutant that has no catalytic activity even in the two-chain form. Thus, the autoactivation can be studied in a simple enzyme-substrate system. The activity of wild-type SP, CCP2-SP, and CCP1-CCP2-SP on the S654A mutants of the SP, CCP2-SP, and CCP1-CCP2-SP fragments were measured in each combination. Cleavage of the S654A mutants was followed by reducing SDS-PAGE. Catalytic efficiency values are presented in Table 7. In all enzyme-substrate pairs a high catalytic efficiency, comparable to the activities on synthetic ester substrates could be detected. SP fragment activated the three S654A mutants at a similar rate. The highest $k_{cat}/K_M$ values were obtained for the self-activation of the CCP2-SP fragment (i.e. its activity on the S654A mutant CCP2-SP) (FIG. 14).

4. Discussion of Results with the MASP-Fragments

A principal, but so far debated question is the autoactivation capacity of MASP-1 and MASP-2. Since prior to renaturation the MASP protein fragments were single-chain polypeptides, the autoactivation process, which involves the cleavage of an Arg-Ile bond in the serine protease domain, could be followed on reducing SDS-PAGE. Upon renaturation the MASP-1 CCP1-CCP2-SP fragment became fully activated, and gave two bands (corresponding to the "γ"-and "B"-chains) on the PAG. In addition to the two major bands, we observed a minor band of 24 kDa, which co-purified with the MASP-1 CCP1-CCP2-SP fragment. This band is most probably an autolytic cleavage product of the serine protease domain. The autolytic cleavage at the $Arg^{504}$-$Asp^{505}$ bond removes the active site His, which results in the destruction of the protease activity. We can conclude that MASP-1 has a strong propensity to autoactivate and the activated enzyme is prone to autodegradation upon prolonged incubation. The physiological relevance of this autolysis is yet unknown, but it is noteworthy to mention that we observed the corresponding autolytic product of the full-length MASP-1 protein, in partially purified serum MBL-MASPs complexes (data not shown).

In terms of autoactivation capacity the MASP-2 catalytic fragments revealed somewhat different features. Throughout the renaturation procedure the MASP-2 fragments retained their proenzyme form. Post purification, however, they migrated as two separate bands on reducing SDS-PAGE, a characteristic of activated enzyme. Subsequent N-terminal sequencing confirmed that the cleavage occurred at the $Arg^{444}$-$Ile^{445}$ activation bond. Therefore, it is very likely that MASP-2 also has the capacity to autoactivate, but the reaction is slow at low concentrations. Typically, to prevent aggregation the protein concentration is kept very low during renaturation (1-2 μg/ml). During purification, however, the protein concentration increases dramatically on the ion exchange columns (the peak fractions could be as concentrated as 1-2 mg/ml), which can facilitate the autoactivation process and increase the overall rate of active enzyme formation. We are tempted to believe that the autoactivation reaction of MASP-1 and MASP-2 is similar to that of C1r: In the first step zymogen molecules activate zymogens, while in the second step the generated active enzymes cleave zymogen molecules. In a concentrated solution the probability of the reactive encounters between MASP-2 molecules (either zymogenic or activated) is greater than in a diluted solution. It was shown by Vorup-Jensen et al. that the MBL-MASP-2 complex alone is sufficient for complement activation. Although, we do not know the stoichiometric composition of this complex, but it is very likely that at least two MASP-2 molecules associate with the MBL molecule (Chen, 2001). This view is further strengthened by the fact that both MASP-1 and MASP-2 form homodimers through their N-terminal CUB1-EGF-CUB2 region (Thielens, 2001). Our observations reveal that the smaller MASP-2 fragments (CCP2-SP and SP) can also autoactivate, indicating that the autoactivating ability is an inherent property of the serine protease domain. In contrast to previous suggestion (Rossi, 2001) it seems that the CCP modules of MASP-2 do not play an essential role in this process. The MASP-2 CCP1-CCP2-SP fragment also showed a sign of autodegradation, since its N-terminal begins with $Ile^{291}$ instead of the expected Ala. It looks very likely that the short stretch of CUB2 domain fused with the Ala-Ser-Met tripeptide at the N-terminus (Ala-Ser-Met-Thr-Gly-Trp-$Lys^{290}$) folded loosely and the $Lys^{290}$-$Ile^{291}$ bond in this region was an easy target for a protease with trypsin-like specificity (i.e. MASP-2).

Probably the most controversial issue concerning the substrate specificities of MASP-1 and MASP-2 is their ability to cleave C3. We aimed at resolving this debate by using our catalytic fragments and carefully prepared C3 substrates. C3 contains a thiol ester group inside the molecule that becomes exposed after the cleavage of C3 by the C3 convertase enzymes. The exposed thiol ester group is then rapidly hydrolyzed or reacted with a nucleophile on the cell surface. Nevertheless, uncleaved C3 is also prone to spontaneous hydrolysis yielding non-functional $C3(H_2O)$, which may occur during the purification process and upon prolonged storage. It is important to differentiate between 'live' C3 (i.e. C3 with an intact thiol ester bond) and 'dead' C3 (C3 with a reacted thiol ester bond), as they respond differently to proteolysis although they migrate similarly on SDS-PAGE. We measured the kinetic parameters of C3 cleavage by using both freshly prepared 'live' C3 and 'dead' C3. Our results demonstrate that the $k_{cat}/K_M$ values of both MASP-1 and MASP-2 on 'live' C3 substrate were very low (~300 $M^{-1}s^{-1}$). We believe that this marginal activity is not sufficient for direct complement cascade activation in the presence of such potent inhibitors in serum as C1-inhibitor or aplha-2-macroglobulin. 'Dead' C3 was cleaved with a low but significant efficiency: the $k_{cat}/K_M$ values were about 10-20 fold higher than in the case of 'live' C3 cleavage. It is possible therefore that the C3 cleaving activities of the MASPs, reported earlier in the literature, were mostly due to the high ratio of 'dead' C3 in C3 preparations. Still, it can not be excluded that the marginal activities of MASP-1 and MASP-2 on 'live' C3 may have physiological consequences (e.g. initiating the alternative pathway). Nevertheless, we strongly believe that C3 is not the real natural substrate of either MASP-1 or MASP-2.

C4, similarly to 'live' C3, was basically resistant against the proteolytic activity of MASP-1. C2, however, was digested by the recombinant MASP-1 fragment at a moderate rate. The $k_{cat}/K_M$ value for the C2 cleavage was two orders of magnitude higher, than that of the C4 cleavage. The C2 cleavage alone, however, is not sufficient to initiate the complement cascade, since physiologically relevant C2 cleavage occurs on the C2C4b complex. It should also be stressed that this moderate $k_{cat}/K_M$ value is smaller by an order of magnitude than the corresponding values of MASP-2 or C1 s.

The recombinant MASP-2 fragments cleaved C2 and C4 efficiently. This and the autoactivating capacity of MASP-2 is in accordance with the observation that MBL-MASP-2 complex can activate the complement cascade. Since we expressed three different functionally active truncated catalytic fragments of MASP-2 (i.e. CCP1-CCP2-SP, CCP2-SP and SP), we could analyze the role of the individual domains in C2 and C4 cleavage. It can be concluded that C2 cleavage is mediated entirely by the serine protease domain. The highest $k_{cat}/K_M$ value was measured in the case of the single SP domain fragment. The addition of the CCP modules to the SP domain somewhat decreased the catalytic efficiency. The SP domain therefore probably contains all necessary contact sites for efficient C2 binding and cleavage, and the CCP domains do not contribute to this reaction, On the contrary, C4 digestion of the MASP-2 fragments is influenced by the presence of the CCP domains. Although, the single SP domain can cleave C4 at a moderate efficiency, the addition of the CCP2 module to the SP domain increases the $k_{cat}/K_M$ value dramatically (44-fold increase). It seems very likely, that the CCP2 domain contains additional binding site(s) for the protein substrate C4. This is reflected in the decrease of the KM value (from 2.0 µM to 0.4 µM), which indicates a stronger binding of the substrate. Our results are similar to previous results of Rossi et. al., who demonstrated the essential role of CCP2 module in the C4 digestion ability of C1s (Rossi, 1998). Apparently, the CCP2 domains play an essential role in determining the enzymatic properties of the MASP-2 proteases (Table 4). The presence of the CCP1 module on the CCP1-CCP2-SP fragment of MASP-2 decreases its catalytic efficiency. Nevertheless, the catalytic efficiency of MASP-2 CCP1-CCP-2-SP against C4 is still high, and the $k_{cat}/K_M$ values of this MASP-2 fragment are practically equal (~500 000 $M^{-1}s^{-1}$) for the C2 and C4 substrates.

The above results, together with the finding that MASPs are inactive against C3 provide an assay method for selective determination of MASP-1 and MASP-2 levels. Such an assay would comprise for example the steps of monitoring C2 cleavage and C4 cleavage by MASP proteins in aliquots of the sample whereas, if desired, other complement pathways are blocked, considering C4 conversion as a result of MASP 2 activity and C2 conversion as a result of MASP-1 and MASP-2 activity together calculating MASP-1 and MASP-2 levels using either known specific activity values of said proteins or CCP1-CCP2-SP fragments as inner standards.

The question was raised whether a similar assay method can be carried out on the basis of different inhibitor specificities of MASP-1 and MASP-2.

Both C1-inhibitor and alpha-$_2$M were able to block the proteolytic activities of both MASP-1 and MASP-2. In the case of C1-inhibitor a 1:1 molar ratio was necessary for complete inhibition The observed pseudo first order rates of reaction ($k_{obs}$) with C1-inhibitor were 5-fold less for the MASP-1 CCP1-CCP2-SP than for the MASP-2 CCP1-CCP2-SP fragment. Keeping in mind that we have measured a 4-5 fold higher specific activity for MASP-1 than for MASP-2 for arginine at the P1 sites by the competing oligopeptide substrate library assay, this result indicates that MASP-2 has much better interaction properties with C1-inh. The $K_i$ values for the C1-inhibitor and MASP-2 CCP1-CCP2-SP reaction were in the nanomolar range, which is an order of magnitude less than those of the C1r and C1s interactions with C1-inhibitor and is an indicator of strong binding (Sim, 1980) (Table 4).

Thus, C1-inhibitor specificity of MASP-2 is not sufficient to differentiate between the two MASPs.

However, a marginal molar excess of alpha-2-macroglobulin was enough to completely block the proteolytic activity of MASP-1, whereas only a 40-fold molar excess over the MASP-2 fragments was capable of significantly hindering C2 and C4 cleavage. The results of the experiment, where alpha-2-macroglobulin and C1-inhibitor competed for either the MASP-1 or the MASP-2 catalytic fragment, showed clearly that C1-inhibitor is a better inhibitor of MASP-2, while alpha-$_2$M is a significant inhibitor of MASP-1. In this respect it is interesting to note that MASP-1 represents an evolutionary ancient type of the serine proteases, since the active site Ser646 is encoded by a TCN type codon (Brenner, 1988). Another highly conserved Ser residue downstream the active site (Ser$^{667}$) is also encoded by TCN (Krem, 2001), moreover, there is a histidine loop around the active site and the SP domain is encoded by six exons (Endo, 1998). Alpha-2-macroglobulin, which is related to C3, also belongs to the thiol ester group of proteins.

Thus, an assay method for assessing MASP-1 and MASP-2 levels in a sample of biological origin can be carried out by performing the following steps:

monitoring C2 cleavage in the sample and considering C2 conversion as a result of MASP-1 and MASP-2 activity together, adding a calculated amount of α2M to the sample to inhibit MASP-1 activity (e.g. MASP-1 activity can be "titrated" to zero by following the curve for C2 conversion) but to leave MASP-2 activity unchanged or changing it to a negligible or a calculable extent, monitoring C2 activity in the sample comprising α2M, calculating MASP-1 and MASP-2 levels using either known specific activity values of said proteins or CCP1-CCP2-SP fragments as inner standards.

By comparing the substrate specificities of MASP-1 and MASP-2 on small synthetic peptide substrates we have created a screening method for substrates of these MASP enzymes. To the best of our knowledge the present invention provides the first comprehensive analysis of the substrate specificities and relative activities of MASP-1 and MASP-2 using a competing oligopeptide substrate library. The most important finding is that MASP-1, besides being a very potent peptidase, shows an extreme Arg selectivity at the P1 site of the substrates. While under same conditions the consumption of the P1 Lys substrate is quite comparable between the MASP-1 and MASP-2 catalytic fragments, the MASP-1 CCP1-CCP2-SP fragment digests the P1 Arg peptide 4-5 fold more efficiently than the corresponding fragment of MASP-2. The substrate specificity of MASP-2 resembles trypsin, whereas MASP-1 acts like thrombin or mouse endoproteinase Arg-C (Antal, 2001). The high catalytic potential of MASP-1 suggests that there exists a natural substrate for MASP-1, which is cleaved more efficiently than C3. Indeed, in recent studies Hajela et al. showed that MASP-1 cleaves fibrinogen and Factor XIII at much faster rates than C3 and is thus, similarly to thrombin, able to catalyze the formation of cross-linked fibrin.

Using the results of the present study and data obtained by other laboratories we can compare some basic characteristics of the MASP-1 and MASP-2 proteases (Table 4). All of these proteases are capable of autoactivating. These proteins (MASP-1 and MASP-2) circulate in serum as homodimers, which facilitates their autoactivation, as autoactivation presumes contact between two serine protease domains. In fluid phase, however, MASP-2 autoactivates only at higher concentrations, than MASP-1. The capacity to autoactivate enables MASP-2 through cleaving C2 and C4 to initiate the complement cascade after having received an activation signal from a recognition molecule (e.g. C1q, MBL or ficolin). As in vivo natural substrates of MASP-1 are not yet well characterized the physiological consequences of its autoactivating capacity is hard to predict.

The isolated serine protease domains of C1r, C1s and MASP-2 possess proteolytic activities. In the case of C1s and MASP-2 the serine protease domains alone cleave C2 as efficiently as the whole molecule. Nevertheless, for efficient C1s cleavage by C1r and efficient C4 cleavage by C1s and MASP-2 the CCP2 module is essential. This could be partly attributed to the feature conserved during evolution that the CCP2 module forms a compact structural and functional unit with the SP domain (Gaboriaud, 1998/Gaboriaud, 2000/Budayova-Spano, 2002). All four proteases can be inhibited by the serpin C1-inhibitor, but MASP-1 is much more sensitive to alpha-$_2$M.

Our work provided an important detail in the identification of the natural substrate of MASP-1. We showed that MASP-1 is a very potent peptidase and has an extreme Arg specificity at the P1 site. This behavior resembles thrombin, the terminal protease of the blood clotting cascade.

Several lines of evidences indicate that the complement and the blood clotting cascades evolved from a common ancestral protease cascade (Krem, 2002). It has also been reported that sequence homologues of fibrinogen served immunological roles. Therefore, it can be speculated that MASP-1, as an ancient protease, shows characteristics of both cascades (complement-like features: interaction with MBL, inhibition by C1-inhibitor; clotting-like feature: arginine selectivity at P1, cleavage of fibrinogen and Factor XIII). Thus, it is contemplated that MASP-1 can be used for inducing formation of fibrin from fibrinogen and thereby promoting blood clotting.

5. Discussion of Results with the C1r Fragments

In the present study we used an *E. coli* based expression system for recombinant production of fragments representing the catalytic region of human C1r.

Previously the baculovirus-insect cell system was used to produce recombinant C1r and C1s and their fragments (14, 20, 21). In this system the post-translational modifications are not complete. Furthermore, the level of β-hydroxylation of the Asn residue in the EGF domain (Asn$^{167}$ in C1r and Asn$^{149}$ in C1s) is very low (14, 22) and the glycosylation patterns differ significantly from the complex type glycosylation found in the case of serum proteins. These differences in the post translational modifications however did not seem to affect significantly the functional properties of the recombinant proteins; at least some studies showed that aglycosylated proteins retained their biological activity (14, 21).

In order to explore the contribution of the individual domains to the above-mentioned properties of C1r we successively deleted the CCP domains preceding the SP domain from the cDNA. As a result, we made and expressed three cDNA constructs. The recombinant proteins accumulated as inclusion bodies inside the *E. coli* cells. After disruption of the cells we purified and renatured these proteins. The renatured fragments were purified to homogeneity by ion-exchange chromatography and gel filtration. After these procedures all the three fragments were in a correctly folded, functionally active form as confirmed by subsequent physico-chemical and enzymatic measurements. After renaturation the wild-type fragments were present in the activated, two-chain form. Autoactivation is a good indicator of correct folding. Indeed, by the end of the renaturation procedure the activation was complete. To study the zymogen form of the enzymes, as well as the autoactivation procedure, we constructed and expressed mutant C1r fragments i.e. stable proenzymes. In one set of experiments we mutated the Arg$^{463}$-Ile$^{464}$ cleavage site to Gln-Ile (27), while in another set we changed the catalytic site Ser$^{654}$ to Ala. In the first case the zymogen cannot be activated by a trypsin-like serine protease, however it could be cleaved and converted to an active enzyme by thermolysin. In the case of the Ser654Ala mutants the Arg-Ile bond can be cleaved by wild-type C1r, but the mutant itself cannot function as an active protease. All of these C1r fragments were produced with a similar yield except the CCP2-SP fragments where the renaturation efficiency was significantly higher. This can be interpreted as the CCP2 domain closely associates with the SP domain forming a compact cooperative folding unit. The SP domain alone is less stable as it is indicated by the DSC measurements. The CCP1-CCP2-SP fragment contains the CCP1 module, which associates loosely to the CCP2-SP. The larger, more complex structure of CCP1-CCP2-SP can account for its lower renaturation yield.

The DSC measurements indicate that all of the renatured fragments have compact, folded structures. The calorimetric heat denaturation curves (excess heat capacity against temperature) show cooperative unfolding of the native structures in the case of the three fragments. The heat capacity curve of the recombinant CCP1-CCP2-SP is essentially identical to the curve of CCP1-CCP2-SP expressed in the baculovirus insect cell system. According to the DSC curves the SP fragment has the least stable structure. The CCP2 module exerts a dramatic stabilizing effect, as the midpoint of the heat denaturation peak of SP (47.5° C.) is being shifted to 55.4° C. in the case of the CCP2-SP fragment (FIG. 12). The presence of the CCP1 module stabilizes the structure further, but this effect is much less significant than that of CCP2. These results are in agreement with the homology model of the catalytic region of C1r (8) and with the crystal structure of the CCP2-SP fragment of C1s (28). According to the crystal structure the CCP2 module associates to SP domain through a rigid module-domain interface involving intertwined proline and tyrosine-rich polypeptide segments. Such a rigid CCP-SP assembly is conserved in other extracellular proteases (29).

Gel filtration experiments show that the SP and CCP2-SP fragments are monomers at all pH values, whereas the CCP1-CCP2-SP fragment is a dimer at neutral and basic pH (FIG. 11). Like serum C1r (30), our recombinant CCP1-CCP2-SP dimers dissociate under slightly acidic conditions. These results provide straightforward experimental evidence that the CCP1 domain is involved in the dimerization of C1r. Previously a three-dimensional model of activated (γB)$_2$ has been constructed, which was based on chemical cross-linking and homology modeling (8). Chemical cross-linking of the (γB)$_2$ fragment produced by autolytic cleavage of the active serum C1r indicated the existence of converse salt bridges between Lys$^{299}$ in the N-terminal region of the γ segment of one monomer, and Glu$^{510}$ of the serine protease domain of the other monomer. Our CCP1-CCP2-SP construct however begins with the Cys$^{309}$ of C1r preceded by the Ser-Thr-Gln-Ala N-terminal fusion peptide and therefore lacks Lys 299. The fact that our recombinant CCP1-CCP2-SP is a stable dimer indicates that formation of salt bridges between Lys$^{299}$ and Glu$^{510}$ is not a prerequisite of dimerization. Future site directed mutagenesis experiments could reveal the amino acid residues of the CCP1 module that are involved in C1r dimerization.

Regarding enzymatic activity it is surprising that the serine protease domain of C1r alone can cleave C1s with a rate comparable with that of the activation by the CCP1-CCP2-SP fragment. This indicates that the SP domain contains all the structural elements necessary for C1s binding and cleavage. The presence of the CCP2 domain alone in the CCP2-SP fragment however causes a dramatic increase (one order of magnitude) of the $k_{cat}/K_M$ value of the reaction. We can conclude that the CCP2 domain is responsible for the enhancement of the efficiency of the C$_1$s cleaving activity of C$_1$r. We suggest that although the SP domain alone can cleave C$_1$s, the CCP2 domain provides with additional contact surfaces for binding and orienting the substrate. As we mentioned above, our results obtained by DSC indicate that the CCP2 domain strongly stabilizes the structure of the SP domain. The increase of the $k_{cat}/K_M$ value could be explained in principle by this domain-domain interaction. The similar esterolytic activity of the recombinant $C_1r$ fragments however shows that this is not the case. It is obvious that all the three recombinant $C_1r$ fragments contain a fully functional active site. The changes in stability caused by the addition of CCP modules to the serine protease domain do not affect the catalytic power of the serine protease active site on the synthetic substrates. We suspect that the dramatic increase of the C1s cleaving ability of the CCP2-SP fragment is due to additional substrate binding sites present on the surface of the CCP2 domain, and not to the stabilizing effect. The corresponding $k_{cat}/K_M$ value of the CCP 1-CCP2-SP fragment for C1s cleavage however is smaller than that of the CCP2-SP fragment. As we showed above the CCP1 domain is responsible for the dimerization of C1r. The catalytic site of C1r or the substrate binding residues on the CCP2 domain can be less accessible for the C1s in the CCP1-CCP2-SP dimers than in the CCP2-SP and SP monomers. It is also very likely that the CCP1 domain does not contain additional substrate binding sites for C1s. We should keep in mind that we are dealing with fluid phase reactions in our present study. Inside the C1 complex however the catalytic domains of C1r and C1s are precisely positioned, therefore the efficiency of C1s cleavage by the C1r dimer can be significantly higher (31).

Our work with recombinant fragments provided valuable information concerning the autoactivation of C1r. The S654A mutant retains its zymogen form during the renaturation and purification procedure, whereas the wild-type C1r fragments are fully activated after the same treatment. We can conclude that this activation is a true autoactivation and that extrinsic (i.e. *E. coli*) proteases do not contribute to it. Since all the three wild-type fragments autoactivate, two important conclusions can be drawn: (i) dimerization is not a prerequisite for autoactivation, (ii) autoactivation is an inherent property of the serine protease domain. Previously, autoactivation was shown to be a property of the dimers both in the case of the entire molecule and its CCP1-CCP2-SP fragment (7). Under acidic conditions (pH<5.5) the C1r dimer dissociates and the resulting monomers lose their ability of autoactivation (32). Since at acidic pH the catalytic activity of the serine protease active center is expected to decrease it was not clear which phenomenon was responsible for the loss of the autoactivation ability. Our results indicate that under physiological conditions the monomeric CCP2-SP fragment is capable of autoactivation i.e. dimerization is not required for autoactivation. Since the SP domain itself retains the ability to autoactivate, the presence of even one CCP domain is not a prerequisite for autoactivation.

Autoactivation of C1r is supposed to be a two step process. In the initial step zymogen molecules activate zymogens, while in the second step the generated active enzymes cleave zymogen molecules. The fact that our wild-type fragments can autoactivate shows the existence of the initial step. The second step could be studied in detail using our zymogen mutants. The Ser654Ala mutants, which have an inactive catalytic center but have a cleavable Arg-Ile bond were used as substrates for the wild-type fragments. We determined the kinetic constants for these type of reactions (Table 7). Each Ser654Ala mutant was cleaved by its own wild-type counterpart. The SP fragment showed effective self-cleavage ability. The higher catalytic efficiency of the CCP2-SP construct compared to that of the SP domain can be interpreted assuming that the CCP2 domain, like in the case of the C1s cleavage, orients the Arg-Ile bond of one C1r in a favorable position to be cleaved by the active site of the other C1r. The CCP1-CCP2-SP fragment possess significantly lower $k_{cat}/K_M$ values than the other two fragments. Since on (CCP1-CCP2-SP)$_2$ we follow intermolecular (inter dimeric) cleavage, we may conclude that dimer formation partially blocks the accessibility of either the catalytic site of the protease, or the activation site of the proenzyme and therefore decreases the efficiency of the proteolysis. To clarify this question we carried out experiments with combinations of the different fragments. The fact that the wild-type SP fragment exerts similar proteolytic activity on the dimeric CCP1-CCP2-SP fragment and on the smaller monomer fragments, indicates that the Arg-Ile bond to be cleaved is accessible for extrinsic cleavage. The catalytic efficiency of CCP2-SP on CCP1-CCP2-SP also supports this observation. In a complementary experiment the wild-type CCP1-CCP2-SP fragment showed decreasing catalytic efficiency with the increasing size of the substrate proenzyme SP, CCP2-SP and CCP1-CCP2-SP S654A fragments. It is very likely that the catalytic site of one CCP1-CCP2-SP is pointed to the "inside" (i.e. toward the other CCP1-CCP2-SP molecule) in the dimer and this positioning facilitates the intramolecular autolytic cleavage.

The major conclusion of this work is that the serine protease module itself is an autonomous folding unit with inherent serine protease activity similar to that of intact C1r. The SP module has the ability to cleave C1s, the natural substrate of C1r, and autoactivation property is also retained.

Comparative measurements highlighted the role of the CCP modules in C1r as modulators of the catalytic functions through allosteric effects occurring upon binding to natural substrates and dimerization. The intimate interaction of the SP domain with the CCP2 domain is reflected in the sizeable stabilizing effect observed if CCP2 is attached to the SP module.

Antibody Production

Once folded C-terminal fragments have been obtained it becomes possible to prepare antibodies, preferably monoclonal antibodies against these fragments. Such techniques are well known in the art and described e.g. in Bonifacino et al. (2000), which is incorporated herein by reference. Monoclonal antibodies are useful then for detection of the multidomain serine proteases themselves. Moreover, they can be used in assay kits or in diagnostic kits for detection of e.g. MASP, C1r or C1s levels in biological samples. If the antibodies are directed to substrate binding sites they may serve as inhibitors as well.

TABLES

Kinetic Constants for the Cleavage of Live C3, Dead C3 (Table 1), C2 and C4 (Table 2) by MASP-1γB and MASP-2 fragments

TABLE 1

| | Cleavage of C3 | |
|---|---|---|
| | live C3 $k_{cat}/K_M (M^{-1} s^{-1})$ | C3(NH$_3$) $k_{cat}/K_M (M^{-1} s^{-1})$ |
| MASP-1γB | 300 ± 30 | 6 100 ± 600 |
| MASP-2γB | 350 ± 20 | 3 300 ± 300 |

$^a$values indicated are the averages of 2 to 4 experiments, standard errors are indicated below actual values.

Both MASP-1γB and MASP-2γB exhibited marginal proteolytic activity towards intact C3 (live C3). When inactivated C3 (C3(NH$_3$)) was substituted for intact C3 the reactivity of the MASPγBs increased about 10-20 fold.

TABLE 2

C2 and C4 cleavage

|  | C2 | | | C4 | | |
| --- | --- | --- | --- | --- | --- | --- |
|  | $k_{cat}$ (s$^{-1}$) | $K_M$ (μM) | $k_{cat}/K_M$ (M$^{-1}$ s$^{-1}$) | $k_{cat}$ (s$^{-1}$) | $K_M$ (μM) | $k_{cat}/K_M$ (M$^{-1}$ s$^{-1}$) |
| MASP-1γB | 0.10 ± 0.07 | 4.8 ± 4.3 | 30 000 ± 12 000 | 0.002 ± 0.001 | 2.7 ± 2.4 | 690 ± 400 |
| MASP-2γB | 1.9 ± 0.8 | 4.0 ± 1.7 | 500 000 ± 9 000 | 0.9 ± 0.4 | 1.6 ± 0.5 | 550 000 ± 50 000 |
| MASP-2 CCP-SP | 3.0 ± 2.2 | 2.7 ± 2.0 | 1 300 000 ± 200 000 | 2.0 ± 1.0 | 0.4 ± 0.2 | 5 700 000 ± 550 000 |
| MASP-2 SP | 3.9 ± 3.0 | 3.2 ± 2.8 | 2 500 000 ± 1 300 000 | 0.20 ± 0.06 | 2.0 ± 1.0 | 130 000 ± 30 000 |

[a] values indicated are the averages of 2 to 4 experiments, standard errors are indicated below actual values The MASP-2 fragments showed substantial proteolytic activity in both C2 and C4 cleavage. MASP-1γB cleaved C2 at a low but significant rate, whereas C4 cleavage was negligible.

TABLE 3

Kinetic constant for the reaction of MASP-1γB or MASP-2γB with C1-inh

|  | $k_{obs}$ (s$^{-1}$)[a] | $K_i$ (nM) | $k_2$ (s$^{-1}$) |
| --- | --- | --- | --- |
| MASP-1γB | 1.4 × 10$^{-3}$ | [b]N.A. | [b]N.A. |
| MASP-2γB | 7.8 × 10$^{-3}$ | 8.8 | 8 × 10$^{-3}$ |

[a] the pseudo-first order rate of reaction at [C1-inh] = 350 nM
[b] data not available

TABLE 4

Comparison of the lectin and the classical pathway serine proteases with respect to various properties

| Feature | Enzymes |
| --- | --- |
| autoactivation capacity | MASP-1 > MASP-2 |
| C2 cleaving capacity | MASP-2 >> MASP-1 |
| C4 cleaving capacity | MASP-2 |
| C3 cleaving capacity | (MASP-1~MASP-2)a |
| C1-inhibitor sensitivity | MASP-2 > MASP-1 |
| α2M sensitivity | MASP-1 > MASP-2 |

[a] only to a very limited extent and on "dead" C3 substrate

TABLE 5

Catalytic efficiency of wild-type C1r fragments and the thermolysin activated R463Q mutants for synthetic substrates[a]

|  | SP | CCP2-SP | CCP1-CCP2-SP |
| --- | --- | --- | --- |
| Z-Lys-S-Bzl | 1600[b] | 1900[b] | 1300[b] |
| Z-Gly-Arg-S-Bzl | 164000[b] | 210000[b] | 174000[b] |
| Z-Gly-Arg-S-Bzl | 112000[c] | 147000[c] | 124000[c] |

[a] $k_{cat}/K_M$ (s$^{-1}$M$^{-1}$). Measurement were carried out in 20 mM Tris, 145 mM NaCl, pH 7.4, at 30° C. $k_{cat}/K_M$ values are the averages of at least 3 independent experiments.
[b] Wild-type C1r fragments
[c] C1r R463Q fragments, after a treatment with 10 U thermolysin (Sigma)/mg C1r fragment, pH 8.0, 30° C., 2 h.

TABLE 6

Efficiency of C1s cleavage[a]

| SP | 28000 ± 2000 |
| --- | --- |
| CCP2-SP | 208000 ± 10000 |
| CCP1-CCP2-SP | 58000 ± 4000 |

[a] $k_{cat}/K_M$ (s$^{-1}$M$^{-1}$). Reactions were performed in 20 mM Tris, 145 mM NaCl, pH 7.4, at 30° C.

TABLE 7

Self-cleavage efficiency of the C1r fragments[a]

|  | SP S654A | CCP2-SP S654A | CCP1-CCP2-SP S654A |
| --- | --- | --- | --- |
| SP | 71000 | 75000 | 72000 |
| CCP2-SP | 68000 | 130000 | 74000 |
| CCP1-CCP2-SP | 45000 | 15900 | 6200 |

[a] $k_{cat}/K_M$ (s$^{-1}$M$^{-1}$). The S654A inactive zymogen mutants were used as substrates for the wild-type fragments. Reactions were performed in 20 mM Tris, 145 mM NaCl, pH 8.3, at 37° C. The values are the averages of 2-4 independent measurements. Variation between the results of the individual measurements was less than 10%.

The multidomain complement serine protease fragments of the invention are useful for a variety of purposes, e.g.
- as research tools in complement research,
- as standards or controls in several type of assay methods for assessing multidomain complement serine protease,
- for raising antibodies against multidomain complement serine proteases,
- for screening substrates or inhibitors of multidomain complement serine protease,
- for treatment, diagnosis and/or research of complement related diseases.

REFERENCES

Adachi et al., Trans. Proc. 19(1): 1145 (1987)
Ahrenstedt et al., New Engl. J. Med. 322:1345-9 (1990)
Antal, J., G. Pál, B. Asbóth, Zs. Buzás, A. Patthy, and L. Gráf. 2001. Specificity assay of serine proteinases by reverse-phase high-performance liquid chromatography analysis of competing oligopeptide substrate library. *Anal. Biochem.* 288:156.
Arlaud, G. J., and N. M. Thielens. 1993. Human complement serine proteases C1r and C1s and their proenzymes. *Methods Enzymol.* 223:61.
Arlaud, G. J., C. L. Villiers, S. Chesne, and M. G. Colomb. 1980. Purified proenzyme C1r. Some characteristics of its activation and subsequent proteolytic cleavage. *Biochim. Biophys. Acta* 616:116.

Arlaud, G. J., J. Gagnon, C. L. Villiers, and M. G. Colomb. 1986. Molecular characterization of the catalytic domains of human complement serine protease C1r. *Biochemistry* 25:5177.

Arlaud, G. J., M. G. Colomb, and J. Gagnon. 1987. A functional model of the human C1 complex. *Immunol. Today* 8:106.

Arlaud, G. J., S. Chesne, C. L. Villiers, and M. G. Colomb. 1980. A study on the structure and interactions of the C1 sub-components C1r and C1s in the fluid phase. *Biochim. Biophys. Acta* 616:105.

Aulak, K. S., V. H. Donaldson, M. Coutinho and A. E. Davis, 3rd (1993). C1-inhibitor: structure/function and biologic role. *Behring Inst Mitt:* 204-13.

J. S. Bonifacino, M. Dasso, J. B. Harford, J. Lippincott-Schwartz, K. M. Yamada: Current Protocols In Cell Biology Volume 2, Chapter 16 (2000) John Wiley & Sons, Inc. NY, US Brenner, S. 1988. The molecular evolution of genes and proteins: a tale of two serines. *Nature* 334:528.

Budayova-Spano, M., M. Lacroix, N. M. Thielens, G. J. Arlaud, J. C. Fontecilla-Camps, and C. Gaboriaud. 2002. The crystal structure of the zymogen catalytic domain of complement protease C1r reveals that a disruptive mechanical stress is required to trigger activation of the C1 complex. *EMBO J.* 21:231.

Castillo, M. J., K. Nakajima, M. Zimmerman, and J. C. Powers. 1979. Sensitive substrates for human leukocyte and porcine pancreatic elastase: a study of the merits of various chromophoric and fluorogenic leaving groups in assays for serine proteases. *Anal. Biochem.* 99:53.

Chen, C.-B., and R. Wallis. 2001. Stoichiometry of complexes between mannose-binding protein and its associated serine proteases: Defining functional units for complement activation. *J. Biol. Chem.* 276:25894.

Chenoweth et al., Complement. Inflamm. 3:152-165 (1981)

Chenoweth et al., Complement 3:152-165 (1986)

Clark, E. B. (1998) Refolding of recombinant proteins. *Current Opinion in Biotechnology* 9, 157-163

Collaborative Computational Project, Number 4. *Acta Cryst.* D50, 760 (1994)

Collard C D, Vakeva A, Morrissey M A, Agah A, Rollins S A, Reenstra W R, Buras J A, Meri S, Stahl G L. 2000. Complement activation after oxidative stress: role of the lectin complement pathway. *Am J Pathol* 156(5):1549-56

Dahl, M. R., S. Thiel, M. Matsushita, T. Fujita, A. C. Willis, T. Christensen, T. Vorup-Jensen, and J. C. Jensenius. 2001. MASP-3 and its association with distinct complexes of the mannan-binding lectin complement activation pathway. *Immunity* 15:127.

Demling et al., Surgery 106:52-9(1989)

Deppisch et al., Kidney Inst. 37:696-706 (1990)

Dobó, J., P. Gál, K. Szilágyi, S. Cseh, Z. Ló rincz, V. N. Schumaker, and P. Závodszky. 1999. One active C1r subunit is sufficient for the activity of the complement C1 complex: stabilization of C1r in the zymogen form by point mutations. *J. Immunol.* 162:1108.

Dodds, A. W. (1993). Small-scale preparation of complement components C3 and C4. *Methods Enzymol* 223: 46-61.

Dumestre-Perard C, Ponard D, Drouet C, Leroy V, Zarski J P, Dutertre N, Colomb M G. 2002. Complement C4 monitoring in the follow-up of chronic hepatitis C treatment. *Clin Exp Immunol.* 127(1):131-6.

Endo, Y., M. Takahashi, M. Nakao, H. Saiga, H. Sekine, M. Matsushita, M. Nonaka, and T. Fujita. 1998. Two lineages of mannose-binding lectin-associated serine protease (MASP) in vertebrates. *J. Immunol.* 161:4924.

Fraker, P. J. and J. C. Speck, Jr. (1978). Protein and cell membrane iodinations with a sparingly soluble chloroamide, 1,3,4,6-tetrachloro-3a,6a-diphrenylglycoluril. *Biochem Biophys Res Commun* 80: 849-57.

French, G. S., Wilson, K. S. *Acta Cryst. A*34, 517 (1978) G. S. French, K. S. Wilson *Acta Cryst. A*34, 517 (1978)

Gaboriaud, C., V. Rossi, I. Bally, G. J. Arlaud, and J. C. Fontecilla-Camps. 2000. Crystal structure of the catalytic domain of human complement C1s: a serine protease with a handle. *EMBO J.* 19:1755.

Gaboriaud, C., V. Rossi, J. C. Fontecilla-Camps, and G. J. Arlaud. 1998. Evolutionary conserved rigid module-domain interactions can be detected at the sequence level: the examples of complement and blood coagulation proteases. *J. Mol. Biol.* 282:459.

Gál, P., and G. Ambrus. 2001. Structure and function of complement activating enzyme complexes: C1 and MBL-MASPs. *Curr. Prot. Pept. Sci.* 2:43.

Gál. P., M. Sárvári, K. Szilágyi, P. Závodszky, and V. N. Schumaker. 1989. Expression of hemolytically active human complement component C1r proenzyme in insect cells using a baculovirus vector. *Complement Inflamm.* 6:433.

Gelfand et al, J. Clin. Invest. 70:1170 (1982)

Gill, S. C., and P. H. von Hippel. 1989. Calculation of protein extinction coefficients from amino acid sequence data. *Anal. Biochem.* 182:319.

Gráf, L., C. S. Craik, A. Patthy, S. Roczniak, R. J. Fletterick, and W. J. Rutter. 1987. Selective alteration of substrate specificity by replacement of aspartic acid-189 with lysine in the binding pocket of trypsin. *Biochem.* 26:2616.

Gulati, S., K. Sastry, J. C. Jensenius, P. A. Rice, and S. Ram. 2002. Regulation of the mannan-binding lectin pathway of complement on *Neisseria gonorrhoeae* by C1-inhibitor and á$_2$-macroglobulin. *J. Immunol.* 168:4078.

Guttman, Transplantation 17:383 (1974)

Hack et al., Am. J. Med. 86:20-26 (1989)

Hajela, K., J. Ferluga, G. Ambrus, P. Gál, K. Whaley, W. J. Schwaeble, and R. B. Sim. 2002. The mannose-binding lectin-MASPs system: a link between complement and the defensive role of coagulation. submitted Ji, Y-H., T. Fujita, H. Hatsuse, A. Takahashi, M. Matsushita, and M. Kawakami. 1993. Activation of the C4 and C2 components of complement by a proteinase in serum bactericidal factor, Ra reactive factor. *J. Immunol.* 150:571.

Jordan J E, Montalto M C, Stahl G L. 2001. Inhibition of mannose-binding lectin reduces postischemic myocardial reperfusion injury. *Circulation* 104(12):1413-8

Kardos, J., P. Gál, L. Szilágyi, N. M. Thielens, K. Szilágyi, Zs. Lõrincz, P. Kulcsár, L. Gráf, G. J. Arlaud, and P. Závodszky. 2001. The role of the individual domains in the structure and function of the catalytic region of a modular serine protease, C1r. *J. Immunol.* 167:5202.

Kawasaki, N., T. Kawasaki, and I. Yamashina. 1989. A serum lectin (mannan-binding protein) has complement-dependent bactericidal activity. *J. Biochem.* 106:483.

Kissinger, C. R., Gehlhaar, D. K., Fogel, D. B. *Acta Cryst.* D55, 484 (1999)

Kleiner D. E. and Stetler-Stevenson W. G. 1994. Quantitative zymography: detection of picogram quantities gelatinases. *Anal Biochem* 218(2):325

Knechtle et al., J. Heart Transplant 4(5):541 (1985)

Kojima et al., Nippon Jenzo Gakkai Shi 31:91-7 (1989)

Krem, M. M., and E. Di Cera. 2001. Molecular markers of serine protease evolution. *EMBO J.* 20:3036.

Krem, M. M., and E. Di Cera. 2002. Evolution of enzyme cascades from embryonic development to blood coagulation. *TIBS.* 27:67.

Lacroix, M. B., C. A. Aude, G. J. Arlaud, and M. G. Colomb. 1989. Isolation and functional characterization of the proenzyme form of the catalytic domains of human C1r. *Biochem. J.* 257:885.

Lacroix, M., C. Ebel, J. Kardos, J. Dobó, P. Gál, P. Závodszky, G. J. Arlaud, and N. M. Thielens. 2001. Assembly and enzymatic properties of the catalytic domain of human complement protease C1r. *J. Biol. Chem.* 276:36233.

Lacroix, M., V. Rossi, C. Gaboriaud, S. Chevallier, M. Jaquinod, N. M. Thielens, J. Gagnon, and G. J. Arlaud. 1997. Structure and assembly of the catalytic region of human complement protease C1r: A three-dimensional model based on chemical cross-linking and homology modeling. *Biochemistry* 36:6270.

Laemmli, U. K. 1970. Cleavage of structural proteins during the assembly of the head of bacteriophage T1. *Nature* 227:680.

Laich, A. and R. B. Sim (2001). Complement C4bC2 complex formation: an investigation by surface plasmon resonance. *Biochim Biophys Acta* 1544: 96-112.

Leslie, A. G. W. in *Crystallographic Computing*, Oxford University Press, Oxford (1990)

Leytus, S. P., K. Kurachi, K. S. Sakariassen, and E. W. Davie. 1986. Nucleotide sequence of the cDNA coding for human complement C1r. *Biochemistry* 25:4855.

Liota, L. A. and Stetler-Stevenson W. G. 1990 *Cancer Biology,* 1:96

Ló rincz, Zs., P. Gál, J. Dobó, S. Cseh, K. Szilágyi, G. Ambrus, and P. Závodszky. 2000. The cleavage of two C1s subunits by a single active C1r reveals substantial flexibility of the C1s-C1r-C1r-C1 s tetramer in the C1 complex. *J. Immunol.* 165:2048.

Luo, C., N. M. Thielens, J. Gagnon, P. Gál, M. Sárvári, Y. Tseng, M. Tosi, P. Závodszky, G. J. Arlaud, and V. N. Schumaker. 1992. Recombinant human complement subcomponent C1s lacking β-hydroxyasparagine, sialic acid, and one of its two carbohydrate chains still reassembles with C1q and C1r to form a functional C1 complex. *Biochemistry* 31:4254.

Matsushita, M. and Fujita, T. 1995. Cleavage of the third component of complement (C3) by mannose-binding protein-associated serine protease (MASP) with subsequent complement activation. *Immunobiology* 194:443.

Matsushita, M. and T. Fujita. 1992. Activation of the classical complement pathway by mannose-binding protein in association with a novel C1s-like serine protease. *J. Exp. Med.* 176:1497.

Matsushita, M., S. Thiel, J. C. Jensenius, I. Terai, and T. Fujita. 2000. Proteolytic activities of two types of mannose-binding lectin-associated serine protease. *J. Immunol.* 165:2637.

McRae, B. J., T. Y. Lin, and J. C. Powers. 1981. Mapping the substrate binding site of human C1r and C1s with peptide thioesters. *J. Mol. Biol.* 256:12362.

Monkovic, D. D., W. J. VanDusen, C. J. Petroski, V. M. Garsky, M. K. Sardana, P. Závodszky, A. M. Stem, and P. A. Friedman. 1992. Invertebrate aspartyl/asparaginyl β-hydroxylase: potential modification of endogenous epidermal growth factor-like modules. *Biochem. Biophys. Res. Commun.* 189:233.

Monsinjon T, Richard V, Fontaine M. 2001. Complement and its implications in cardiac ischemia/reperfusion: strategies to inhibit complement. *Fundam Clin Pharmacol* 15(5):293

Nagasawa, S. and R. M. Stroud (1977). Cleavage of C2 by C1s into the antigenically distinct fragments C2a and C2b: demonstration of binding of C2b to C4b. *Proc Natl Acad Sci USA* 74: 2998-3001.

Orsini, G., and M. E. Goldberg. 1978. The renaturation of reduced chymotrypsinogen A in guanidin HCl. Refolding versus aggregation. *J. Biol. Chem.* 253:3453.

Pangburn, M. K. and H. J. Muller-Eberhard (1983). Kinetic and thermodynamic analysis of the control of C3b by the complement regulatory proteins factors H and I. *Biochemistry* 22: 178-85.

pET System Manual TB055 $7^{th}$ Ed. 4/97. Novagen Inc., Madison

Peterson, F. C., N. C. Gordon, and P. G. W. Gettins. 2001. High-level bacterial expression and $^{15}$N-alanine-labeling of bovine trypsin. Application to the study of trypsin-inhibitor complexes and trypsinogen activation by NMR spectroscopy. *Biochem.* 40:6275.

Pilatte, Y., C. H. Hammer, M. M. Frank and L. F. Fries (1989). A new simplified procedure for C1-inhibitor purification. A novel use for jacalin-agarose. *J Immunol Methods* 120: 37-43.

Pilatte, Y., C. H. Hammer, M. M. Frank and L. F. Fries (1989). A new simplified procedure for C1-inhibitor purification. A novel use for jacalin-agarose. *J. Immunol Methods* 120: 37-43.

Privalov, P. L. 1979. Stability of proteins: small globular proteins. *Adv. Protein Chem.* 33:167.

Protein Data Bank id code: 1elv

Rossi, V., I. Bally, N. M. Thielens, A. F. Esser, and G. J. Arlaud. 1998. Baculovirus-mediated expression of truncated modular fragments from the catalytic region of human complement serine protease C1s. *J. Biol. Chem.* 273:1232.

Rossi, V., S. Cseh, I. Bally, N. M. Thielens, J. C. Jensenius, and G. J. Arlaud. 2001. Substrate specificities of recombinant mannan-binding lectin-associated serine proteases-1 and -2. *J. Biol. Chem.* 276:40880.

Rudolph, R and Lilie H (1996) In vitro folding of inclustion body proteins. *The Faseb Journal* 10: 49-56

Rudolph, R., and H. Lilie. 1996. In vitro folding of inclusion body proteins. *FASEB J.* 10:49.

Salama et al., N. Engl. J. Med. 318:408-14 (1988)

Salvesen, G. and J. J. Enghild (1993). alpha-Macroglobulins: detection and characterization. *Methods Enzymol* 223: 121-41.

Sato T., Endo Y., Matsushita M., Fujita T.; 1994 Molecular characterization of a novel serine protease involved in activation of the complement system by mannose-binding protein. *Int. Immunol.* 6:665-669.

Schumaker, V. N., P. Závodszky, and P. H. Poon. 1987. Activation of the first component of complement. *Annu. Rev. Immunol.* 5:21.

Sim, R. B. and A. Reboul (1981). Preparation and properties of human C1 inhibitor. *Methods Enzymol* 80: 43-54.

Sim, R. B., A. J. Day, B. E. Moffatt and M. Fontaine (1993). Complement factor I and cofactors in control of complement system convertase enzymes. *Methods Enzymol* 223: 13-35.

Sim, R. B., and A. Laich. (2000). Serine proteases of the complement system. *Biochem. Soc. Trans.* 28:545.

Sim, R. B., Arlaud, G. J., and Colomb, M. G. (1980) Kinetics of reaction of human C1-inhibitor with the human complement system proteases C1r and C1s. *Biochim. Biophys. Acta,* 612, 433-449

Soames, C. J. and R. B. Sim (1997). Interactions between human complement components factor H, factor I and C3b. *Biochem J.* 326: 553-61.

Stover, C. M., S. Thiel, M. Thelen, N. J. Lynch, T. Vorup-Jensen, J. C. Jensenius, and W. Schwaeble. (1999). Two constituents of the initiation complex of the mannan-binding lectin activation pathway of complement are encoded by a single structural gene. *J. Immunol.* 162:3481.

Szilágyi, L., E. Kénesi, G. Katona, Gy. Kaslik, G. Juhász, and L. Gráf. 2001. Comparative in vitro studies on native and recombinant human cationic trypsins. *J. Biol. Chem.* 276: 24574.

Tack, B. D. and J. W. Prahl (1976). Third component of human complement: purification from plasma and physicochemical characterization. *Biochemistry* 15: 4513-21.

Takada F., Takayama Y., Hatsuse H., Kawakami M.; (1993). A new member of the C1s family of complement proteins found in a bactericidal factor, Ra-reactive factor, in human serum.; *Biochem. Biophys. Res. Commun.* 196:1003-1009

Takahashi, M., Y. Endo, T. Fujita, and M. Matsushita. (1999). A truncated form of mannose-binding lectin-associated serine protease MASP-2 expressed by alternative polyadenylation is a component of the lectin complement pathway. *Int. Immunol.* 11:859.

Terai, I., K. Kobayashi, M. Matsushita, and T. Fujita. (1997). Human serum mannose-binding lectin (MBL)-associated serine protease-1 (MASP-1): determination of levels in body fluids and identification of two forms in serum. *Clin. Exp. Immunol.* 110:317.

Thiel S., Jensen T. V., Stover C. M., Schwaeble W. J., Laursen S. B., Poulsen K., Willis A. C., Eggleton P., Hansen S., Holmskov U., Reid K. B. M., Jensenius J. C. (1997) A second serine protease associated with mannan-binding lectin that activates complement. *Nature* 386:506-510.

Thiel, S., S. V. Petersen, T. Vorup-Jensen, M. Matsushita, T. Fujita, C. M. Stover, W. J. Schwaeble, and J. C. Jensenius. 2000. Interaction of C1q and mannan-binding lectin (MBL) with C1r, C1s, MBL-associated serine protease 1 and 2, and the MBL-associated protein MAp19. *J. Immunol.* 165:878.

Thiel, S., T. Vorup-Jensen, C. M. Stover, W. Schwaeble, S. B. Laursen, K. Poulsen, A. C. Willis, P. Eggleton, S. Hansen, U. Holmskov, K. B. M. Reid, and J. C. Jensenius. 1997. A second serine protease associated with mannan-binding lectin that activates complement. *Nature* 386:506.

Thijs et al., J. Immunol. 144:2419 (1990)

Thielens, M. N., S. Cseh, S. Thiel, T. Vorup-Jensen, V. Rossi, J. C. Jensenius, and G. J. Arlaud. 2001. Interaction properties of human mannan-binding lectin (MBL)-associated serine protease-1 and -2, MBL-associated protein 19, and MBL. *J. Immunol.* 166:5068.

Thielens, N. M., M. Lacroix, J. Dobó, P. Gál, P. Závodszky, and G. J. Arlaud. 1998. Expression and characterization of the proenzyme and activated forms of the catalytic region of human C1r. *Mol. Immunol.* 35:332.

Turner, M. W. 1996. Mannose-binding lectin: the pluripotent molecule of the innate immune system. *Immunol. Today* 17:532.

Villiers, C. L., G. J. Arlaud, and M. G. Colomb. 1985. Domain structure and associated functions of subcomponents C1r and C1s of the first component of human complement. *Proc. Natl. Acad. Sci. U.S.A.* 82:4477.

Volanakis, J. E., and G. J. Arlaud. 1998. Complement enzymes. In *The human Complement System in Health and Disease*, M. Frank, and J. E. Volanakis, eds. Marcel-Dekker, New York, p. 49.

Vorup-Jensen, T., S. V. Petersen, A. G. Hansen, K. Poulsen, W. Schwaeble, R. B. Sim, K. B. M. Reid, S. J. Davis, S. Thiel, and J. C. Jensenius. 2000. Distinct pathways of mannan-binding lectin (MBL)- and C1-complex autoactivation revealed by reconstitution of MBL with recombinant MBL-associated serine protease-2. *J. Immunol.* 165: 2093.

Wong, N. K. H., M. Kojima, J. Dobó, G. Ambrus, and R. B. Sim. 1999. Activities of the MBL-associated serine proteases (MASPs) and their regulation by natural inhibitors. *Mol. Immunol.* 36:853.

Zhang, Y., C. Suankratay, D. R. Jones, X. H. Zhang, T. F. Lint, and H. Gewurz. 1998. Lectin pathway hemolysis in the serum of the guinea pig and other species. *Mol. Immunol.* 35:390.

---

The invention claimed is:

1. A recombinant method for the preparation of an unglycosylated folded C-terminal fragment of a multidomain serine protease of the vertebrate complement cascade, wherein said multidomain serine protease is MASP-1, said method comprising the following steps:
   i) inserting into a bacterial expression vector a DNA sequence encoding a C-terminal fragment of a vertebrate MASP-1 serine protease and wherein the encoded C-terminal MASP-1 protein fragment consists of the domain structure CCP1-CCP2-SP fused at its amino terminus to a peptide amino acid sequence of either SEQ ID NO:19 or SEQ ID NO:20,
   ii) transforming a bacterial host cell with said expression vector,
   iii) inducing the expression of the MASP-1 C-terminal fragment consisting of the domain structure CCP1-CCP2-SP fused at its amino terminus to a peptide of SEQ ID NO:19 or SEQ ID NO:20,
   iv) isolating inclusion bodies comprising the unglycosylated MASP-1 C-terminal fragment fusion protein of step (iii) consisting of the domain structure CCP1-CCP2-SP fused at its amino terminus to a peptide of SEQ ID NO:19 or SEQ ID NO:20 from the bacterial host cell,
   v) renaturing the MASP-1 C-terminal fragment fusion protein of step (iv) to provide unglycosylated re-folded MASP-1 C-terminal fragment fusion protein, and
   vi) purifying the unglycosylated folded MASP-1 C-terminal fragment fusion protein.

2. A bacterial expression vector comprising an inserted DNA sequence encoding a C-terminal fragment of a vertebrate multidomain serine protease of the complement cascade wherein said multidomain serine protease is MASP-1 and the encoded C-terminal MASP-1 protein fragment consists of the domain structure CCP1-CCP2-SP fused at its amino terminus to a peptide amino acid sequence of SEQ ID NO:19 or SEQ ID NO:20.

3. An isolated, unglycosylated, and folded, C-terminal fragment of a vertebrate MASP-1 serine protease that has the domain structure CCP1-CCP2-SP and is fused at its amino terminus to a peptide consisting only of SEQ ID NO:19 or SEQ ID NO:20.

4. The isolated fragment of claim 3 which is autoactivated or capable of being autoactivated.

5. The isolated fragment of claim 3 wherein said fragment comprises a mutation selected from either or both of the following
   the activation site of the SP-domain is mutated to prevent autoactivation,
   the active Ser is mutated.

* * * * *